(12) United States Patent
Shimada et al.

(10) Patent No.: US 10,611,714 B2
(45) Date of Patent: Apr. 7, 2020

(54) METHOD FOR PRODUCING 1,1'-BINAPHTHYL DERIVATIVES AND 1,1'-BINAPHTHYL DERIVATIVES

(71) Applicant: KYOTO UNIVERSITY, Kyoto-shi, Kyoto (JP)

(72) Inventors: Toyoshi Shimada, Kyoto (JP); Kazuki Nakanishi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/078,288

(22) PCT Filed: Feb. 3, 2017

(86) PCT No.: PCT/JP2017/004117
§ 371 (c)(1),
(2) Date: Oct. 19, 2018

(87) PCT Pub. No.: WO2017/145716
PCT Pub. Date: Aug. 31, 2017

(65) Prior Publication Data
US 2019/0062246 A1    Feb. 28, 2019

(30) Foreign Application Priority Data
Feb. 22, 2016   (JP) ................. 2016-031194

(51) Int. Cl.
| | | |
|---|---|---|
| C07C 43/00 | (2006.01) | |
| C07C 46/00 | (2006.01) | |
| C07C 50/32 | (2006.01) | |
| C07C 303/00 | (2006.01) | |
| C07C 43/20 | (2006.01) | |
| C07C 309/66 | (2006.01) | |
| C07C 46/02 | (2006.01) | |
| C07C 303/26 | (2006.01) | |
| C07C 309/65 | (2006.01) | |

(52) U.S. Cl.
CPC ............ *C07C 43/202* (2013.01); *C07C 46/02* (2013.01); *C07C 50/32* (2013.01); *C07C 303/26* (2013.01); *C07C 309/65* (2013.01); *C07C 309/66* (2013.01); *Y02P 20/55* (2015.11)

(58) Field of Classification Search
CPC ....... C07C 43/202; C07C 46/02; C07C 50/32; C07C 303/26
See application file for complete search history.

(56) References Cited

FOREIGN PATENT DOCUMENTS

| WO | 2011099232 A1 | 8/2011 |
| WO | 2011111762 A1 | 9/2011 |

OTHER PUBLICATIONS

Tsubaki, K. et al., "Synthesis of chiral 2,2'-dimethyl-1,1'-binaphthyl-8,8'-diamine and barriers of atropisomerization of the related binaphthyls," Tetrahedron: Asymmetry, 2007, vol. 18, No. 8, pp. 1017-1021.
Kolotuchin, S. V. et al., "Synthesis of 8,8'-Disubstituted 1,1'-Binaphthyls Stable to Atropisomerization: 2,2'Dimethyl-1,1'-binaphthalene-8,8'-diol and 2,2'-Dimethyl-8,8'-bis(4-tert-butyloxazoly1)-1,1'-binaphthyl," Journal of Organic Chemistry, 1999, vol. 64, No. 21, pp. 7921-7928.
Yudin, A. K. et al., "F8BINOL, an Electronically Perturbed Version of BINOL with Remarkable Configurational Stability," Organic Letters, 2000, vol. 2, No. 1, pp. 41-44.
Chen, Y. et al., "Regioselective Substitution of Fluorine in F8BINOL as a Versatile Route to New Ligands with Axial Chirality," Organic Letters, 2000, vol. 2, No. 22, pp. 3433-3436.
Martyn, L. J. P. et al., "Catalytic applications of F8BINOL: asymmetric oxidation of sulfides to sulfoxides," Journal of Organometallic Chemistry, 2000, vol. 603, No. 1, pp. 98-104.
Yekta, S. et al., "Preparation and catalytic applications of partially fluorinated binaphthol ligands," Journal of Fluorine Chemistry, 2004, vol. 125, No. 4, pp. 517-525.
Biland-Thommen, A. S. et al., "Double benzyne-furan cycloaddition and the assembly of 1,1'-binaphthyl and 1,1'-dinaphthyl ether systems," Tetrahedron Letters, 2004, vol. 45, No. 16, pp. 3181-3184.
Laatsch, H., "Synthese von Maritinon und anderen 8,8'-Bijuglonen," Liebigs Annalen der Chemie, 1985, No. 12, pp. 2420-2442 (with English abstract).
Kamei, T. et al., "Scandium triflate-catalyzed 6,6'-diiodination of 2,2'-dimethoxy-1,1'-binaphthyl with 1,3-diiodo-5,5-dimethylhydantoin," Tetrahedron Letters, 2012, vol. 53, No. 30, pp. 3894-3896.
Yamashita, Y. et al., "Highly anti-Selective Asymmetric Aldol Reactions Using Chiral Zirconium Catalysts. Improvement of Activities, Structure of the Novel Zirconium Complexes, and Effect of a Small Amount of Water for the Preparation of the Catalysts," Journal of the American Chemical Society, 2002, vol. 124, No. 13, pp. 3292-3302.

(Continued)

*Primary Examiner* — Sikarl A Witherspoon
(74) *Attorney, Agent, or Firm* — Hamre, Schumann, Mueller & Larson, P.C.

(57) ABSTRACT

In a production method of the present disclosure, a 1,1'-binaphthyl precursor derivative, an organic acid, and an iodinating or brominating agent are mixed. The 1,1'-binaphthyl precursor derivative has a 1,1'-binaphthyl skeleton and has an electron-donating group at the 2-position of the 1,1'-binaphthyl skeleton and at the 2'-position of the 1,1'-binaphthyl skeleton, and the electron-donating group contains an oxygen atom directly bonded to the skeleton. With the production method of the present disclosure, a 1,1'-binaphthyl derivative having a substituent introduced at the 8-position and/or 8'-position of the 1,1'-binaphthyl skeleton can be obtained. The 1,1'-binaphthyl derivative obtained by the production method of the present disclosure can be a compound further having a substituent introduced at at least one position selected from the 4-position, 4'-position, 5-position, 5'-position, 6-position, and 6'-position of the 1,1'-binaphthyl skeleton.

26 Claims, 35 Drawing Sheets

(56) References Cited

OTHER PUBLICATIONS

International Search Report issued for International Patent Application No. PCT/JP2017/004117, dated Mar. 21, 2017, 9 pages including English translation.
Partial Supplementary European Search Report issued for European Patent Application No. 17756157.8, dated Jul. 24, 2019, 12 pages.
Thosz, M. et al., "The artificial binaphthyl amino acid 6-amino-6'-carboxyethyl-2-methoxy-2'-hydroxy-1,1'-binaphthyl (Bna): synthesis and assembly of Bna peptides," Tetrahedron, vol. 66, No. 44, 2010, pp. 8503-8511.

Chemical shift (ppm)

Chemical shift (ppm)

Chemical shift (ppm)

Chemical shift (ppm)

Chemical shift (ppm)

Chemical shift (ppm)

Chemical shift (ppm)

Chemical shift (ppm)

Chemical shift (ppm)

Chemical shift (ppm)

Chemical shift (ppm)

Chemical shift (ppm)

US 10,611,714 B2

METHOD FOR PRODUCING 1,1'-BINAPHTHYL DERIVATIVES AND 1,1'-BINAPHTHYL DERIVATIVES

TECHNICAL FIELD

The present invention relates to methods for producing 1,1'-binaphthyl derivatives and more specifically relates to, for example, a method for producing a 1,1'-binaphthyl derivative having a substituent introduced at a particular position of the binaphthyl skeleton, a method for producing a 1,1'-binaphthyl derivative from a naphthalene derivative, and a method for producing a further 1,1'-binaphthyl derivative from the above derivative having a substituent introduced at the particular position. The present invention also relates to new 1,1'-binaphthyl derivatives obtained by these production methods.

BACKGROUND ART 1,1'-binaphthyl, which has a molecular structure composed of two naphthalene skeletons bonded together at their 1-positions, is converted to a 1,1'-binaphthyl derivative in the form of an axially chiral compound by introducing substituents at the 2-position and 2'-position of the skeleton (binaphthyl skeleton) of 1,1'-binaphthyl. Known examples of such a 1,1'-binaphthyl derivative include 2,2'-bis(diphenylphosphino)-1,1'-binaphthyl (BINAP) having diphenylphosphino groups (—PPh$_2$) at the 2-position and 2'-position and 1,1'-bi-2-naphthol (BINOL) having hydroxy groups (—OH) at the 2-position and 2'-position. For example, based on the axial chirality, BINAP and BINOL are used as favorable chiral ligands to transition metals and typical metals in catalytic asymmetric synthesis reactions or in construction of sites for chiral molecular recognition.

Concerning a 1,1'-binaphthyl derivative having alkoxy groups such as methoxy groups or hydroxy groups at the 2-position and 2'-position of the binaphthyl skeleton, there has been an attempt to introduce a substituent at another position of the binaphthyl skeleton. The introduction of a substituent at a position other than the 2-position and 2'-position, coupled with the fact that the alkoxy groups at the 2-position and 2'-position can be converted to hydroxy groups by hydrolysis if necessary, is expected to extend the range of possible applications of binaphthyl derivatives having a BINOL skeleton or a skeleton analogous to BINOL.

Non Patent Literature 1 discloses a method for introducing iodo groups (—I) or pentafluoroethyl groups (—C$_2$F$_5$) at the 3-position, 3'-position, 6-position, and 6'-position of the binaphthyl skeleton of BINOL having hydroxy groups at the 2-position and 2'-position. This method necessarily involves multiple reactions including a protection reaction for protecting the hydroxyl groups with methoxymethyl (MOM) groups and an elimination reaction for eliminating the MOM groups acting as protecting groups and cannot achieve direct introduction of substituents to the skeleton. Non Patent Literature 2 discloses a method for introducing iodo groups (—I) at the 6-position and 6'-position of the skeleton of a 1,1'-binaphthyl derivative having methoxy groups at the 2-position and 2'-position in the presence of a Sc(OTf)$_3$ catalyst.

Patent Literature 1 discloses a method for introducing iodo groups (—I) at the 3-position and 3'-position, or the 3-position, 3'-position, 6-position, and 6'-position of the skeleton of a 1,1'-binaphthyl derivative having methoxy groups at the 2-position and 2'-position in the presence of a Lewis acid. Patent Literature 1 also states that the use of a trifluoromethanesulfonic acid which is a Brønsted acid instead of a Lewis acid fails to allow the substituent introduction reaction to take place.

CITATION LIST

Patent Literature

Patent Literature 1: WO 2011/099232 A1

Non Patent Literature

Non Patent Literature 1: Y. Yamashita et al., "Highly anti-Selective Asymmetric Aldol Reactions Using Chiral Zirconium Catalysts. Improvement of Activities, Structure of the Novel Zirconium Complexes, and Effect of a Small Amount of Water for the Preparation of the Catalysts", Journal of American Chemical Societies, (2002), vol. 124, pp. 3292-3302

Non Patent Literature 2: T. Kamei et al., "Scandium triflate-catalyzed 6,6'-diiodination of 2,2'-dimethoxy-1,1'-binaphtyl with 1,3-diiodo-5,5-dimethylhydantoin", Tetrahedron Letters vol. 53, (2012), pp. 3894-3896

SUMMARY OF INVENTION

Technical Problem

Any method for introducing a substituent at the 8-position and/or 8'-position of 1,1'-binaphthyl derivatives such as BINOL has been unknown. An object of the present invention is to provide a method for producing 1,1'-binaphthyl derivatives having a substituent introduced at the 8-position and/or 8'-position of a binaphthyl skeleton.

Solution to Problem

A method for producing 1,1'-binaphthyl derivatives according to the present disclosure (first production method) is a method including mixing a 1,1'-binaphthyl precursor derivative, an organic acid, and an iodinating or brominating agent to obtain a 1,1'-binaphthyl derivative, the 1,1'-binaphthyl precursor derivative having a 1,1'-binaphthyl skeleton and having an electron-donating group at 2-position of the skeleton and at 2'-position of the skeleton, the electron-donating group containing an oxygen atom directly bonded to the skeleton, the 1,1'-binaphthyl derivative having a substituent introduced at 8-position and/or 8'-position of the skeleton.

From another aspect, a method for producing 1,1'-binaphthyl derivatives according to the present disclosure (second production method) includes mixing a naphthalene derivative, an organic acid, and an iodinating or brominating agent to allow a coupling reaction of the naphthalene derivative to take place so as to obtain a 1,1'-binaphthyl derivative, the naphthalene derivative having a naphthalene skeleton and having a substituent at 2-position of the naphthalene skeleton, the 1,1'-binaphthyl derivative having a 1,1'-binaphthyl skeleton and having a substituent at 2-position of the 1,1'-binaphthyl skeleton and at 2'-position of the 1,1'-binaphthyl skeleton.

From another aspect, a method for producing 1,1'-binaphthyl derivatives according to the present disclosure (third production method) includes allowing a 1,1'-binaphthyl derivative represented by the following formula (1) to undergo a reaction involving at least one group selected from $Y^1$, $Y^2$, —$OR^1$, —$OR^2$, and at least one X so as to obtain a 1,1'-binaphthyl derivative that is a result of the reaction and different from the derivative represented by the formula (1). In the formula (1), X is an iodo group or a bromo group, $R^1$ and $R^2$ are each independently a hydrogen atom, an alkyl group having 1 to 50 carbon atoms, an allyl group, a benzyl group, a trifluoromethanesulfonyl group, a silyl group, or a protecting group for a hydroxy group, and $Y^1$ and $Y^2$ are each independently a hydroxy group or an organic acid group containing an oxygen atom directly bonded to the binaphthyl skeleton of the derivative.

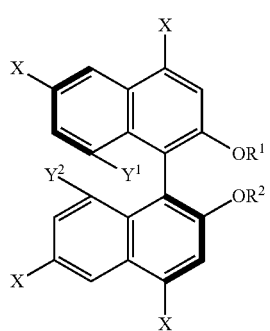

(1)

A 1,1'-binaphthyl derivative according to the present disclosure has a binaphthyl skeleton and has a substituent at 8-position and/or 8'-position of the binaphthyl skeleton.

Advantageous Effects of Invention

According to the present invention, methods for producing 1,1'-binaphthyl derivatives having a substituent introduced at the 8-position and/or 8'-position of a binaphthyl skeleton can be established. According to the present invention, new 1,1'-binaphthyl derivatives having a substituent introduced at the 8-position and/or 8'-position of the binaphthyl skeleton can be obtained.

DESCRIPTION OF EMBODIMENTS

Figure 1:
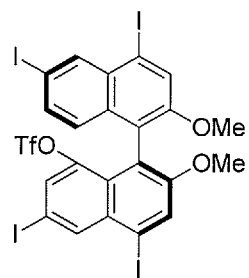
FIG. 1 shows examples of 1,1'-binaphthyl derivatives that can be formed by a production method of the present invention.
Figure 1:
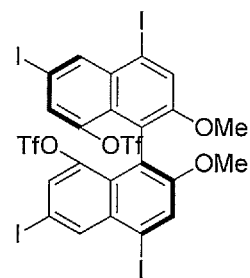
Figure 1:
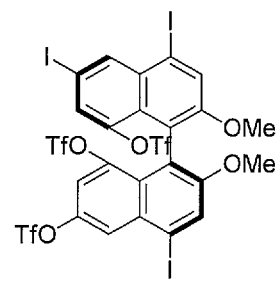
Figure 1:
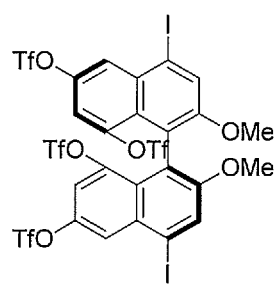
Figure 1:
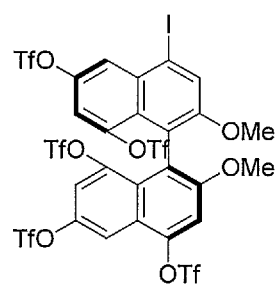
Figure 1:
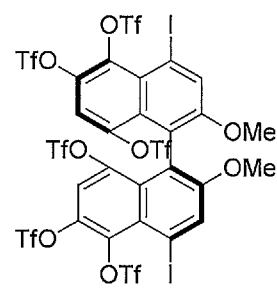
Figure 1:
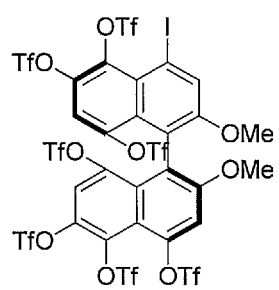
Figure 1:
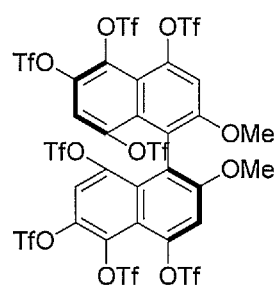
Figure 1:
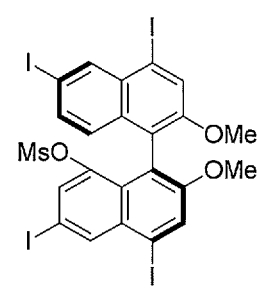
Figure 1:
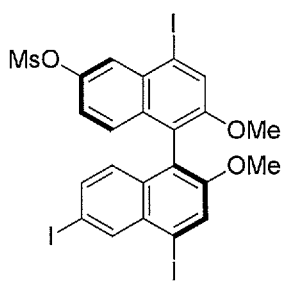
Figure 1:
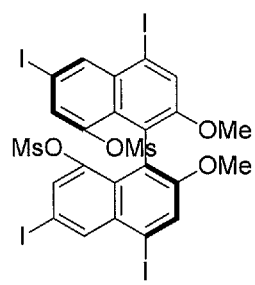
Figure 1:
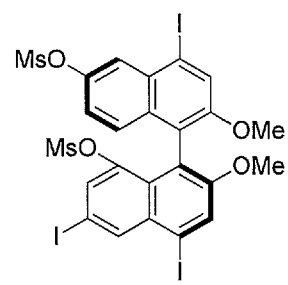
Figure 2:
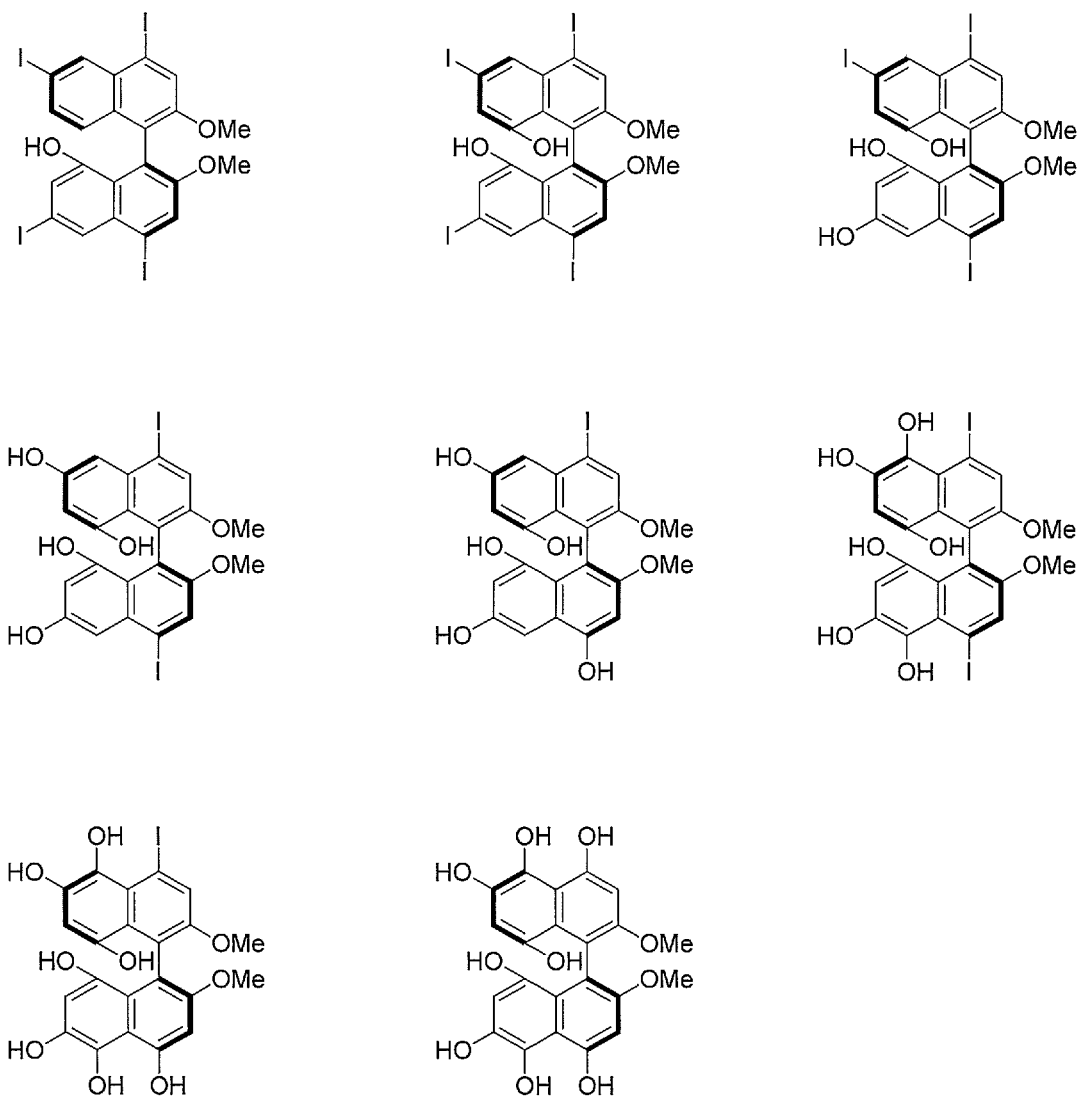
FIG. 2 shows other examples of 1,1'-binaphthyl derivatives that can be formed by the production method of the present invention.
Figure 3:
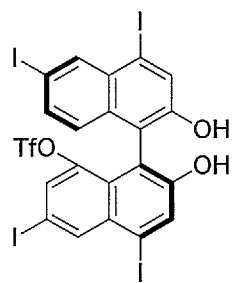
FIG. 3 shows still other examples of 1,1'-binaphthyl derivatives that can be formed by the production method of the present invention.
Figure 3:
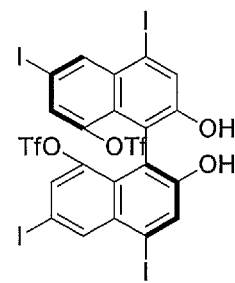
Figure 3:
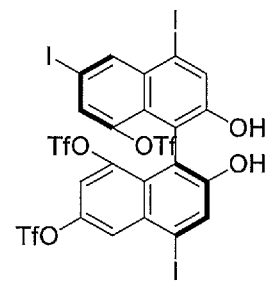
Figure 3:
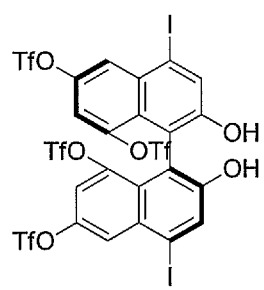
Figure 3:
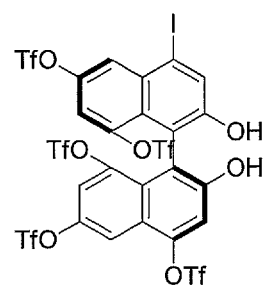
Figure 3:
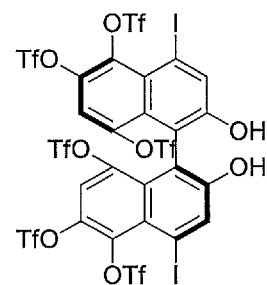
Figure 3:
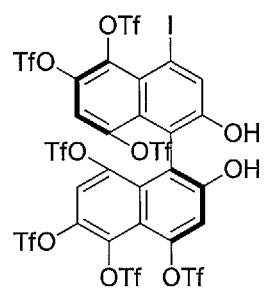
Figure 3:
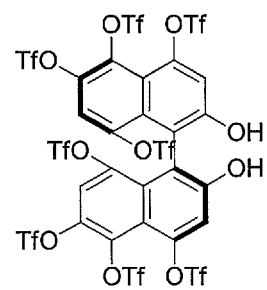
Figure 3:
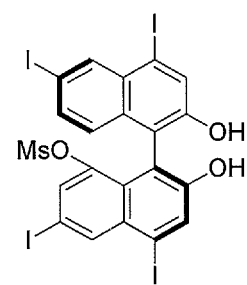
Figure 3:
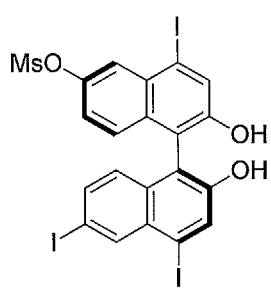
Figure 3:
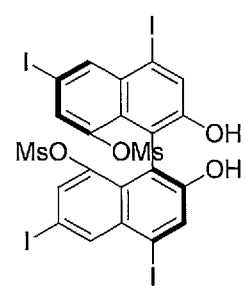
Figure 3:
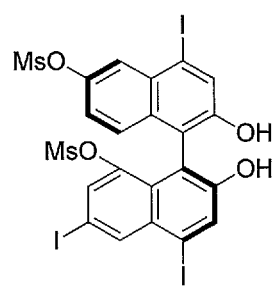
Figure 4:
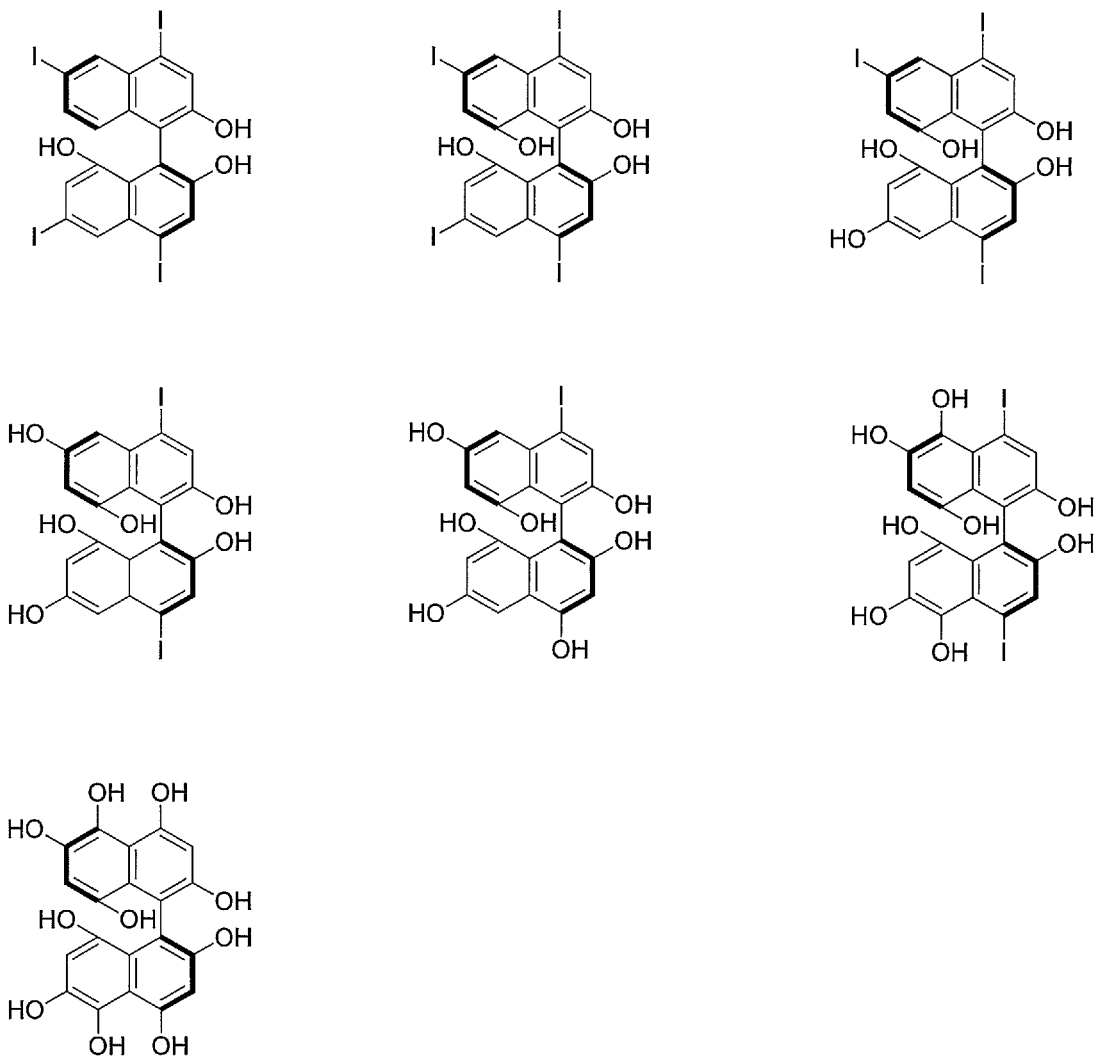
FIG. 4 shows still other examples of 1,1'-binaphthyl derivatives that can be formed by the production method of the present invention.

Methods for Producing 1,1'-Binaphthyl Derivatives (First Production Method)

According to the first production method, a 1,1'-binaphthyl precursor derivative (A), an organic acid, and an iodinating or brominating agent are mixed to obtain a 1,1'-binaphthyl derivative (B) having a substituent $Z^1$ introduced at the 8-position and/or 8'-position of a binaphthyl skeleton. The precursor derivative (A) has a 1,1'-binaphthyl skeleton having an electron-donating group $Z^2$ at the 2-position and at the 2'-position ("1,1'-binaphthyl skeleton" may be simply referred to as "binaphthyl skeleton" hereinafter). The electron-donating group $Z^2$ contains an oxygen atom directly bonded to the binaphthyl skeleton.

In the first production method, a reaction system containing the precursor derivative (A), an organic acid, and an iodinating or brominating agent is employed to cause a reaction for introduction of a substituent at the 8-position and/or 8'-position of the binaphthyl skeleton of the precursor derivative (A). This introduction reaction can be a reaction in which the substituent is directly introduced into the binaphthyl skeleton. Although reactions for introduction of a substituent at the 3-position, 3'-position, 6-position, or 6'-position of a binaphthyl skeleton have been already known (See Non Patent Literatures 1 and 2 and Patent Literature 1), the introduction of a substituent at the 8-position or 8'-position of a binaphthyl skeleton has been difficult. This is attributed to the fact that electronic and steric factors of the binaphthyl skeleton composed of naphthalene skeletons bonded together at the 1-position and 1'-position make difficult the introduction of a substituent at the 8-position and 8'-position of the binaphthyl skeleton. Additionally, if a binaphthyl skeleton has substituents such as hydroxy groups or methoxy groups bonded at the 2-position and 2'-position of the binaphthyl skeleton, the difficulty of introduction of another substituent into the binaphthyl skeleton is increased because the substituents at the 2-position and 2'-position are so reactive that protection of these substituents with protecting groups and the subsequent elimination of the protecting groups are required (see Non Patent Literature 1). Nevertheless, the first production method is a method enabling that introduction of a substituent at the 8-position and/or 8'-position of a binaphthyl skeleton which cannot be expected from the traditional technical knowledge. Furthermore, the first production method avoids the need to protect the electron-donating groups $Z^2$ at the 2-position and 2'-position of the precursor derivative (A) with protecting groups and subsequently eliminate the protecting groups. This means that direct introduction of a substituent at the 8-position and/or 8'-position of the binaphthyl skeleton can be accomplished.

The electron-donating groups $Z^2$ present at the 2-position and 2'-position of the binaphthyl skeleton of the precursor derivative (A) are not limited as long as each electron-donating group $Z^2$ has the ability to donate an electron to the binaphthyl skeleton and contain an oxygen atom directly bonded to the binaphthyl skeleton. The electron-donating group $Z^2$ may be —OR wherein R is, for example, a hydrogen atom, an alkyl group having 1 to 50 carbon atoms, an allyl group, a benzyl group, a trifluoromethanesulfonyl group, a silyl group, or a protecting group for a hydroxy group. Specific examples of R include methyl, (meth)allyl, ethyl, ethynyl, vinyl, n-propyl, propargyl, n-butyl, i-butyl, t-butyl, n-pentyl, n-hexyl, cyclohexyl, n-pentyl, neopentyl, n-octyl, n-nonyl, n-decyl, n-dodecyl, n-myristyl, n-palmityl, n-stearyl, methoxymethyl (MOM), methylthiomethyl (MTM), 2-methoxyethoxymethyl (MEM), tetrahydropyranyl (THP), benzyl, o-nitrobenzyl, p-methoxybenzyl, trimethylsilyl, t-butyldimethylsilyl, triisopropyl, t-butyldiphenylsilyl, formyl, acetyl, trichloroacetyl, trifluoroacetyl, pivaloyl, benzoate, methanesulfonyl, trifluoromethanesulfonyl, p-toluenesulfonyl, phosphonite, phosphinite, phosphite, phosphonate, phosphoramidite, phosphorodiamidite, and carbamyl groups. R may have an ester group, a silyl group, or an ether group and can be an alkenyl group, an alkynyl group, or an aralkyl group. The substituent $Z^2$ bonded at the 2-position of the binaphthyl skeleton and the substituent $Z^2$ bonded at the 2'-position of the binaphthyl skeleton may be the same or different. That is, the electron-donating group present at the 2-position of the binaphthyl skeleton of the precursor derivative (A) may be —OR$^1$, the electron-donating group present at the 2'-position of the binaphthyl skeleton of the precursor derivative (A) may be —OR$^2$, and R$^1$ and R$^2$ may be each independently a hydrogen atom, an alkyl group having 1 to 50 carbon atoms, an allyl group, a benzyl group, a trifluoromethanesulfonyl group, a silyl group, or a protecting group for a hydroxy group. R is preferably a hydrogen atom, an alkyl group having 1 to 50 carbon atoms, or a trifluoromethanesulfonyl group and more preferably a hydrogen atom, a methyl group, or a trifluoromethanesulfonyl group. Likewise, R$^1$ and R$^2$ are preferably each independently a hydrogen atom, an alkyl group having 1 to 50 carbon atoms, or a trifluoromethanesulfonyl group and more preferably each independently a hydrogen atom, a methyl group, or a trifluoromethanesulfonyl group.

Specific examples of the protecting group for a hydroxy group include (meth)allyl, methoxymethyl, and silyl groups.

When R, R$^1$, and R$^2$ are each an allyl group, a benzyl group, a trifluoromethanesulfonyl group, or a silyl group, the groups —OR, —OR$^1$, and —OR$^2$ are each an allyloxy group, a benzyloxy group, a trifluoromethanesulfonyloxy group, or a silyloxy group.

The precursor derivative (A) may have a substituent $Z^3$ at a position other than the 2-position and 2'-position of the binaphthyl skeleton, and the substituent $Z^3$ may or may not be the electron-donating group $Z^2$. It should be noted that the precursor derivative (A) does not have any substituent at least one position selected from the 8-position and 8'-position of the binaphthyl skeleton and typically does not have any substituent at either the 8-position or the 8'-position. The first production method can yield a 1,1'-binaphthyl derivative (B) having a substituent $Z^1$ introduced at the 8-position or 8'-position of the binaphthyl skeleton at which the precursor derivative (A) does not have any substituent. With the first production method, a 1,1'-binaphthyl derivative (B) having substituents $Z^1$ introduced at both the 8-position and 8'-position of the binaphthyl skeleton can be formed. In this instance, the substituent $Z^1$ introduced at the 8-position and the substituent $Z^1$ introduced at the 8'-position may be the same or different.

The substituent $Z^1$ introduced at the 8-position and/or 8'-position of the binaphthyl skeleton of the precursor derivative (A) by the first production method (the substituent $Z^1$ present at the 8-position and/or 8'-position of the binaphthyl skeleton of the binaphthyl derivative (B)) is typically at least one group selected from an organic acid group, a hydroxy group, and an iodo group (in the case where an iodinating agent is used) or a bromo group (in the case where a brominating agent is used) at the stage when a reaction induced by mixing the precursor derivative (A), an organic acid, and an iodinating or brominating agent has been completed (the stage when the substituent $Z^1$ has been introduced at the 8-position and/or 8'-position of the binaphthyl skeleton). When the above reaction is followed by a further reaction, another substituent $Z^1$ derived from the at least one group can be placed at the 8-position and/or 8'-position of the binaphthyl derivative (B). The reaction for deriving the other substituent $Z^1$ can be a known reaction. The first production method includes the step of mixing the precursor derivative (A), an organic acid, and an iodinating or brominating agent and may further include the step of allowing the further reaction to take place.

Whether the substituent $Z^1$ introduced at the 8-position and/or 8'-position of the binaphthyl skeleton is an organic acid group, a hydroxy group, an iodo group, or a bromo group can be controlled, for example, by controlling the reaction conditions such as the type and amount (e.g., equivalents per equivalent of the precursor derivative (A)) of the organic acid used, the type and amount of the iodinating or brominating agent used, the reaction temperature, and the reaction time. Quantitative reaction conditions such as the amount of the organic acid used and/or the iodinating or brominating agent used can also be controlled. In general, as the reaction conditions become harsher, the reaction shifts from introduction of an iodo group or bromo group to introduction of an organic acid group. The organic acid group can be converted to a hydroxy group relatively easily by a hydrolysis reaction.

When the substituent $Z^1$ is an organic acid group or a hydroxy group, this means that a reaction taking place in the first production method is an oxidation reaction in which a hydrogen atom at the 8-position and/or 8'-position of the binaphthyl skeleton is directly substituted by an oxygen atom. This reaction is characteristic of the first production method, and it has not been known that such a reaction occurs on the binaphthyl skeleton. Considering this reaction in terms of the organic acid and the iodinating or brominating agent which are mixed with the precursor derivative (A) in the first production method, it can be said that a reaction in which the organic acid group is directly bonded at the 8-position and/or 8'-position of the binaphthyl skeleton takes place despite the mixing of the iodinating or brominating agent. Such a reaction is presumed to be a radical reaction because the reaction can be terminated by the addition of a radical scavenger (such as galvinoxyl free radical) to the reaction system.

The organic acid is not particularly limited and is, for example, at least one selected from trifluoromethanesulfonic acid, methanesulfonic acid, trifluoroacetic acid, and p-toluenesulfonic acid. The organic acid is preferably trifluoromethanesulfonic acid (TfOH) in order to inhibit the formation of by-products and allow the introduction of the substituent $Z^1$ at the 8-position and/or 8'-position of the binaphthyl skeleton to take place efficiently.

The organic acid group is a group derived from the organic acid, and a more specific example of the organic acid group is a group resulting from removal of one hydrogen atom from the organic acid.

When TfOH is used as the organic acid, the organic acid group as the substituent $Z^1$ is a trifluoromethanesulfonic acid group (TfO group). Likewise, when methanesulfonic acid, trifluoroacetic acid, or p-toluenesulfonic acid is used as the organic acid, the organic acid group as the substituent $Z^1$ is a methanesulfonic acid (MsO group), a trifluoroacetic acid group, or a p-toluenesulfonic acid group.

The iodinating agent is not particularly limited and is, for example, at least one selected from 1,3-diiodo-5,5-dimethylhydantoin (DIH) and N-iodosuccinimide (NIS). The iodinating agent is preferably DIH in order to inhibit the formation of by-products and allow the introduction of the substituent $Z^1$ at the 8-position and/or 8'-position of the binaphthyl skeleton to take place efficiently.

The brominating agent is not particularly limited and is, for example, at least one selected from 1,3-dibromo-5,5-dimethylhydantoin (DBH) and N-bromosuccinimide.

In this reaction system, it is preferable to use the iodinating agent because the use of the iodinating agent allows the introduction of the substituent $Z^1$ at the 8-position and/or 8'-position of the binaphthyl skeleton to take place more efficiently and because the reactivity of the substituent $Z^1$ in the above-mentioned further reaction such as a cross-coupling reaction is higher when the substituent $Z^1$ is an iodo group than when the substituent $Z^1$ is a bromo group. That is, in the first production method, it is preferable to mix the precursor derivative (A), the organic acid, and the iodinating agent.

The reaction system is not limited to a specific system as long as mixing of the precursor derivative (A), the organic acid, and the iodinating or brominating agent induces the reaction for introducing the substituent $Z^1$ at the 8-position and/or 8'-position of the binaphthyl skeleton. The reaction system is typically a solution system. The solvent used in the solution system is preferably a solvent capable of dissolving the precursor derivative (A), the organic acid, the iodinating or brominating agent, and the binaphthyl derivative (B) produced. Specific examples of the solvent used in the solution system include dichloromethane, chloroform, dichloroethane, chlorobenzene, and toluene. Dichloromethane and dichloroethane are preferred from the viewpoint of the relative permittivity and the stability of a reaction intermediate.

The reaction system may, if necessary, contain a substance other than the precursor derivative (A), the organic acid, and the iodinating or brominating agent. The substance is, for example, an inorganic acid such as sulfuric acid. When the reaction system contains an inorganic acid, the amount of the organic acid to be used can be decreased depending on the type of the organic acid (e.g., trifluoromethanesulfonic acid). Other examples of the substance include catalysts (including promoters) for controlling the reaction rate and radical scavengers.

In the first production method, a substituent $Z^4$ can be further introduced at a position other than the 8-position and/or 8'-position of the binaphthyl skeleton of the precursor derivative (A) by controlling the reaction conditions. This characteristic also offers a significant advantage over conventional techniques. The substituent $Z^4$ may be the same as the substituent $Z^1$. In the resulting binaphthyl derivative (B), the substituents $Z^1$ and $Z^4$ may be the same or different. When substituents $Z^4$ are introduced at a plurality of positions, the specific types of the substituents $Z^4$ may be the same among all the positions or may be different between any two or more of the positions. Examples of the reaction conditions that may be controlled include the type and amount of the organic acid used, the type and amount of the iodinating or brominating agent used, the reaction temperature, and the reaction time. Quantitative reaction conditions such as the amount of the organic acid used and/or the amount of the iodinating or brominating agent used can also be controlled. Controlling the reaction conditions allows control of the position of the binaphthyl skeleton at which the substituent $Z^4$ is introduced. In general, as the reaction conditions become harsher, the introduction of the substituent $Z^4$ comes to occur at the 6-position and/or 6'-position in addition to the introduction of the substituent $Z^1$ at the 8-position and 8'-position. As the reaction conditions become even harsher, the introduction of the substituent $Z^4$ will further take place at the 5-position and/or 5'-position and even at the 4-position and/or 4'-position. In the first production method, the resulting binaphthyl derivative (B) may have the substituent $Z^4$ introduced at at least one position selected from the 4-position, 4'-position, 5-position, 5'-position, 6-position, and 6'-position of the binaphthyl skeleton.

The substituents at the 2-position and 2'-position of the binaphthyl skeleton in the binaphthyl derivative (B) may be the substituents $Z^2$ at the 2-position and 2'-position of the binaphthyl skeleton in the precursor derivative (A) or may be substituents derived from the substituents $Z^2$ through a further reaction. This reaction is, for example, conversion of an alkoxy group $Z^2$ into a hydroxy group. The substituents at the 2-position and 2'-position of the binaphthyl skeleton in the binaphthyl derivative (B) may be the same as the substituent $Z^1$ or $Z^4$.

Additionally, in the first production method, the type of the substituent $Z^4$ can, like the type of the substituent $Z^1$, be controlled by controlling the reaction conditions mentioned above. This means that, for example, when the precursor derivative (A) has a substituent at a position other than the 2-position and 2'-position (the precursor derivative (A) has a substituent $Z^3$) and the substituent $Z^3$ is an iodo or bromo group, the iodo or bromo group can be substituted by an organic acid group or hydroxy group (ipso substitution) by controlling the reaction conditions. When the substituents $Z^1$ and $Z^4$ introduced into the binaphthyl skeleton vary from iodo or bromo groups to organic acid groups with increasing harshness of the reaction conditions, this substitution is presumed to take place as a reaction mechanism in which the iodo or bromo groups having been introduced into the skeleton are substituted by the organic acid groups.

As seen from the foregoing description, the first production method is capable of forming a binaphthyl derivative (B) having, for example, a plurality of organic acid groups, in particular TfO groups, introduced as the substituents $Z^1$ and $Z^4$ into the binaphthyl skeleton. The method is also capable of forming a binaphthyl derivative (B) having a plurality of hydroxy groups introduced as the substituents $Z^1$ and $Z^4$ into the binaphthyl skeleton. An exemplary binaphthyl derivative (B) is one that has organic acid groups such as TfO groups and/or hydroxy groups at all the positions of the binaphthyl skeleton (except for the 1-position and 1'-position which are necessarily involved in formation of the binaphthyl skeleton). Such a binaphthyl derivative (B) may be a binaphthyl derivative (B) having organic acid groups at all the positions or a binaphthyl derivative (B) having hydroxy groups at all the positions. Another exemplary binaphthyl derivative (B) is one that has organic acid groups such as TfO groups and/or hydroxy groups at all the positions other than the 3-position and 3'-position of the binaphthyl skeleton (except for the 1-position and 1'-position which are necessarily involved in formation of the binaphthyl skeleton). Such a binaphthyl derivative (B) may be a binaphthyl derivative (B) having organic acid groups at all the positions other than the 3-position and 3'-position or a binaphthyl derivative (B) having hydroxy groups at all the position other than the 3-position and 3'-position.

Exemplary binaphthyl derivatives (B) that can be formed by the first production method are shown in FIGS. 1 to 4.

As seen from the foregoing description, the first production method is capable of forming not only the examples shown in FIGS. 1 to 4 but also binaphthyl derivatives (B) having the substituents $Z^1$ and $Z^4$ in any combination at the positions other than the 1-position and 1'-position of the binaphthyl skeleton. For example, a binaphthyl derivative (B) may have a binaphthyl skeleton having a position at which any substituent is not present. For example, a binaphthyl derivative (B) in which at least one TfO group of any of the binaphthyl derivatives (B) shown in FIGS. 1 to 4 is replaced by another organic acid group such as a MsO group can be formed. For example, it is possible to form a binaphthyl derivative (B) in which the substituent bonded at the 2-position and/or 2'-position of the binaphthyl skeleton of any of the binaphthyl derivatives (B) shown in FIGS. 1 to 4 is a TfO group rather than a methoxy group or a binaphthyl derivative (B) in which the substituent bonded at the 2-position and/or 2'-position of any of the binaphthyl derivatives (B) mentioned as specific examples in the present specification is a TfO group rather than a methoxy group. Examples of binaphthyl derivatives (B) that can be formed by the first production method are presented also in EXAMPLES below.

With the first production method, binaphthyl derivatives (B) in the form of (R)-isomers can be obtained, although FIGS. 1 to 4 show (S)-isomers. The same applies to the other derivatives shown as examples in the form of (S)-isomers. A binaphthyl derivative (B) in the form of a mixture of an (S)-isomer and (R)-isomer (in the form of a racemate) can be separated into the (S)-isomer and (R)-isomer through a step of chiral resolution (a step of selectively obtaining the (S)-isomer or (R)-isomer from the binaphthyl derivative in the form of a racemate). With the first production method, there is a possibility that a binaphthyl derivative (B) can be formed with the axial chirality of the precursor derivative (A) remaining intact. This characteristic offers a significant advantage over conventional techniques. Specifically, the step of chiral resolution can be omitted when a binaphthyl derivative (B) is to be obtained in the form of either of the optical isomers, (S)-isomer and (R)-isomer.

Examples of the technique used for chiral resolution include inclusion complex formation, preferential enrichment, chiral column chromatography, and enzymatic resolution.

Examples of the reaction conditions will be described hereinafter. When either of the two precursor derivatives (A) represented by formulae (2) and (3) below is used, the conditions optimal for obtaining a binaphthyl derivative (B) having eight TfO groups as the substituents $Z^1$ and $Z^4$ and represented by, for example, formula (4) below are, for example, as follows: DIH is used as the iodinating agent in an amount of 25 equivalents per equivalent of the precursor derivative (A); TfOH is used as the organic acid in an amount of 50 equivalents per equivalent of the precursor derivative (A); dichloromethane is used as the solvent; the reaction temperature is room temperature; and the reaction time is 12 hours. When the amount of DIH is adjusted to 30 equivalents and the amount of TfOH to 60 equivalents without changing the solvent and reaction temperature, the reaction time can be reduced to 1 hour. The precursor derivative (A) represented by the formula (2) is (S)-4,4',6,6'-tetraiodo-2,2'-dimethoxy-1,1'-binaphthyl, the precursor derivative (A) represented by the formula (3) is (S)-2,2-dimethoxy-1,1'-binaphthyl, and the binaphthyl derivative (B) represented by the formula (4) is (S)-4,4',5,5',6,6',8,8'-octakis(trifluoromethanesulfonyloxy)-2,2'-dimethoxy-1,1'-binaphthyl.

(2)

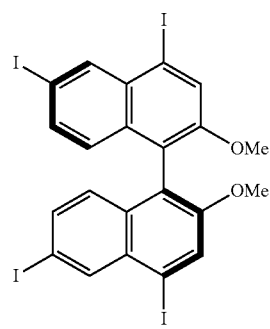

(3)

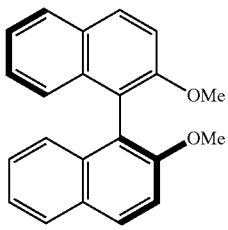

(4)

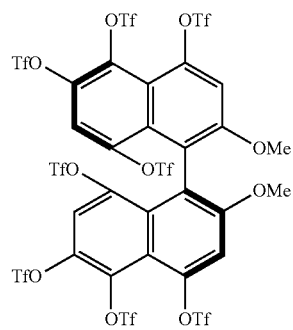

When either of the two precursor derivatives (A) represented by the formulae (2) and (3) is used, the conditions optimal for obtaining a binaphthyl derivative (B) having two TfO groups as the substituents $Z^1$ and $Z^4$ and represented, for example, by formula (5) below are, for example, as follows: DIH is used as the iodinating agent in an amount of 3 equivalents per equivalent of the precursor derivative (A); TfOH is used as the organic acid in an amount of 5 equivalents per equivalent of the precursor derivative (A); dichloromethane is used as the solvent; the reaction temperature is room temperature; and the reaction time is 1 hour. The binaphthyl derivative (B) represented by the formula (5) is (S)-8,8'-bis(trifluoromethanesulfonyloxy)-4,4',6,6'-tetraiodo-2,2'-dimethoxy-1,1'-binaphthyl.

(5)

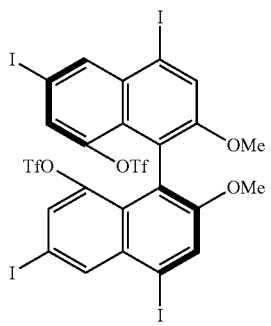

When either of the two precursor derivatives (A) represented by the formulae (2) and (3), the conditions optimal for obtaining a binaphthyl derivative (B) having six TfO groups as the substituents $Z^1$ and $Z^4$ and represented, for example, by formula (6) below and/or a binaphthyl derivative (B) having seven TfO groups as the substituents $Z^1$ and $Z^4$ and represented, for example, by formula (7) below are, for example, as follows: DIH is used as the iodinating agent in an amount of 10 equivalents per equivalent of the precursor derivative (A); TfOH is used as the organic acid in an amount of 20 equivalents per equivalent of the precursor derivative (A); dichloromethane is used as the solvent; the reaction temperature is room temperature; and the reaction time is 1 hour. The binaphthyl derivative (B) represented by the formula (6) is (S)-5,5',6,6',8,8'-hexakis(trifluoromethanesulfonyloxy)-4,4'-diiodo-2,2'-dimethoxy-1,1'-binaphthyl, and the binaphthyl derivative (B) represented by the formula (7) is (S)-4,5,5',6,6',8,8'-heptakis(trifluoromethanesulfonyloxy)-4'-iodo-2,2'-dimethoxy-1,1'-binaphthyl.

(6)

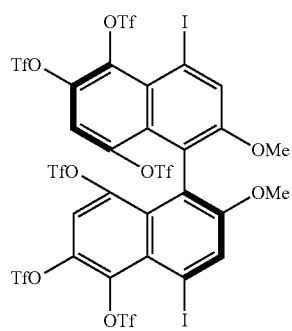

(7)

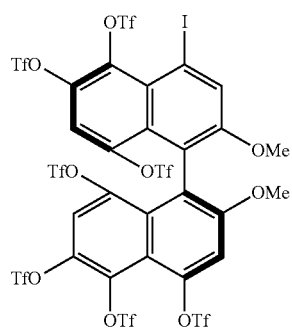

In the first production method, the amount of the iodinating or brominating agent to be added to the reaction system differs depending on the molecular structure of the binaphthyl derivative (B) to be obtained (the types of the substituents $Z^1$ and $Z^4$ and the positions of the binaphthyl skeleton at which these substituents are to be introduced), the type of the iodinating or brominating agent, the reaction temperature, and other reaction conditions. When the iodinating agent is DIH, the amount of the iodinating agent can be, for example, 2 equivalents or more and 60 equivalents or less, 2 equivalents or more and 50 equivalents or less, 3 equivalents or more and 30 equivalents or less, or more than 5 equivalents and 50 equivalents or less, per equivalent of the precursor derivative (A). When the iodinating agent is NIS, the same result as obtained by the use of DIH can be achieved by using NIS in an amount of 2 to 8 times the equivalents indicated for DIH.

In the first production method, the amount of the organic acid to be added to the reaction system differs depending on the molecular structure of the binaphthyl derivative (B) to be obtained, the type of the organic acid, the reaction temperature, and other reaction conditions. The amount of the organic acid can be, for example, 2 equivalents or more and 120 equivalents or less, 5 equivalents or more and 60 equivalents or less, or more than 10 equivalents and 100 equivalents or less, per equivalent of the precursor derivative (A).

The reaction temperature in the first production method is, for example, −30 to 80° C. and can be 0 to 60° C. or 20 to 30° C.

The reaction time in the first production method is, for example, 0.5 to 24 hours and can be 1 to 15 hours or 1 to 3 hours.

Examples of the effects provided depending on the positions at which the substituents $Z^1$ and $Z^4$ are introduced in the binaphthyl derivative (B) will be described hereinafter. The presence of the substituent $Z^1$ at the 8-position and/or 8'-position of the binaphthyl skeleton allows, for example, control of the dihedral angle of the binaphthyl derivative (B). The presence of substituents (e.g., the electron-donating groups $Z^2$; the electron-donating groups $Z^2$ of the precursor derivative (A) can be left intact, can be converted to other substituents through the further reaction as mentioned above, or can be removed) at the 2-position and/or 2'-position of the binaphthyl skeleton enables, for example, the use of the axial chirality of the binaphthyl skeleton. The presence of substituents at the 3-position and/or 3'-position of the binaphthyl skeleton provides, for example, an improvement in the chiral environment of the binaphthyl derivative (B). The presence of substituents at the 6-position and/or 6'-position of the binaphthyl skeleton provides, for example, an increase in the flexibility in further derivation from the binaphthyl derivative (B). Introduction of a bulky substituent such as a trimethylsilyl group or t-butyl group at the 4-position and/or 4'-position of the binaphthyl skeleton also provides an improvement in the chiral environment of the binaphthyl derivative (B), just as does the introduction of substituents at the 3-position and/or 3'-position. Additionally, when linear alkynyl groups (such as propargyl groups) are introduced at the 4-position and/or 4'-position of the binaphthyl skeleton and the resulting derivative is immobilized on a support such as silica gel, stable complex formation becomes possible even in an inhomogeneous system because coordination to a metal at the 2-position and 2'-position is not affected by the immobilization by virtue of the fact that the linear alkynyl groups can lie on an extension of the chiral axis.

Examples of the effects provided depending on the types of the substituents $Z^1$ and $Z^4$ in the binaphthyl derivative (B) will be described hereinafter.

The substituents $Z^1$ and $Z^4$ can, depending on their types, act as active sites for a further reaction of the binaphthyl derivative (B). This means that the substituents $Z^1$ and $Z^4$ offer the possibility of further derivation from the binaphthyl derivative (B). For example, when the substituents $Z^1$ and $Z^4$ are each an organic acid group (in particular a TfO group), an iodo group, or a bromo group, the substituents $Z^1$ and $Z^4$ exhibit high reactivity in cross-coupling reactions. This means that, from binaphthyl derivatives (B) having such substituents $Z^1$ and $Z^4$, a wide variety of compounds including physiological active substances and active pharmaceutical ingredients and precursors of such compounds can be synthesized through cross-coupling reactions. The controllability of the position of the binaphthyl skeleton at which the substituent $Z^4$ is to be introduced contributes to the wide variety of compounds that can be obtained by further derivation. Examples of the cross-coupling reactions include Suzuki-Miyaura coupling, Tamao coupling, Negishi coupling, Kosugi-Migita-Stille coupling, Sonogashira coupling, Hiyama coupling, Mizoroki-Heck reaction, and Denmark coupling. It should be understood that the same applies to other cross-coupling reactions. The iodo group has the highest reactivity in the cross-coupling reactions, followed by the TfO group and then the bromo group.

When the substituents $Z^1$ and $Z^4$ are organic acid groups, the substituents $Z^1$ and $Z^4$ can be converted to hydroxy groups relatively easily by hydrolysis. This means that a polyphenol having a binaphthyl skeleton can be obtained. From the polyphenol, for example, a ketone structure, a quinone structure, or an ether structure can be derived. Examples of further derivatives having a quinone structure include those represented by formulae (8) and (9) below, and an example of further derivatives having an ether structure is that represented by formula (10) below. The compounds represented by the formulae (8) to (10) are merely examples of further derivatives obtained from binaphthyl derivatives (B).

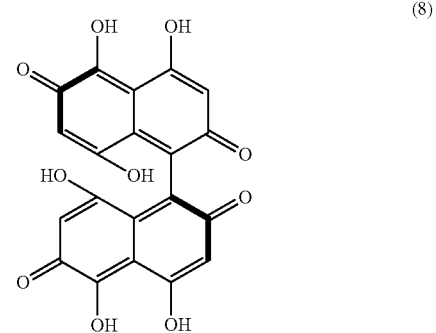

(8)

-continued

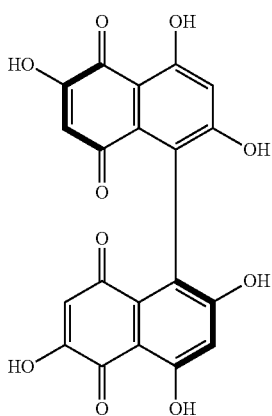
(9)

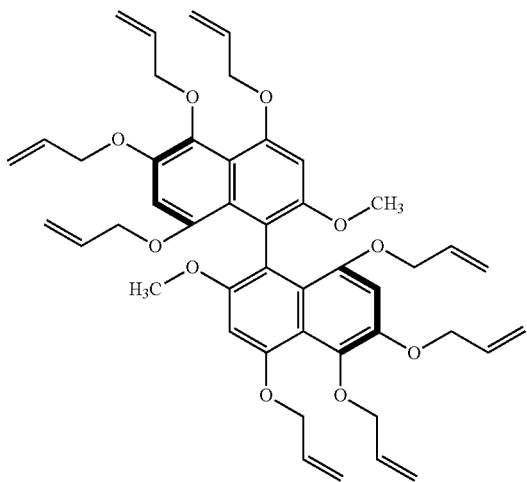
(10)

An example of a reaction for forming a further derivative having a quinone structure from a binaphthyl derivative (B) having organic acid groups as the substituents $Z^1$ and $Z^4$ is shown by the following formula (11).

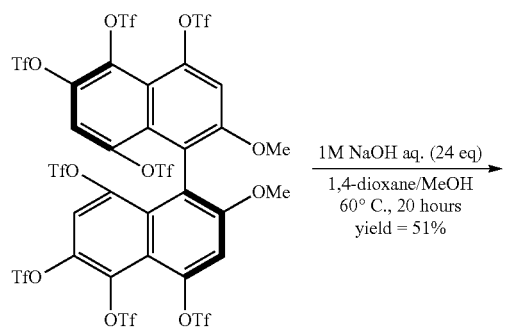
(11)

-continued

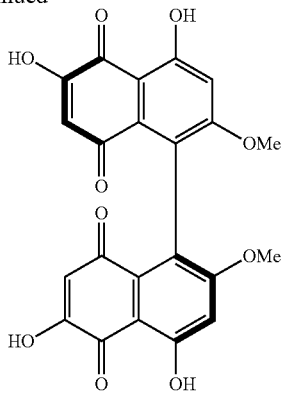

The methoxy groups at the 2-position and 2'-position of the binaphthyl skeleton of the compound of the formula (11) (the compound shown on the right side of the formula (11)) can be converted to hydroxy groups relatively easily; namely, the compound of the formula (9) can be derived from the compound of the formula (11). The compounds of the formula (9) and formula (11) can act both as an electron acceptor (on the basis of the quinone structure) and as an electron donor (due to the hydroxyl groups of the polyphenol). These compounds are chiral (optically active) and can act as a chiral electron acceptor or as a chiral electron donor.

Figure 5A:
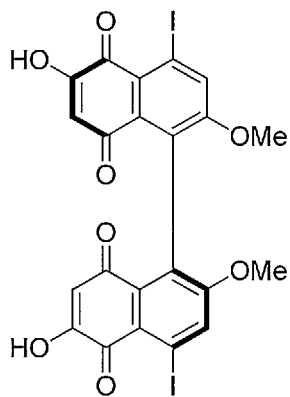
FIG. 5A shows examples of further derivatives formed from 1,1'-binaphthyl derivatives that can be formed by the production method of the present invention.
Figure 5A:
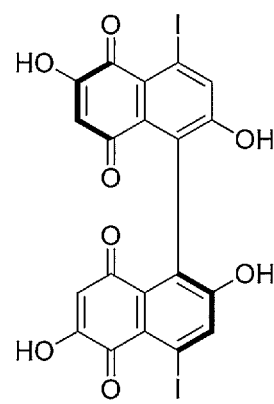
Figure 5A:
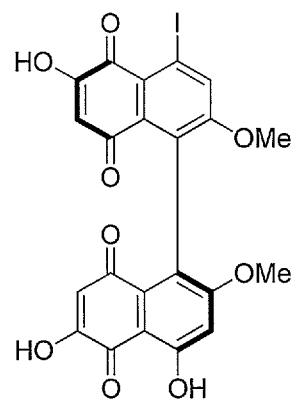
Figure 5A:
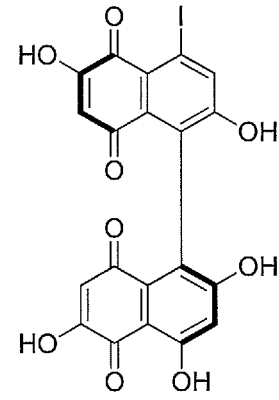
Figure 5A:
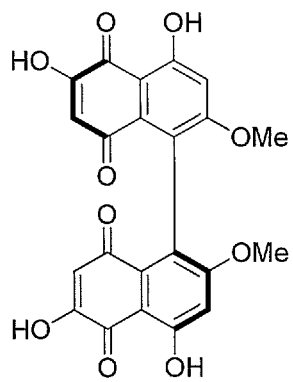
Figure 5A:
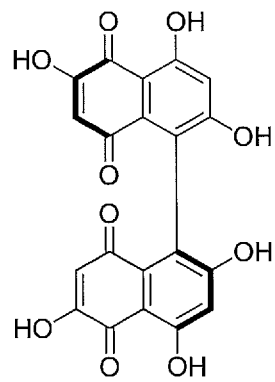
Figure 5A:
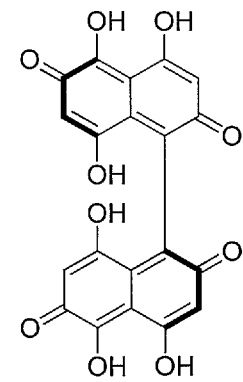
Figure 5B:
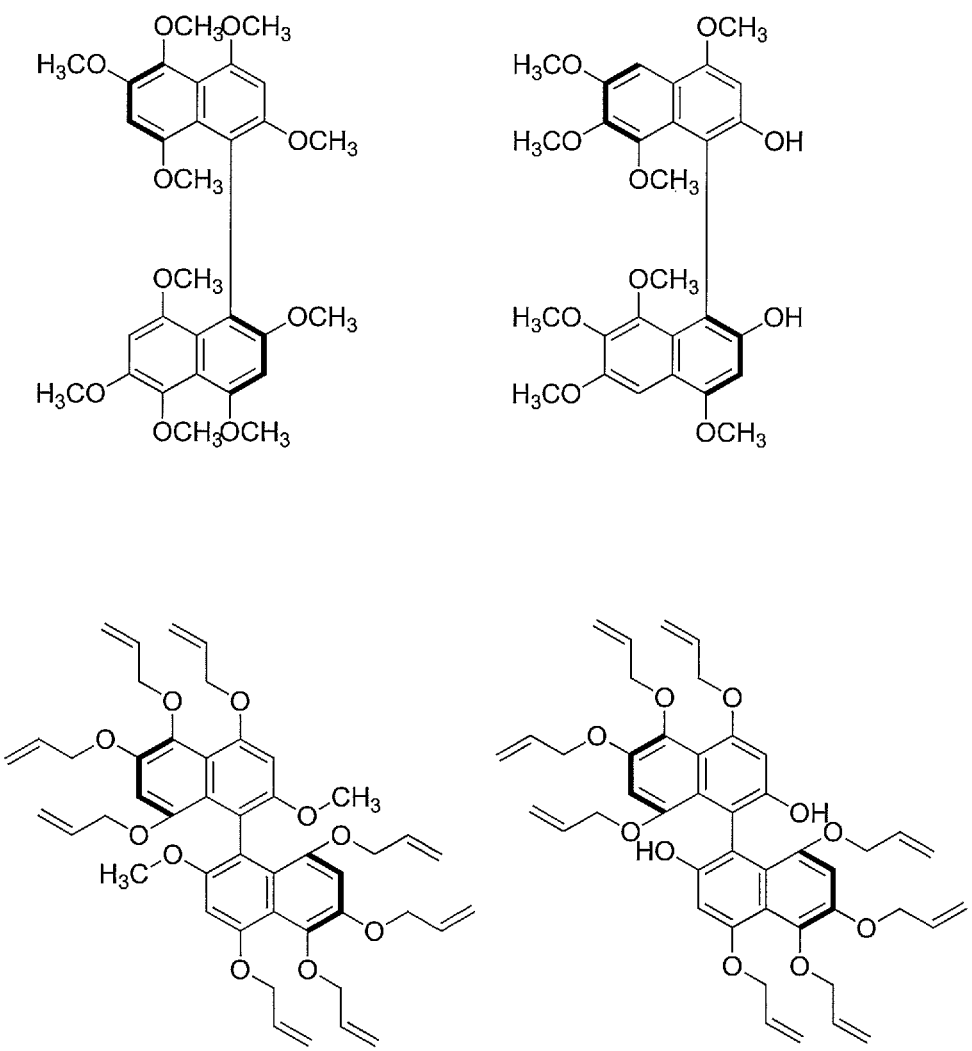
FIG. 5B shows other examples of further derivatives formed from 1,1'-binaphthyl derivatives that can be formed by the production method of the present invention.

Examples of further derivatives having a quinone structure or another structure are shown in FIGS. 5A and 5B.

From these further derivatives, still other derivatives may be formed through a further reaction. For example, the compounds of the formula (9) and formula (11) have a basic skeleton of coenzymes such as ubiquinones and vitamin K. Thus, the compounds of the formula (9) and formula (11) can be developed into these coenzymes. The ubiquinones include coenzyme Q10. Additionally, for example, the compounds of the formula (9) and formula (11), which are derivatives having a quinone structure, may be subjected to Diels-Alder reaction to achieve further derivation. An example of the further derivation by Diels-Alder reaction is synthesis of skyrin. Skyrin serves, for example, as an anti-diabetic drug or as a suppressing drug against pancreatic cancer. The molecular structure of skyrin is represented by formula (12) below, and the molecular structure of an intermediate that may be produced during the process of derivation of skyrin is represented by formula (13) below. The compounds of the formula (9) and formula (11) can be intermediates for chemical synthesis of compounds having a bis-anthraquinone structure (many such compounds exist as natural products).

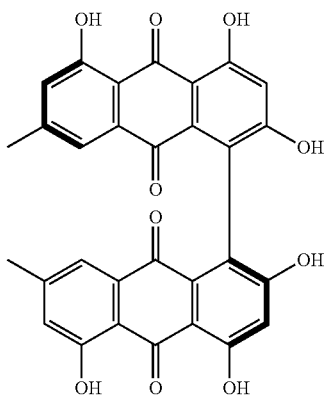
(12)

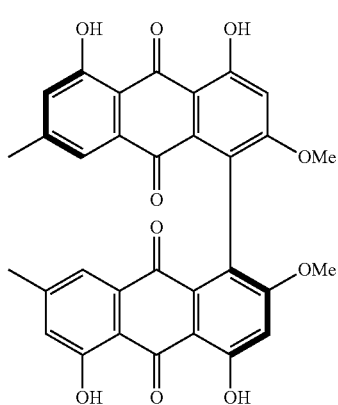

(13)

As described above, binaphthyl derivatives (B) can be converted to a very wide variety of compounds through further reactions. The compounds to which binaphthyl derivatives (B) can be converted are not limited to 1,1'-binaphthyl derivatives and may be compounds such as 1,1'-bianthracenyl derivatives represented by the formulae (12) and (13) which have a skeleton other than a binaphthyl skeleton. The first production method is very advantageous and useful in that such binaphthyl derivatives (B) can be formed. The first production method will be more advantageous when optical activity can be maintained before and after the reaction for introduction of the substituents $Z^1$ and $Z^4$, namely when the (R)-form or (S)-form can be maintained before the reaction.

An example of derivation of a further 1,1'-binaphthyl derivative from a binaphthyl derivative (B) will be described hereinafter as a third production method of the present disclosure. The third production method is a method including allowing a 1,1'-binaphthyl derivative represented by formula (1) below to undergo a reaction involving at least one group selected from $Y^1$, $Y^2$, —$OR^1$, —$OR^2$, and at least one X, such as a reaction in which the at least one group acts as a reaction site, so as to obtain a 1,1'-binaphthyl derivative that is a result of the reaction and different from the derivative represented by the formula (1). In the formula (1), X is an iodo group or a bromo group, $R^1$ and $R^2$ are each independently a hydrogen atom, an alkyl group having 1 to 50 carbon atoms, an allyl group, a benzyl group, a trifluoromethanesulfonyl group, a silyl group, or a protecting group for a hydroxy group, $Y^1$ and $Y^2$ are each independently a hydroxy group or an organic acid group containing an oxygen atom directly bonded to the binaphthyl skeleton of the derivative.

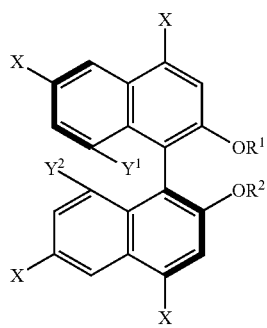

(1)

Examples of the reaction in the third production method include those described as examples of the further reaction of (further derivation from) a binaphthyl derivative (B) formed by the first production method. More specific examples include at least one reaction selected from substitution reactions and hydrolysis reactions. The substitution reactions include cross-coupling reactions.

Examples of the 1,1'-binaphthyl derivative represented by the formula (1) are compounds in which X is an iodo group, $R^1$ and $R^2$ are hydrogen atoms, methyl groups, or trifluoromethanesulfonyl groups, and $Y^1$ and $Y^2$ are each independently the organic acid group as defined above or a hydroxy group. As is apparent from the foregoing description, it should be understood that X, $R^1$, $R^2$, $Y^1$, and $Y^2$ are not limited to these groups. Possible groups are the same as those for the substituents $Z^1$ and $Z^4$.

The third production method is merely an example of derivation for forming a further 1,1'-binaphthyl derivative from a binaphthyl derivative (B), and derivation from the other binaphthyl derivatives (B) mentioned above is also possible.

The first production method is capable of forming a binaphthyl derivative (B) that exhibits at lease one effect selected from the various effects described above (including enabling implementation of the third production method).

The precursor derivative (A) used as a starting material in the first production method is not limited as long as the requirements described above are met. The precursor derivative (A) may have a substituent $Z^3$ or may not have any substituent $Z^3$. The substituent $Z^3$ is, for example, but not limited to, at least one selected from an iodo group and a bromo group. The fact that the precursor derivative (A) may have an iodo group and/or bromo group as the substituent $Z^3$ means that the first production method can be started from a halogenated binaphthyl.

The first production method can be carried out using a binaphthyl derivative (B) as the precursor derivative (A) as long as any substituent is present at neither the 8-position nor the 8'-position of the binaphthyl skeleton of the binaphthyl derivative (B). The substituent $Z^3$ may be the same as the substituent $Z^4$.

The formation of a binaphthyl derivative (B) is not limited to formation from a precursor derivative (A) which itself is a compound having a binaphthyl skeleton. A precursor derivative (A) and/or binaphthyl derivative (B) can be formed from a naphthalene derivative. This is based on the fact that mixing of a naphthalene derivative, an organic acid, and an iodinating or brominating agent allows a coupling reaction (homocoupling reaction) of the naphthalene derivative to take place to form a 1,1'-binaphthyl derivative. Such a coupling reaction of a naphthalene derivative has also been discovered by the present inventors for the first time. After the coupling reaction, the organic acid and the iodinating or brominating agent present during the coupling reaction can act on the formed 1,1'-binaphthyl derivative as in the first production method to introduce a substituent at the 8-position and/or 8'-position of the binaphthyl skeleton.

That is, the second production method of the present disclosure is a method including mixing a naphthalene derivative (C), an organic acid, and an iodinating or brominating agent to allow a coupling reaction of the naphthalene derivative (C) so as to obtain a 1,1'-binaphthyl derivative (D), the naphthalene derivative (C) having a naphthalene skeleton and having a substituent $Z^5$ at the 2-position of the naphthalene skeleton, the 1,1'-binaphthyl derivative (D) having a 1,1'-binaphthyl skeleton and having a substituent $Z^6$ at the 2-position of the 1,1'-binaphthyl skeleton and at the 2'-position of the 1,1'-binaphthyl skeleton. The binaphthyl derivative (D) formed by the second production method may be a precursor derivative (A) or binaphthyl derivative (B) as described above. The substituent $Z^5$ may be the substituent $Z^2$. The substituent $Z^5$ is, for example, an electron-donating group containing an oxygen atom directly bonded to the naphthalene skeleton. More specifically, the substituent $Z^5$ is, for example, —OR. R may be a hydrogen atom, an alkyl group having 1 to 50 carbon atoms, an allyl group, a benzyl group, a trifluoromethanesulfonyl group, a silyl group, or a protecting group for a hydroxy group and may be a hydrogen atom, a methyl group, or a trifluoromethanesulfonyl group. The substituent $Z^6$ may be the substituent $Z^5$ or a group resulting from conversion of the substituent $Z^5$ (e.g., a group resulting from conversion of the substituent $Z^2$ described above).

In view of the fact that a binaphthyl derivative (D) formed by the second production method may be a binaphthyl derivative (B), a binaphthyl derivative (D) further having a substituent introduced at the 8-position and/or 8'-position of the binaphthyl skeleton may be obtained in the second production method.

The features of the binaphthyl derivative (D) formed by the second production method, such as the position of the binaphthyl skeleton at which a substituent is introduced and the type of the substituent, can be controlled by controlling the reaction conditions as in the first production method.

The binaphthyl derivative (D) formed by the second production method is typically in the form of a racemate, and this racemate can be separated by chiral resolution into (R)- and (S)-isomers to collect either of the isomers individually.

The method for the chiral resolution is not limited, and a known method can be employed.

Examples of the reaction conditions will be described hereinafter. When a naphthalene derivative (C) represented by formula (14) below is used, the conditions optimal for obtaining, for example, a binaphthyl derivative (D) represented by formula (15) below are, for example, as follows: DIH is used as the iodinating agent in an amount of 25 equivalents per equivalent of the naphthalene derivative (C); TfOH is used as the organic acid in an amount of 50 equivalents per equivalent of the naphthalene derivative (C); dichloromethane is used as the solvent; the reaction temperature is room temperature; and the reaction time is 12 hours.

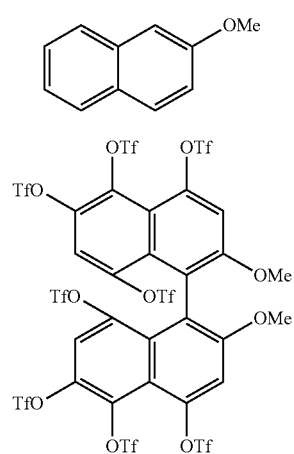

Although the compounds given as specific examples for illustrating the production methods of the present disclosure are generally (S)-isomers, the same explanation applies to (R)-isomers. With any of the production methods of the present disclosure other than the method (second production method) involving a coupling reaction starting from a naphthalene derivative, there is a possibility that the axial chirality of the starting material can be maintained. Although a coupling reaction starting from a naphthalene derivative gives a binaphthyl derivative in the form of a racemate which is a mixture of (S)-isomer and (R)-isomer, the (S)-isomer or (R)-isomer can be obtained individually through chiral resolution.

The applications of binaphthyl derivatives (B) and binaphthyl derivatives (D) obtained by the production methods of the present disclosure are not limited, and various applications are possible depending on the molecular structures of the derivatives. Exemplary applications, including those previously mentioned, will be described hereinafter.

Use as Precursors for Various Chemical Reactions

The binaphthyl derivatives (B) and (D) can be used as precursor compounds for various chemical reactions. Examples of the reactions include hydrolysis reactions, substitution reactions, and addition reactions, and more specific examples include cross-coupling reactions, Diels-Alder reactions, oxidation reactions, reduction reactions, and cyclization reactions.

Use as Precursors of Various Compounds

The binaphthyl derivatives (B) and (D) can be used as precursor compounds of various compounds. Examples of the compounds include coenzymes (vitamins and ubiquinones) and active pharmaceutical ingredients such as skyrin.

Use as Optically Active Materials

The binaphthyl derivatives (B) and (D) can, based on their axial chirality, be used as optically active materials. Thus, for example, the derivatives can be used for catalytic asymmetric synthesis reactions and also for construction of a chiral molecular recognition site on the surface of a substrate. The substrate is not particularly limited and may be, for example, a column composed of silica gel or organic-inorganic hybrid gel. The use of a binaphthyl derivative (B) or (D) for modification of the surface of the column results in, for example, an unconventional chiral separation column.

Axially chiral compounds exhibit circularly polarized emission with high efficiency. Thus, when a binaphthyl derivative (B) or (D) is used as an optically active material and supported on the surface of a substrate, an optical member such as an organic circularly polarized emission film can be obtained. Examples of the substrate include: glass; polyesters such as PET; acrylics; polyolefins (including cyclic olefin polymers) such as polyethylene and polypropylene; polycarbonates; and celluloses (including cellulose nanofiber) such as triacetyl cellulose.

Other possible applications of the derivatives include use as chiral catalysts and use as bioreagents based on the ability to selectively bind to a receptor having a chiral environment in vivo.

Use as Polyphenols (when Two or More Hydroxy Groups are Bonded as Substituents to the Binaphthyl Skeleton)

The binaphthyl derivatives (B) and (D) in the form of polyphenols can be used, for example, for removal of active oxygen. The derivatives can react with polymethylhydrosiloxane (PMHS) to form a PMHS complex, thus enabling modification of the surface of a substrate by means of hydrosilyl groups of the complex. The substrate is not limited and may be, for example, any of the materials mentioned above, a metal, or a metal oxide. The form of the substrate is not limited, and the substrate may be in the form of, for example, a sheet, film, fiber (including nanofiber), or powder. Such use of the derivatives can be considered use as surface treatment agents.

[Binaphthyl Derivatives]

With the production methods of the present disclosure, for example, new binaphthyl derivatives (B) and (D) described hereinafter can be formed. For formation of the derivatives, the above-described methods for producing binaphthyl derivatives may be used or applied. Persons skilled in the art would understand how the above-described methods for producing binaphthyl derivatives should be used or applied.

1,1'-Binaphthyl Derivative Having Substituent $Z^7$ at 8-Position and/or 8'-Position of Binaphthyl Skeleton The substituent $Z^7$ may be a group containing an oxygen atom directly bonded to the binaphthyl skeleton, an aliphatic group having 1 to 50 carbon atoms, or an aryl group having 6 to 30 carbon atoms. When the substituent $Z^7$ is an aliphatic group, the effect of the present invention will be more significant if the aliphatic group has a number of carbon atoms such as two or more carbon atoms.

Additionally, the substituent $Z^7$ may be a group $P^1$ containing an oxygen atom directly bonded to the binaphthyl skeleton, and groups $P^2$ each containing an oxygen atom directly bonded to the skeleton may be present at three or more positions of the skeleton other than the position at which the group $P^1$ is present ($P^1$ and $P^2$ may be the same or different).

The substituent $Z^7$ is, for example, selected from: an organic acid group; a hydroxy group; an alkoxy group such as a methoxy or ethoxy group; an alkyl group such as a methyl or ethyl group; an aryl group such as a phenyl group, phenyl derivative group, or naphthyl group; an aralkyl group such as a benzyl group; a thioalkoxy group such as a methylthio group; a silyl group such as a trimethylsilyl or allylsilyl group; a group containing a phosphorus atom directly bonded to the skeleton, such as a triphenylphosphino or triphenylphosphinyl group; an amino group such as a dimethylamino or diphenylamino group; a bromo group; and a chloro group. The groups $P^1$ and $P^2$ are, for example, each independently an organic acid group, a hydroxy group, an alkoxy group such as a methoxy or ethoxy group, an amino group, a silyl group, a phosphinyl group, or a phosphonyl group. When the groups $P^1$ and $P^2$ are aliphatic groups, the effect of the present invention will be more significant if the aliphatic groups have a number of carbon atoms such as two or more carbon atoms.

[Methods for Producing Perylene and Perylene Derivatives]

The present inventors have further found that a perylene derivative can be obtained by controlling the reaction conditions in the first production method, in particular by mixing a precursor derivative (A), an organic acid, and an iodinating or brominating agent as in the first production method and controlling the reaction conditions in the reaction system formed as a result of the mixing.

That is, another production method of the present disclosure (fourth production method) is a method for producing perylene derivatives, including mixing a 1,1'-binaphthyl precursor derivative (A), an organic acid, and an iodinating or brominating agent to obtain a perylene derivative, the 1,1'-binaphthyl precursor derivative (A) having a 1,1'-binaphthyl skeleton and having an electron-donating group $Z^2$ at the 2-position of the skeleton and at the 2'-position of the skeleton, the electron-donating group $Z^2$ containing an oxygen atom directly bonded to the skeleton. All of the substituents bonded to the perylene skeleton of the resulting perylene derivative can be removed to give perylene.

In the fourth production method, a reaction system containing a precursor derivative (A), an organic acid, and an iodinating or brominating agent is employed to cause a reaction for introduction of a bond (single bond) connecting the 8-position and 8'-position of the binaphthyl skeleton of the precursor derivative (A). This introduction reaction converts the binaphthyl skeleton to a perylene skeleton.

The first production method and the fourth production method are similar in that a precursor derivative (A), an organic acid, and an iodinating or brominating agent are mixed to introduce a new bond at the 8-position and/or 8'-position of the binaphthyl skeleton of the precursor derivative (A). The new bond is other than a bond with a hydrogen atom. Binaphthyl derivatives (B) obtained by the first production method and perylene derivatives obtained by the fourth production method are similar in that they are polycyclic aromatic compounds having a polycyclic aromatic structure derived from the precursor derivative (A) (more specifically, derived from the binaphthyl skeleton of the precursor derivative (A)). The present disclosure includes a method (fifth production method) for producing a polycyclic aromatic compound, including the step of mixing a precursor derivative (A), an organic acid, and an iodinating or brominating agent to introduce a bond with an atom other than a hydrogen atom at the 8-position and/or 8'-position of the binaphthyl skeleton of the precursor derivative (A), wherein the polycyclic aromatic compound has a polycyclic aromatic structure derived from the precursor derivative (A).

In the fifth production method, for example, the atom other than a hydrogen atom at the 8-position of the binaphthyl skeleton of the precursor derivative (A) and the atom other than a hydrogen atom at the 8'-position of binaphthyl skeleton of the precursor derivative (A) are each independently a carbon atom or an oxygen atom.

In the fifth production method, a substituent $Z^1$ can be introduced as the bond at the 8-position and/or 8'-position of the binaphthyl skeleton of the precursor derivative (A). More specifically, in the fifth production method, a substituent $Z^1$ may be introduced as the bond at the 8-position and/or 8'-position of the binaphthyl skeleton to obtain as the polycyclic aromatic compound a binaphthyl derivative (B) having the substituent $Z^1$ introduced at the 8-position and/or 8'-position of the binaphthyl skeleton. The fifth production method in this case corresponds to the first production method. The substituent $Z^1$ is as described above in the description of the first production method.

In the fifth production method, the bond introduced can be a bond (single bond) connecting the 8-position and 8'-position of the binaphthyl skeleton of the precursor derivative (A). More specifically, in the fifth production method, a bond (single bond) connecting the 8-position and 8'-position of the binaphthyl skeleton may be introduced to obtain a perylene derivative (or perylene resulting from removing all of the substituents bonded to the perylene skeleton of the perylene derivative) as the polycyclic aromatic compound. The fifth production method in this case corresponds to the fourth production method.

With the fifth production method, for example, a 1,1'-binaphthyl derivative (B), perylene, or a perylene derivative can be obtained as the polycyclic aromatic compound.

The precursor derivative (A), organic acid, iodinating agent, and brominating agent in the fourth and fifth production methods are as described above in the description of the first production method.

The reaction system in the fourth production method is not limited to a specific system as long as mixing of the precursor derivative (A), the organic acid, and the iodinating or brominating agent induces a reaction for introduction of a single bond connecting the 8-position and 8'-position of the binaphthyl skeleton. The reaction system in the fifth production method is not limited to a specific system as long as mixing of the precursor derivative (A), the organic acid, and the iodinating or brominating agent induces a reaction for introduction of a bond with an atom other than a hydrogen atom at the 8-position and 8'-position of the binaphthyl skeleton. The reaction systems in the fourth and fifth production methods may be the same as the reaction system in the first production method.

In the fifth production method, whether a substituent $Z^1$ is introduced at the 8-position and/or 8'-position of the binaphthyl skeleton of the precursor derivative (A) (the fifth production method in this case corresponds to the first production method) or a single bond connecting the 8-position and 8'-position of the binaphthyl skeleton of the precursor derivative (A) is introduced (the fifth production method in this case corresponds to the fourth production method) can be controlled depending on the reaction conditions. Examples of the reaction conditions include the type and amount (e.g., equivalents per equivalent of the precursor derivative (A)) of the organic acid used, the type and amount of the iodinating or brominating agent used, the reaction temperature, the reaction time, and the molecular structure of the precursor derivative (A) (e.g., the type of the electron-donating groups $Z^2$ bonded at the 2-position and 2'-position of the binaphthyl skeleton of the precursor derivative (A)).

In the fourth production method, the electron-donating group $Z^2$ of the precursor derivative (A) is, for example, an organic acid group and may be a trifluoromethanesulfonyl group.

In the fourth production method and the fifth production method that gives a perylene derivative, the amount of the iodinating or brominating agent added to the reaction system differs depending on the molecular structure of the precursor derivative (A), the molecular structure of the perylene derivative to be obtained (e.g., the type of the substituents $Z^4$ bonded to the perylene derivative and the positions of the perylene skeleton at which the substituents are introduced), the type of the iodinating or brominating agent, the reaction temperature, and other reaction conditions. When the iodinating agent is DIH, the amount of the iodinating agent can be, for example, 2 equivalents or more and 60 equivalents or less, 3 equivalents or more and 30 equivalents or less, or 10 equivalents or more and 20 equivalents or less per equivalent of the precursor derivative (A). When the iodinating agent is NIS, the same result as obtained by the use of DIH can be achieved by using NIS in an amount of 2 to 8 times the equivalents indicated for DIH.

In the fourth production method and the fifth production method that gives a perylene derivative, the amount of the organic acid added to the reaction system differs depending on the molecular structure of the precursor derivative (A), the molecular structure of the perylene derivative to be obtained, the type of the organic acid, the reaction temperature, and other reaction conditions. The amount of the organic acid can be, for example, 3 equivalents or more and 120 equivalents or less, 5 equivalents or more and 60 equivalents or less, or 10 equivalents or more and 40 equivalents or less per equivalent of the precursor derivative (A).

In the fourth production method and the fifth production method that gives a perylene derivative, the reaction temperature is, for example, −78 to 100° C. and can be −30 to 60° C. or −10 to 30° C.

In the fourth production method and the fifth production method that gives a perylene derivative, the reaction time is, for example, several seconds to 48 hours and can be 10 seconds to 24 hours, or 10 seconds to 18 hours. Depending on the system, a very short time on the order of seconds is sufficient for formation of a perylene derivative from the precursor derivative (A), as demonstrated by examples described later.

The reaction conditions in the fifth production method that gives a binaphthyl derivative (B) are as described above for the first production method.

In the fourth production method and the fifth production method, a substituent $Z^4$ can be further introduced at a position other than the 8-position and/or 8'-position of the binaphthyl skeleton of the precursor derivative (A) by controlling the reaction conditions. The substituent $Z^4$ is as described above for the first production method.

The same description as given above for the first production method applies to the fifth production method that gives a binaphthyl derivative (B). That is, a binaphthyl derivative (B) having a substituent $Z^4$ introduced at at least one position selected from the 4-position, 4'-position, 5-position, 5'-position, 6-position, and 6'-position of the binaphthyl skeleton can be obtained as the polycyclic aromatic compound.

In the fourth production method and the fifth production method that gives a perylene derivative, the position of the perylene skeleton at which the substituent $Z^4$ is to be introduced can be controlled by controlling the reaction conditions. In general, as the reaction conditions become harsher, the introduction of the substituent $Z^4$ comes to occur first at the 6-position and/or 6'-position of the binaphthyl skeleton of the precursor derivative (A), then at the 5-position and/or 5'-position and even at the 4-position and/or 4'-position. This means that making the reaction conditions harsher generally results in a perylene derivative having the substituents $Z^4$ introduced at the 5-position and/or 8-position, the 4-position and/or 9-position, and even the 2-position and/or 10 position of the perylene skeleton. That is, in the fourth production method and the fifth production method that gives a perylene derivative, a perylene derivative having the substituent $Z^4$ introduced at at least one position selected from the 3-position, 4-position, 5-position, 8-position, 9-position, and 10-position of the perylene skeleton may be obtained (as the polycyclic aromatic compound).

In the fourth production method and the fifth production method that gives a perylene derivative, the type of the substituent $Z^4$ and the position of the perylene skeleton at which the substituent $Z^4$ is introduced can be controlled by controlling the above reaction conditions as in the first production method. This means that, for example, when the precursor derivative (A) has a substituent at a position other than the 2-position and 2'-position (the precursor derivative (A) has a substituent $Z^3$) and the substituent $Z^3$ is an iodo or bromo group, the iodo or bromo group can be substituted by an organic acid group or a hydroxy group (ipso substitution) by controlling the reaction conditions. When the substituent $Z^4$ to be introduced into the binaphthyl skeleton of the precursor derivative (A) varies from an iodo or bromo group to an organic acid group with increasing harshness of the reaction conditions, the ipso substitution is presumed to take place as a reaction mechanism in which the iodo or bromo group having been introduced into the skeleton is substituted by the organic acid group.

As seen from the foregoing description, the fourth production method and the fifth production method that gives a perylene derivative are capable of forming a perylene derivative having a plurality of organic acid groups, in particular TfO groups, introduced as the substituents $Z^4$ into the perylene skeleton. These methods are also capable of forming a perylene derivative having a plurality of hydroxy groups introduced as the substituents $Z^4$ into the perylene skeleton. An exemplary perylene derivative is one that has organic acid groups such as TfO groups and/or hydroxy groups at all the positions of the perylene skeleton. Such a perylene derivative may be a perylene derivative having organic acid groups at all the positions or may be a perylene derivative having hydroxy groups at all the positions.

The substituent $Z^4$ can, depending on its type, act as an active site for a further reaction of the perylene derivative. This means that the substituent $Z^4$ offers the possibility of further derivation from the perylene derivative. For example, when the substituent $Z^4$ is an organic acid group (in particular a TfO group), an iodo group, or a bromo group, the substituent $Z^4$ exhibits high reactivity in cross-coupling reactions. This means that, from perylene derivatives having such a substituent $Z^4$, a wide variety of compounds including physiological active substances and active pharmaceutical ingredients and precursors of such compounds can be synthesized through cross-coupling reactions. The controllability of the position of the perylene skeleton at which the substituent $Z^4$ is to be introduced contributes to the wide variety of compounds that can be obtained by further derivation. Specific examples of the cross-coupling reactions are those mentioned above for the first production method. The iodo group has the highest reactivity in the cross-coupling reactions, followed by the TfO group and then the bromo group.

When the substituent $Z^4$ is an organic acid group, the substituent $Z^4$ can be converted to a hydroxy group relatively easily by hydrolysis. This means that a polyphenol having a perylene skeleton can be obtained. From the polyphenol, for example, a ketone structure, a quinone structure, or an ether structure can be derived.

These further derivatives may be allowed to undergo further reactions to form other derivatives.

Thus, the perylene derivatives can be converted to a very wide variety of compounds through further reactions. The compounds to which the perylene derivatives can be converted may be compounds having a skeleton other than the perylene skeleton.

As is apparent from the foregoing description, the fourth production method or the fifth production method that gives a perylene derivative can be used to form a perylene derivative from a binaphthyl derivative (B) such as a binaphthyl derivative (B) obtained by the first production method. The fifth production method that gives a binaphthyl derivative can be used to further derive a 1,1'-binaphthyl derivative from a binaphthyl derivative (B) such as a binaphthyl derivative (B) obtained by the first production method.

It has been stated above that a precursor derivative (A) and/or a binaphthyl derivative (B) can be formed from a naphthalene derivative (second production method). When a 1,1'-binaphthyl derivative is formed by a coupling reaction of a naphthalene derivative, there is a possibility that the organic acid and the iodinating or brominating agent present during the coupling reaction acts on the 1,1'-binaphthyl derivative to give a perylene derivative as in the fourth production method and fifth production method. The present disclosure includes a method (sixth method) for producing a polycyclic aromatic compound, including the step of mixing a naphthalene derivative (C), an organic acid, and an iodinating or brominating agent to allow a coupling reaction of the derivative (C) to take place to form a 1,1'-binaphthyl derivative (D), the naphthalene derivative (C) having a naphthalene skeleton and having a substituent $Z^5$ at the 2-position of the naphthalene skeleton, the 1,1'-binaphthyl derivative (D) having a 1,1'-binaphthyl skeleton and having a substituent $Z^6$ at the 2-position of the 1,1'-binaphthyl skeleton and at the 2'-position of the 1,1'-binaphthyl skeleton, wherein the polycyclic aromatic compound has a polycyclic aromatic structure derived from the 1,1'-binaphthyl skeleton. The polycyclic aromatic compound is, for example, a 1,1'-binaphthyl derivative, perylene, or a perylene derivative.

The above step in the sixth production method is as described above for the second production method.

In the sixth production method, the substituent $Z^6$ may be an electron-donating group containing an oxygen atom directly bonded to the binaphthyl skeleton. When the substituent $Z^6$ is an electron-donating group containing an oxygen atom directly bonded to the binaphthyl skeleton, the sixth production method may further include the step of introducing a bond with an atom other than a hydrogen atom at the 8-position and/or 8'-position of the binaphthyl skeleton of the 1,1'-binaphthyl derivative (D) obtained by the coupling reaction of the naphthalene derivative (C). The bond is, for example, a bond (single bond) connecting the 8-position and 8'-position of the binaphthyl skeleton and, in this case, a perylene derivative (or perylene) can be obtained (as the polycyclic aromatic compound). The further step in the sixth production method and the perylene derivative are as described above for the fourth production method and fifth production method.

The applications of perylene derivatives obtained by the production methods of the present disclosure are not limited, and various applications are possible depending on the molecular structures of the derivatives. Exemplary applications will be described hereinafter.

Use as Precursors for Various Chemical Reactions

The perylene derivatives can be used as precursor compounds for various chemical reactions. Examples of the reactions include hydrolysis reactions, substituent reactions, and addition reactions, and more specific examples include cross-coupling reactions, Diels-Alder reactions, oxidation reactions, reduction reactions, and cyclization reactions.

Use as Precursors of Various Compounds

The perylene derivatives can be used as precursor compounds of various compounds.

Use as Polyphenols (when Two or More Hydroxy Groups are Bonded as Substituents to the Perylene Skeleton)

The perylene derivatives in the form of polyphenols can be used, for example, for removal of active oxygen. The derivatives can react with polymethylhydrosiloxane (PMHS) to form a PMHS complex, thus enabling modification of the surface of various substrates by means of hydrosilyl groups of the complex. The substrate to be surface-modified is not limited and may be, for example, any of the materials mentioned above for substrates, a metal, or a metal oxide. The form of the substrate is not limited, and the substrate may be in the form of, for example, a sheet, film, fiber (including nanofiber), or powder. Such use of the derivatives can be considered use as surface treatment agents.

Use as Optical Materials or Electronic Materials

In view of the light emission ability and/or electron transfer ability of the perylene skeleton, the use of the perylene derivatives as optical materials or electronic materials can be envisaged.

[Method for Producing Naphthalene Derivatives]

In a seventh production method of the present disclosure, a 1,1'-binaphthyl derivative and an organic acid are mixed to allow a decoupling (cleavage) reaction of the 1,1'-binaphthyl derivative to take place so as to obtain a naphthalene derivative, the 1,1'-binaphthyl derivative having a 1,1'-binaphthyl skeleton and having an electron-donating group $Z^2$ at the 2-position and/or 2'-position of the 1,1'-binaphthyl skeleton, the electron-donating group $Z^2$ containing an oxygen atom directly bonded to the 1,1'-binaphthyl skeleton, the naphthalene derivative having a naphthalene skeleton having a substituent. The binaphthyl derivative may be a binaphthyl precursor derivative (A) or binaphthyl derivative (B) as described above. The naphthalene derivative may be a naphthalene derivative (C) as described above.

In the naphthalene derivative formed by the seventh production method, a substituent of the binaphthyl derivative used as a starting material may be present as it is or only part of the substituent may be present. For example, the resulting naphthalene derivative may have the electron-donating group $Z^2$ at the 2-position of the naphthalene skeleton. A further reaction of the naphthalene derivative formed by the seventh production method may be allowed to take place to obtain a further derivative. This further reaction may continuously follow the decoupling reaction.

The reaction system may be a reaction system containing neither an iodinating agent nor a brominating agent. The organic acid used may be an organic acid as described above for the first production method.

The reaction system is not limited to a specific system as long as mixing of the binaphthyl derivative and the organic acid induces the decoupling reaction. Typically, the reaction system is a solution system. The solvent used in the solution system is preferably a solvent capable of dissolving the binaphthyl derivative, the organic acid, and the naphthalene derivative produced. Specific examples of the solvent used in the solution system include dichloromethane, chloroform, dichloroethane, chlorobenzene, toluene, tetrahydrofuran, and dioxane. Dichloromethane, dichloroethane, tetrahydrofuran, and dioxane are preferred from the viewpoint of the relative permittivity and the stability of a reaction intermediate.

The reaction system may, if necessary, contain a substance other than the binaphthyl derivative and the organic acid. The substance is, for example, an inorganic acid such as sulfuric acid. When the reaction system contains an inorganic acid, the amount of the organic acid to be used can be decreased depending on the type of the organic acid (e.g., trifluoromethanesulfonic acid).

Other examples of the substance include catalysts (including promoters) for controlling the reaction rate and radical scavengers.

In the seventh production method, the amount of the organic acid added to the reaction system differs depending on the type of the organic acid, the reaction temperature, and other reaction conditions. The amount of the organic acid can be, for example, 3 equivalents or more and 120 equivalents or less, 5 equivalents or more and 60 equivalents or less, or 10 equivalents or more and 50 equivalents or less per equivalent of the binaphthyl derivative.

The reaction temperature in the seventh production method is, for example, −78 to 120° C. and can be −30 to 80° C. or −10 to 30° C.

EXAMPLES

Hereinafter, the present invention will be described in more detail by Examples. The present invention is not limited to Examples given below.

Example 1

In Example 1, as shown in the following reaction formula, 8,8'-bis(trifluoromethanesulfonyloxy)-4,4',6,6'-tetraiodo-2,2'-dimethoxy-1,1-binaphthyl having trifluoromethanesulfonic acid groups ($CF_3SO_2$ groups; TfO groups) introduced at the 8-position and 8'-position was synthesized from (S)-4,4',6,6'-tetraiodo-2,2'-dimethoxy-1,1'-binaphthyl.

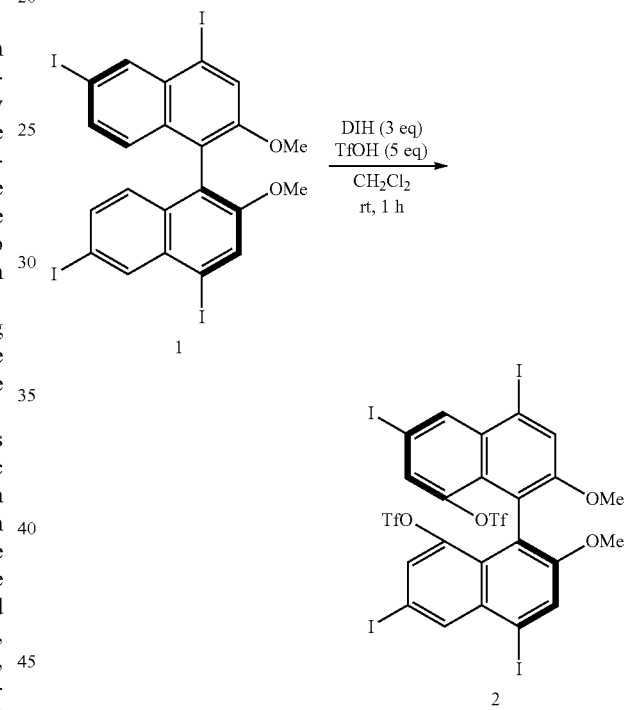

First, under air atmosphere, (S)-4,4',6,6'-tetraiodo-2,2'-dimethoxy-1,1'-binaphthyl (81.8 mg, 0.1 mmol) and DIH (manufactured by Nippoh Chemicals Co., Ltd.; 114 mg, 0.3 mmol) were dissolved in methylene chloride (5 mL), then trifluoromethanesulfonic acid (TfOH; 44 μL, 0.5 mmol) was added dropwise to the resulting solution, and the whole system was stirred at room temperature for 1 hour. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by gel filtration chromatography to obtain 8,8'-bis(trifluoromethanesulfonyloxy)-4,4',6,6'-tetraiodo-2,2'-dimethoxy-1,1-binaphthyl (66 mg, yield=59%). The compound obtained was a mixture of (S)-isomer and (R)-isomer (racemate), and was successfully separated by a known chiral resolution technique into the (S)-isomer shown in the above reaction formula and the (R)-isomer.

The compound obtained was identified by $^1$H-NMR spectroscopy, $^{19}$F-NMR spectroscopy, and mass spectrometry (ASAP-MS) using an atmospheric pressure solid analysis probe (ASAP). The chemical shifts and mass-to-charge ratios (m/z) determined are as shown below. The deuterated solvent used in the $^1$H-NMR spectroscopy and $^{19}$F-NMR spectroscopy was CDCl$_3$. The same applies to other examples described below unless otherwise specified. The determined values are as follows.

$^1$H-NMR: δ (ppm)=8.47 (s, 2H), 7.99 (s, 2H), 7.57 (d, J=8.4 Hz, 2H), 7.44 (d, J=8.8 Hz, 2H), 6.72 (d, J=8.4 Hz, 2H), 3.75 (s, 6H).

$^{19}$F-NMR: δ (ppm)=−73.28.

MS (ASAP): Calcd for $C_{24}H_{12}F_6I_4O_8S_2$: m/z=1113.6056, Found m/z=1113.6072.

Figure 6:
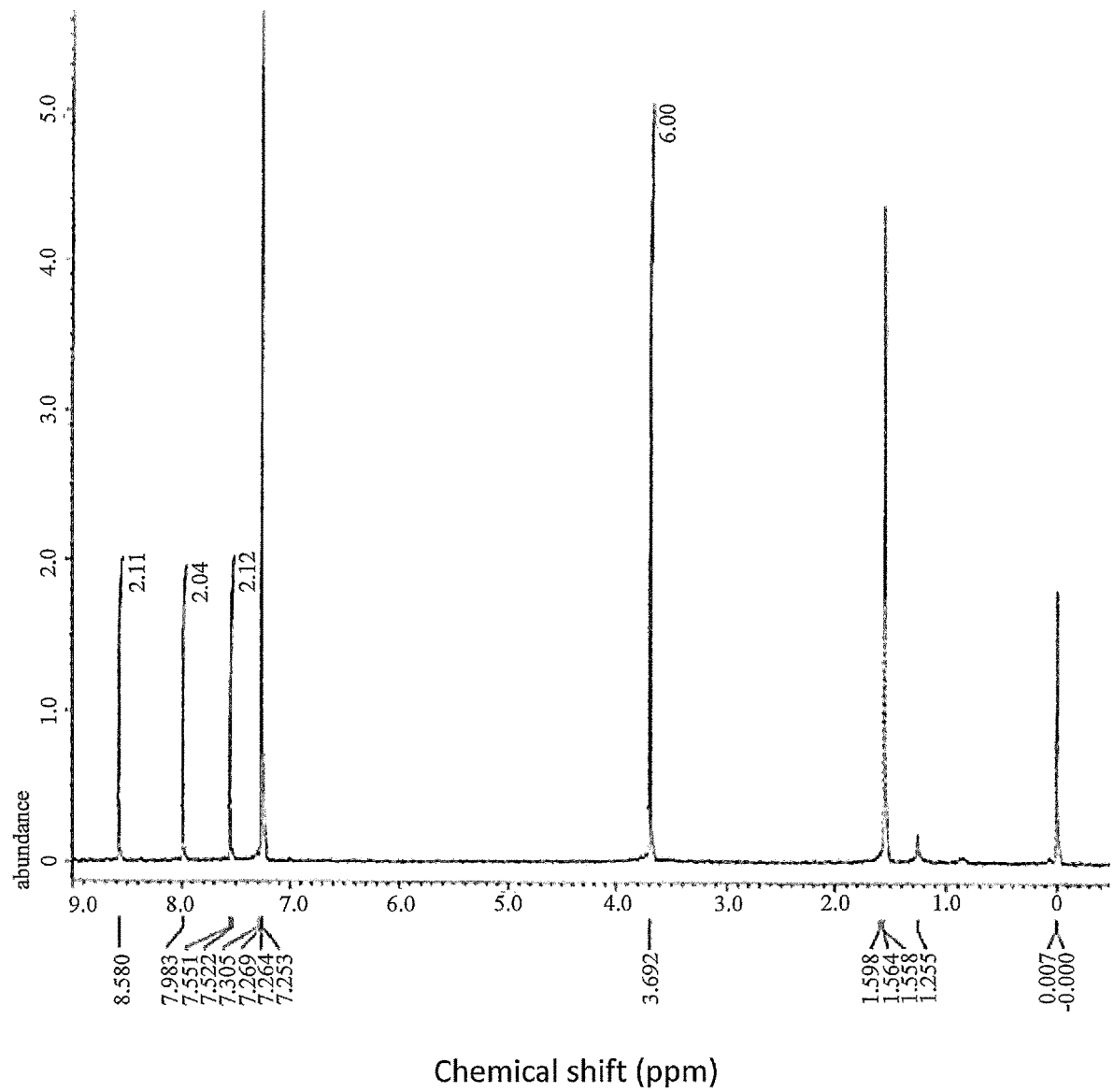
FIG. 6 shows a $^1$H-nuclear magnetic resonance (NMR) profile of a 1,1'-binaphthyl derivative produced in Example 1.
Figure 7:
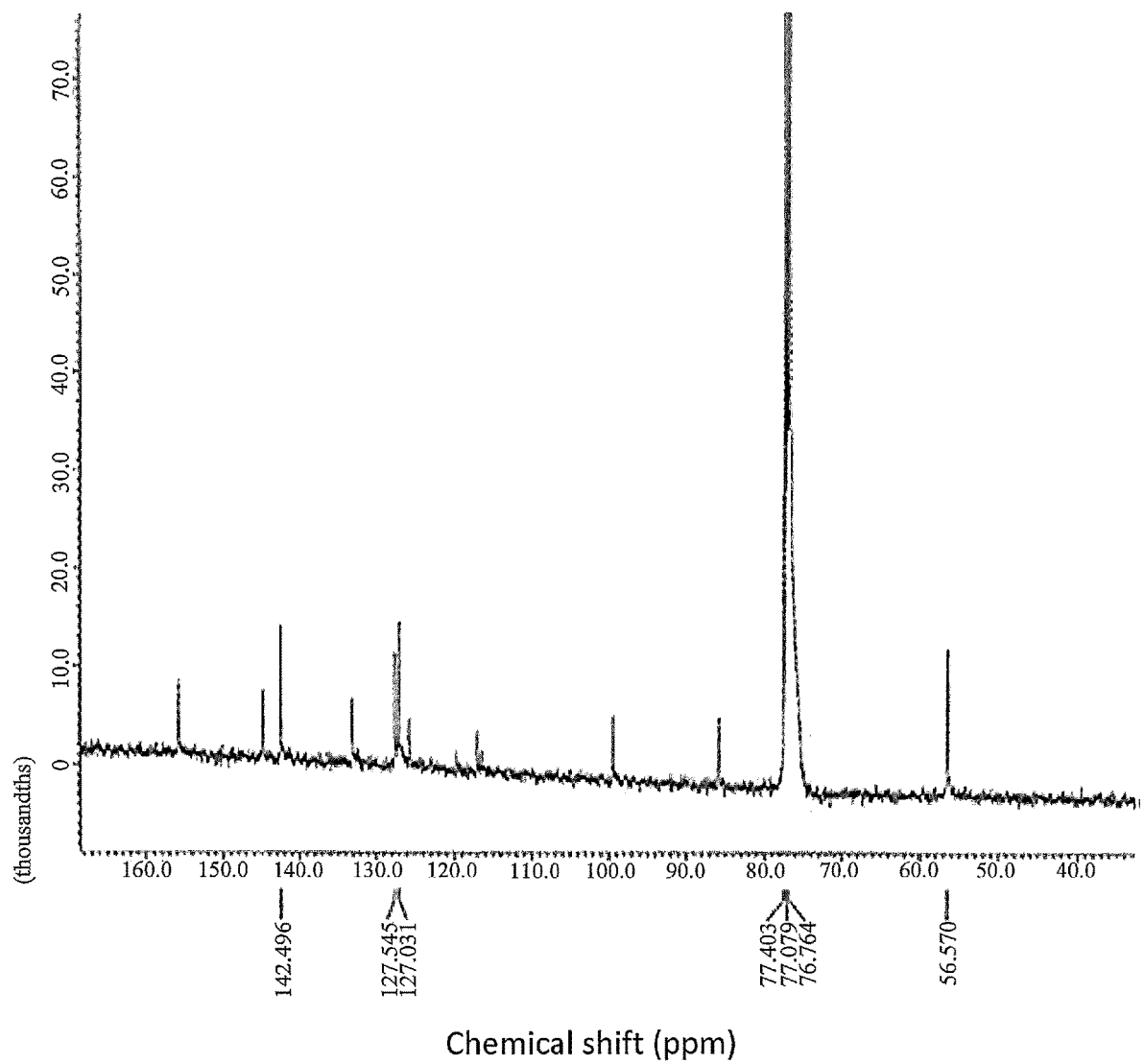
FIG. 7 shows a $^{13}$C-NMR profile of a 1,1'-binaphthyl derivative produced in Example 1.
Figure 8:
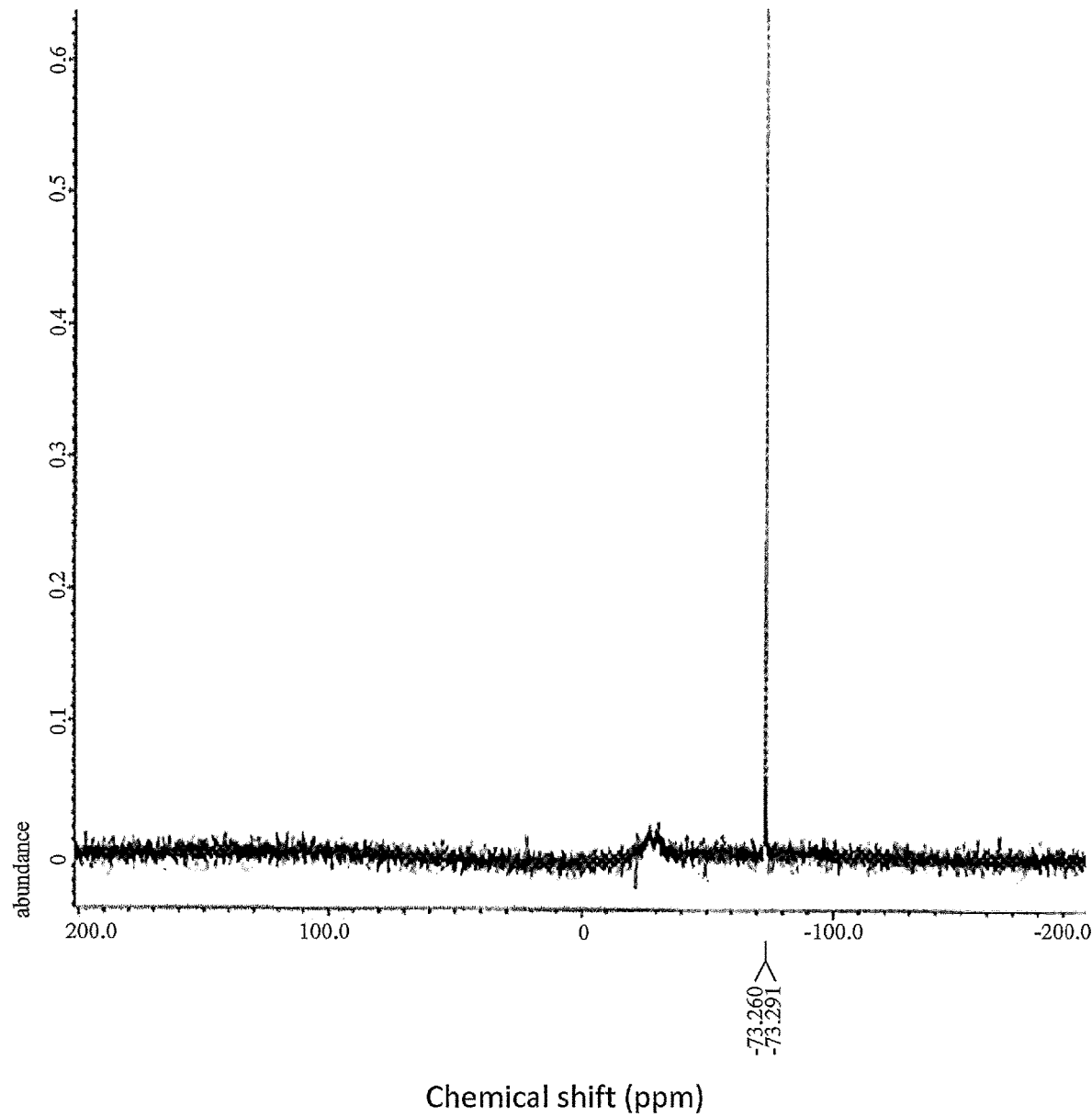
FIG. 8 shows a $^{19}$F-NMR profile of a 1,1'-binaphthyl derivative produced in Example 1.

The $^1$H-NMR spectrum is shown in FIG. 6, a $^{13}$C-NMR spectrum is shown in FIG. 7, and the $^{19}$F-NMR spectrum is shown in FIG. 8.

Example 2

In Example 2, as shown in the following reaction formula, 5,5',6,6',8,8'-hexakis(trifluoromethanesulfonyloxy)-4,4'-diiodo-2,2'-dimethoxy-1,1-binaphthyl, 4,5,5',6,6',8,8'-heptakis(trifluoromethanesulfonyloxy)-4'-iodo-2,2'-dimethoxy-1,1-binaphthyl, and 4,4',5,5',6,6',8,8'-octakis(trifluoromethanesulfonyloxy)-2,2'-dimethoxy-1,1-binaphthyl, which have trifluoromethanesulfonic acid groups introduced at the 8-position and 8'-position, were synthesized from (S)-4,4',6,6'-tetraiodo-2,2'-dimethoxy-1,1'-binaphthyl.

First, under air atmosphere, (S)-4,4',6,6'-tetraiodo-2,2'-dimethoxy-1,1'-binaphthyl (81.8 mg, 0.1 mmol) and DIH (379.3 mg, 1.0 mmol) were dissolved in methylene chloride (5 mL), then trifluoromethanesulfonic acid (0.17 mL, 2.0 mmol) was added dropwise to the resulting solution, and the whole system was stirred at room temperature for 1 hour. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by gel filtration chromatography to obtain 5,5',6,6',8,8'-hexakis(trifluoromethanesulfonyloxy)-4,4'-diiodo-2,2'-dimethoxy-1,1-binaphthyl (17.1 mg, yield=12%), 4,5,5',6,6',8,8'-heptakis(trifluoromethanesulfonyloxy)-4'-iodo-2,2'-dimethoxy-1,1-binaphthyl (42.5 mg, yield=29%), and 4,4',5,5',6,6',8,8'-octakis(trifluoromethanesulfonyloxy)-2,2'-dimethoxy-1,1-binaphthyl (31.2 mg, yield=21%). Each of the compounds obtained was a racemate and was successfully separated by a known chiral resolution technique into the (S)-isomer shown in the above reaction formula and the (R)-isomer.

The compounds obtained were identified by $^1$H-NMR spectroscopy, $^{13}$C-NMR spectroscopy, $^{19}$F-NMR spectroscopy, and ASAP-MS. The chemical shifts and mass-to-charge ratios (m/z) determined are as shown below.

5,5',6,6',8,8'-hexakis(trifluoromethanesulfonyloxy)-4,4'-diiodo-2,2'-di-methoxy-1,1-binaphthyl $^1$H-NMR: δ (ppm)=7.70 (s, 2H), 7.41 (s, 2H), 3.70 (s, 6H).

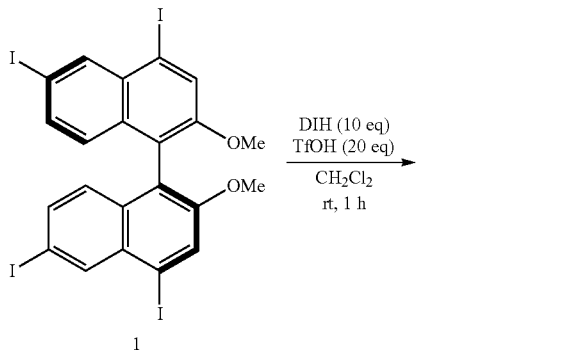

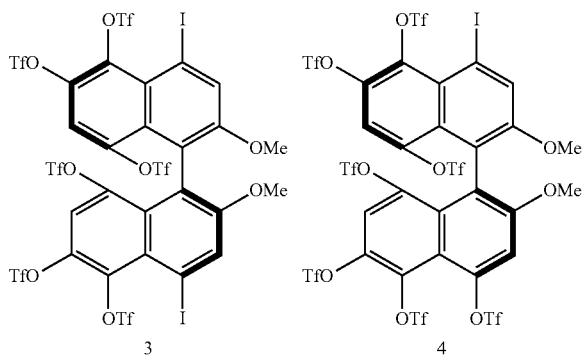

MS (ASAP): Calcd for $C_{28}H_{10}F_{18}I_2O_{20}S_6$: m/z=1453.59, Found m/z=1454.4027.

Figure 9:
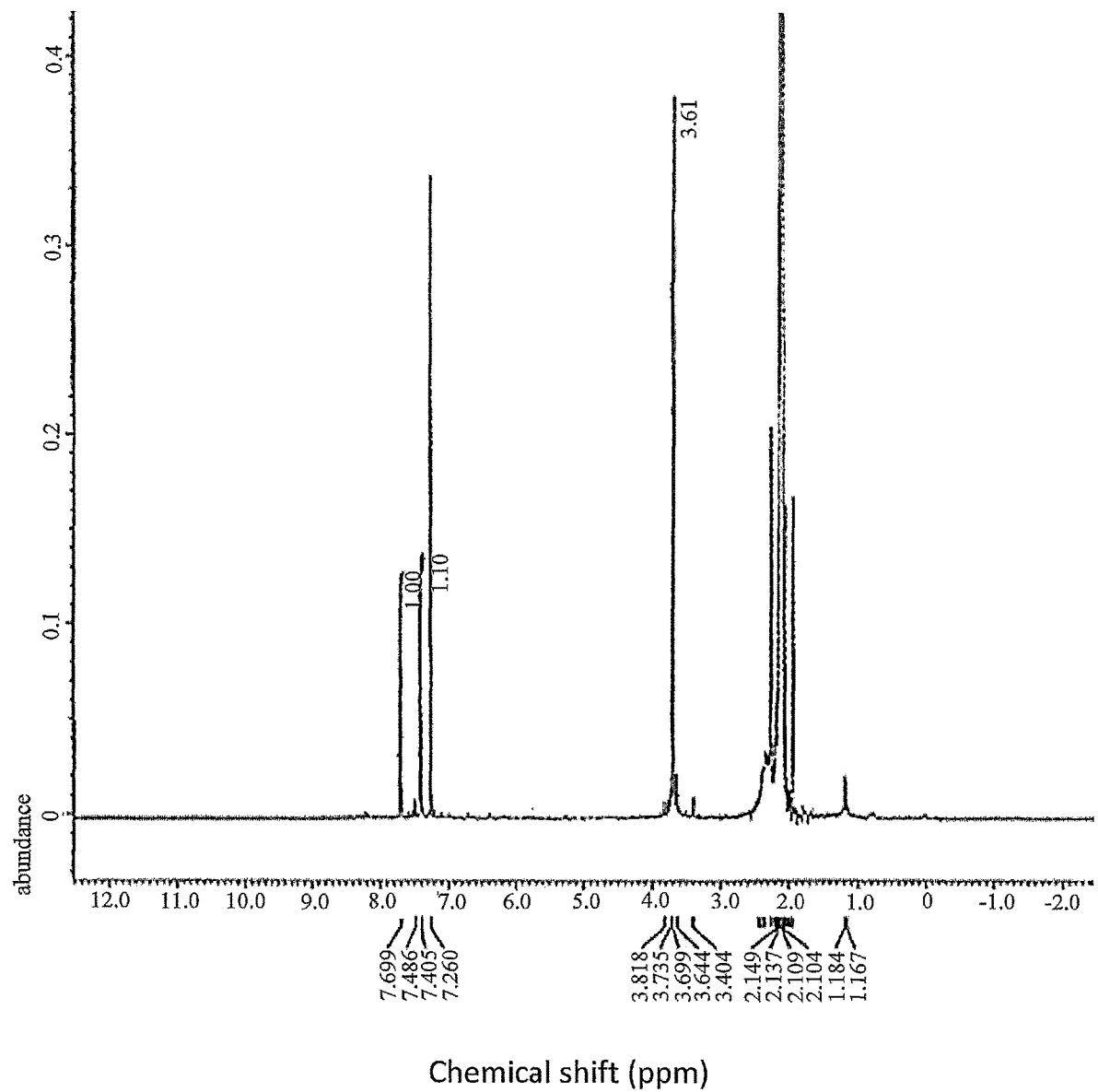
FIG. 9 shows a $^1$H-NMR profile of a 1,1'-binaphthyl derivative produced in Example 2.

The $^1$H-NMR spectrum is shown in FIG. 9.

4,5,5',6,6',8,8'-heptakis(trifluoromethanesulfonyloxy)-4'-iodo-2,2'-di-methoxy-1,1-binaphthyl $^1$H-NMR: δ (ppm)=7.76 (s, 1H), 7.60 (s, 1H), 7.57 (s, 1H), 7.45 (s, 1H), 3.79 (s, 6H).

MS (ASAP): Calcd for $C_{29}H_{10}F_{21}IO_{23}S_7$: m/z=1475.64, Found m/z=1476.4651.

Figure 10:
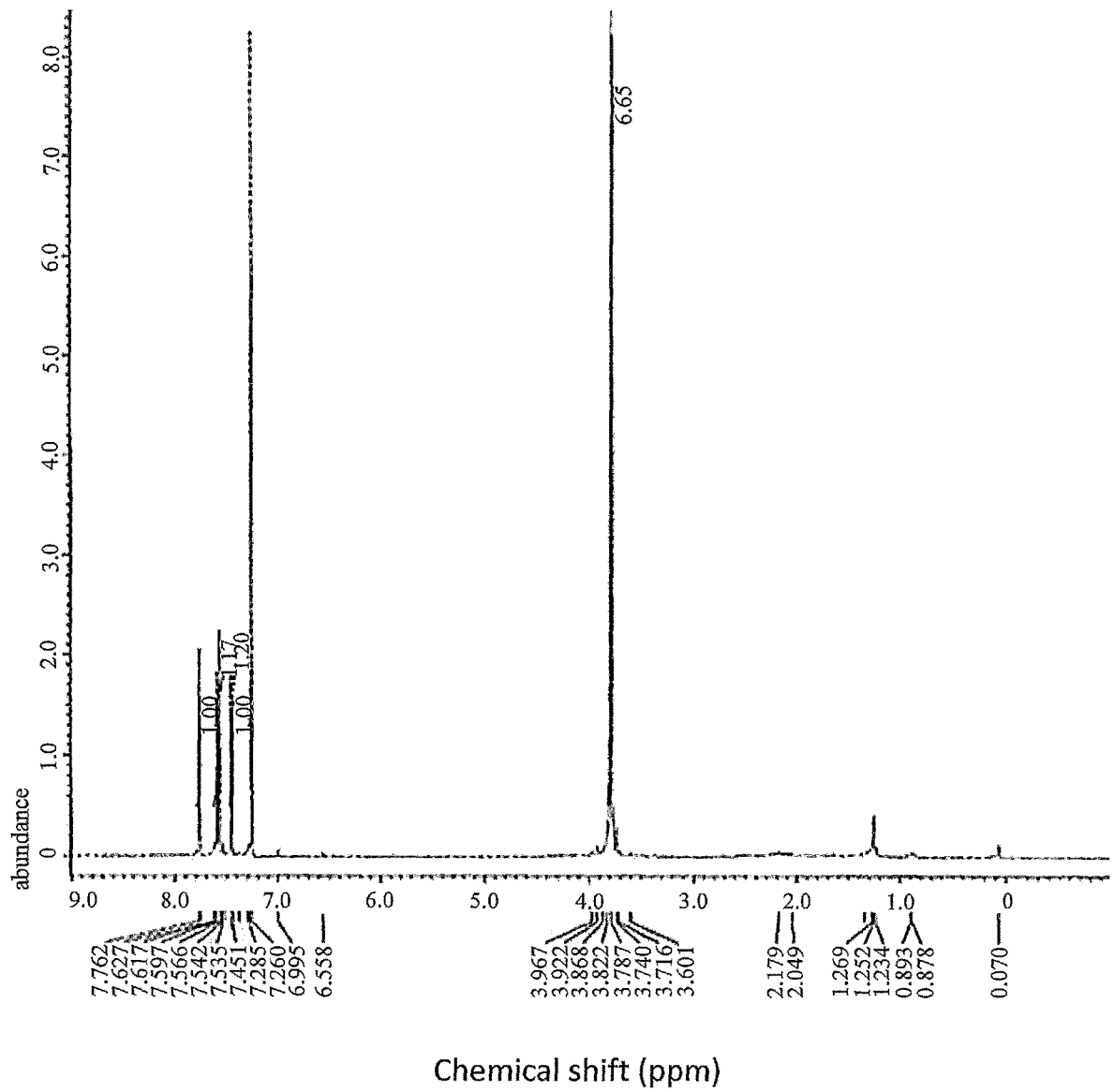
FIG. 10 shows a $^1$H-NMR profile of a 1,1'-binaphthyl derivative produced in Example 2.
Figure 11:
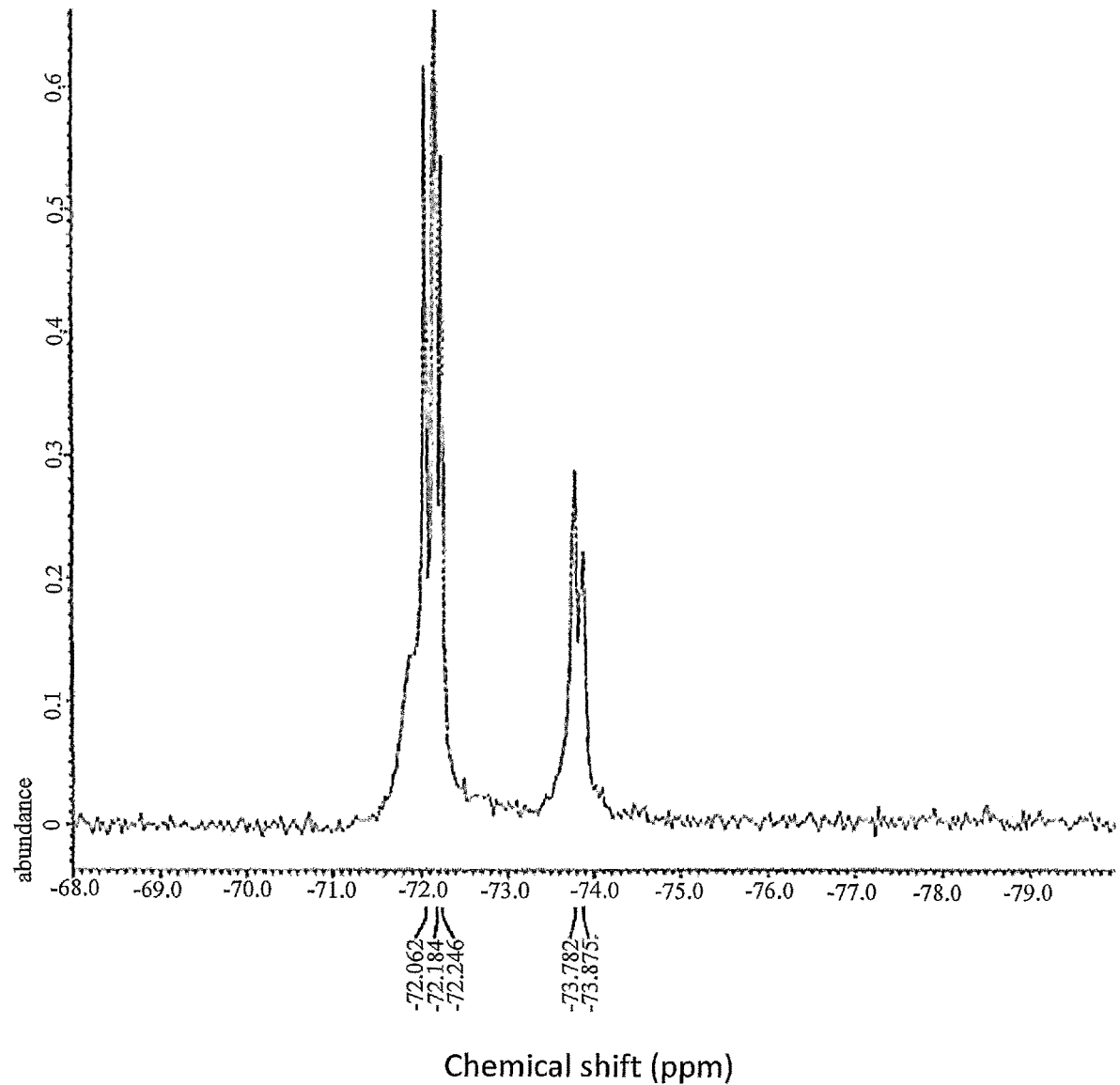
FIG. 11 shows a $^{19}$F-NMR profile of a 1,1'-binaphthyl derivative produced in Example 2.

The $^1$H-NMR spectrum is shown in FIG. 10, and the $^{19}$F-NMR spectrum is shown in FIG. 11.

4,4',5,5',6,6',8,8'-octakis(trifluoromethanesulfonyloxy)-2,2'-dimethoxy-1,1-binaphthyl $^1$H-NMR: δ (ppm)=7.62 (s, 2H), 7.57 (s, 2H), 3.82 (s, 6H).

$^{13}$C-NMR: δ (ppm)=156.869, 145.351, 144.131, 137.133, 133.662, 127.417, 227, 301, 116.128, 114.469, 112.123, 57.347.

$^{19}$F-NMR: δ (ppm)=−72.00, −72.12, −72.21, −73.81.

MS (ASAP): Calcd for $C_{30}H_{10}F_{24}I_4O_8S_2$: m/z=1497.68, Found m/z=1498.5033.

Figure 12:
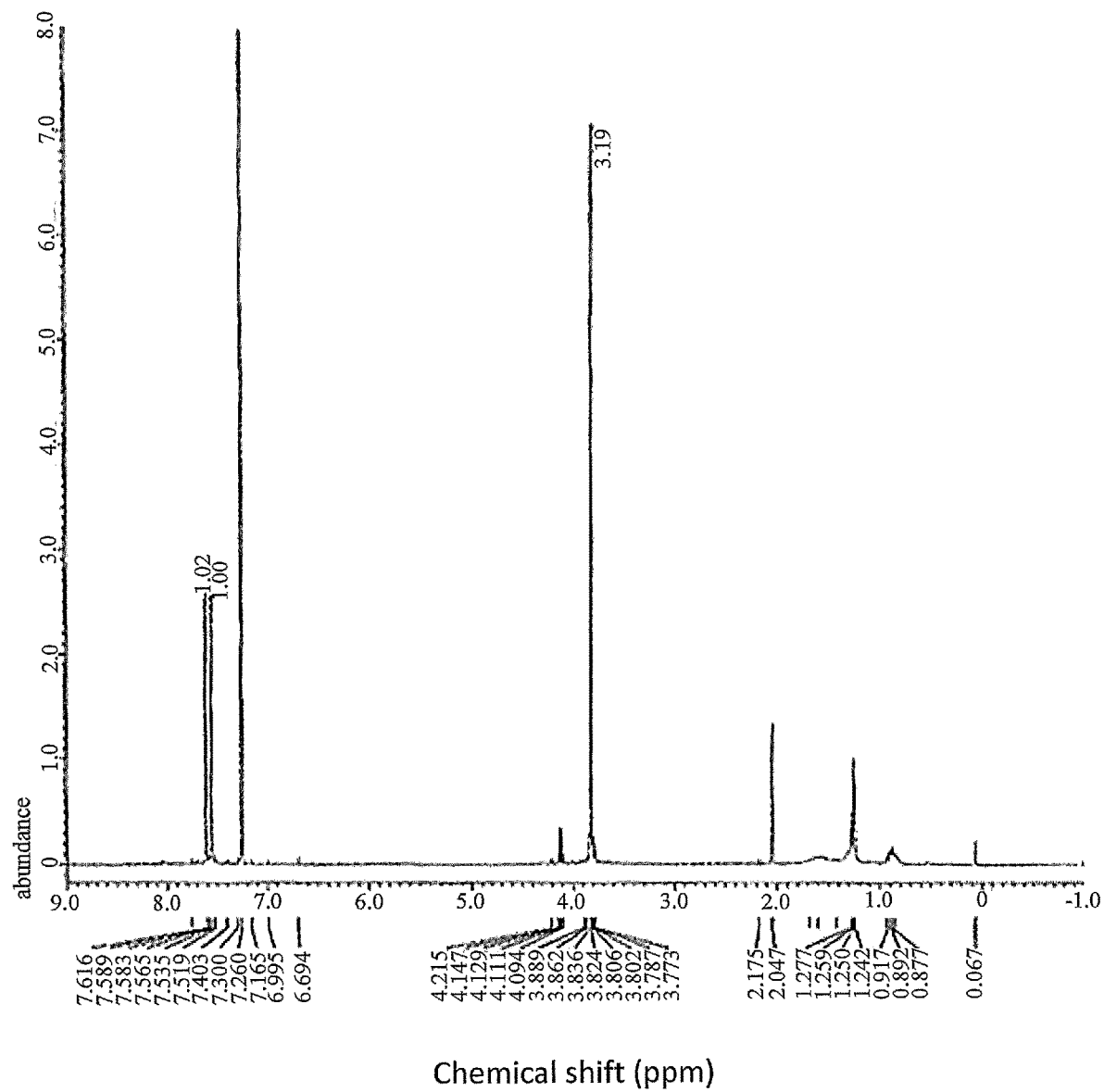
FIG. 12 shows a $^1$H-NMR profile of a 1,1'-binaphthyl derivative produced in Example 2.
Figure 13:
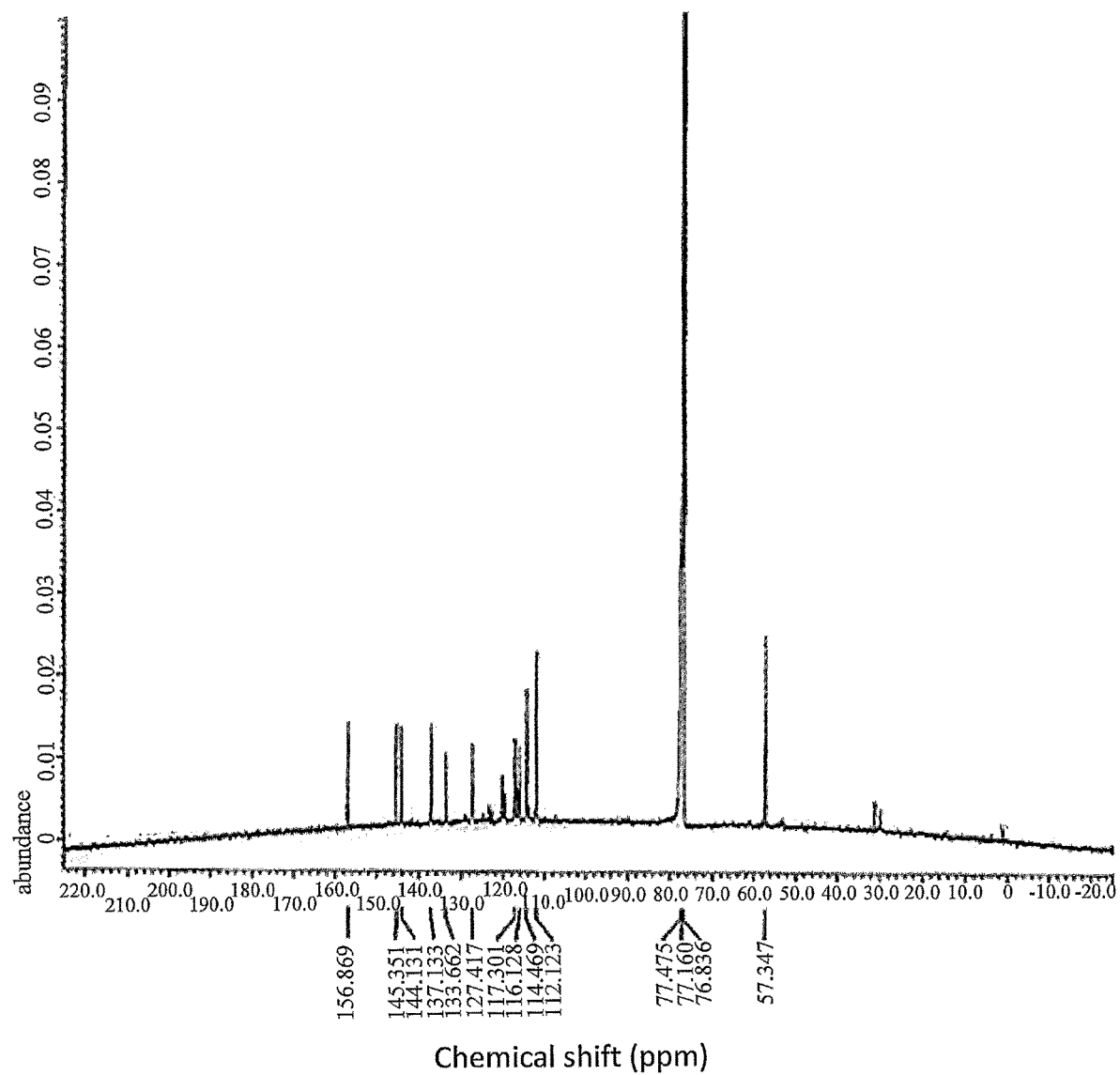
FIG. 13 shows a $^{13}$C-NMR profile of a 1,1'-binaphthyl derivative produced in Example 2.
Figure 14:
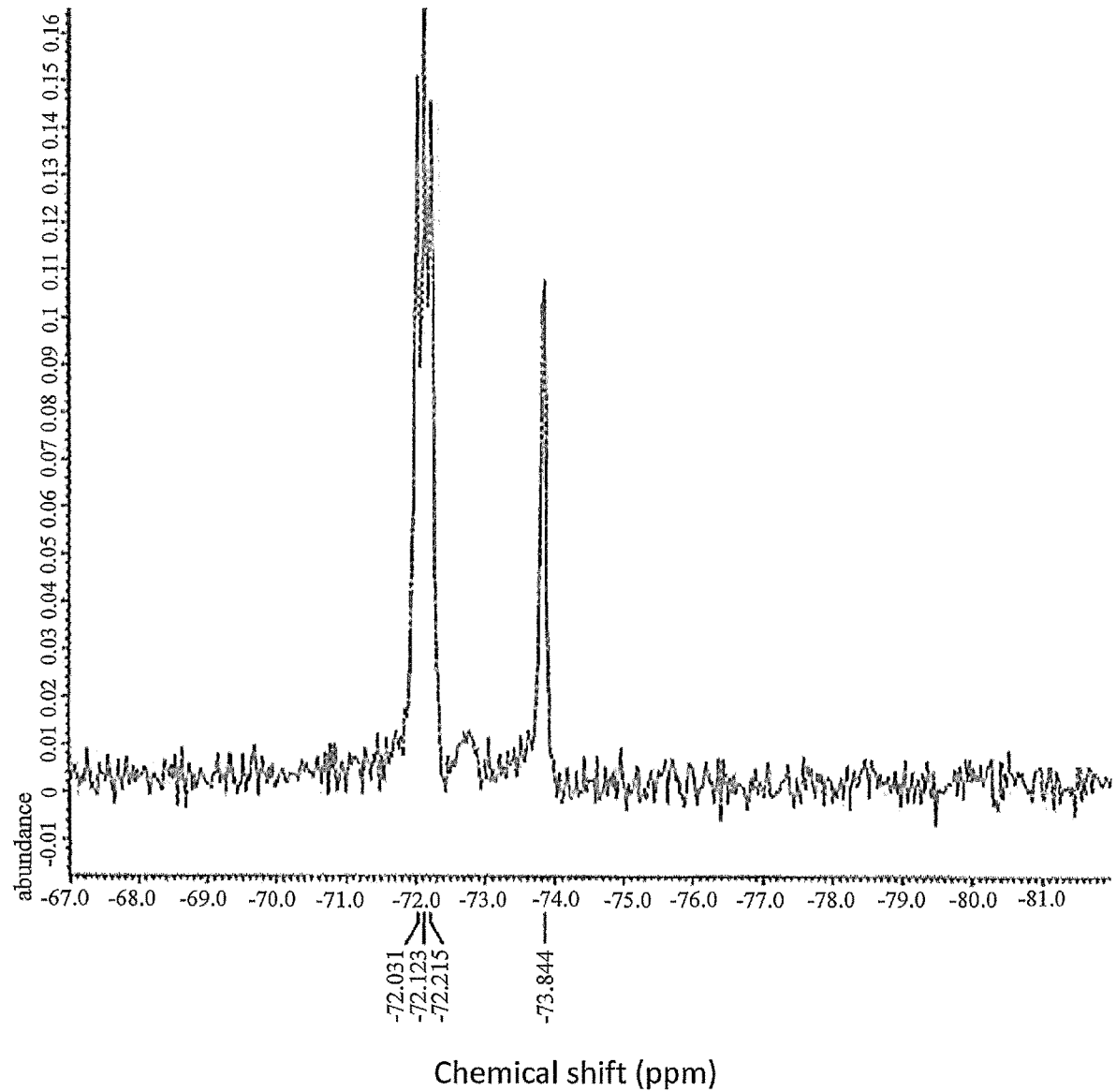
FIG. 14 shows a $^{19}$F-NMR profile of a 1,1'-binaphthyl derivative produced in Example 2.

The $^1$H-NMR spectrum is shown in FIG. 12, the $^{13}$C-NMR spectrum is shown in FIG. 13, and the $^{19}$F-NMR spectrum is shown in FIG. 14.

Figure 15:
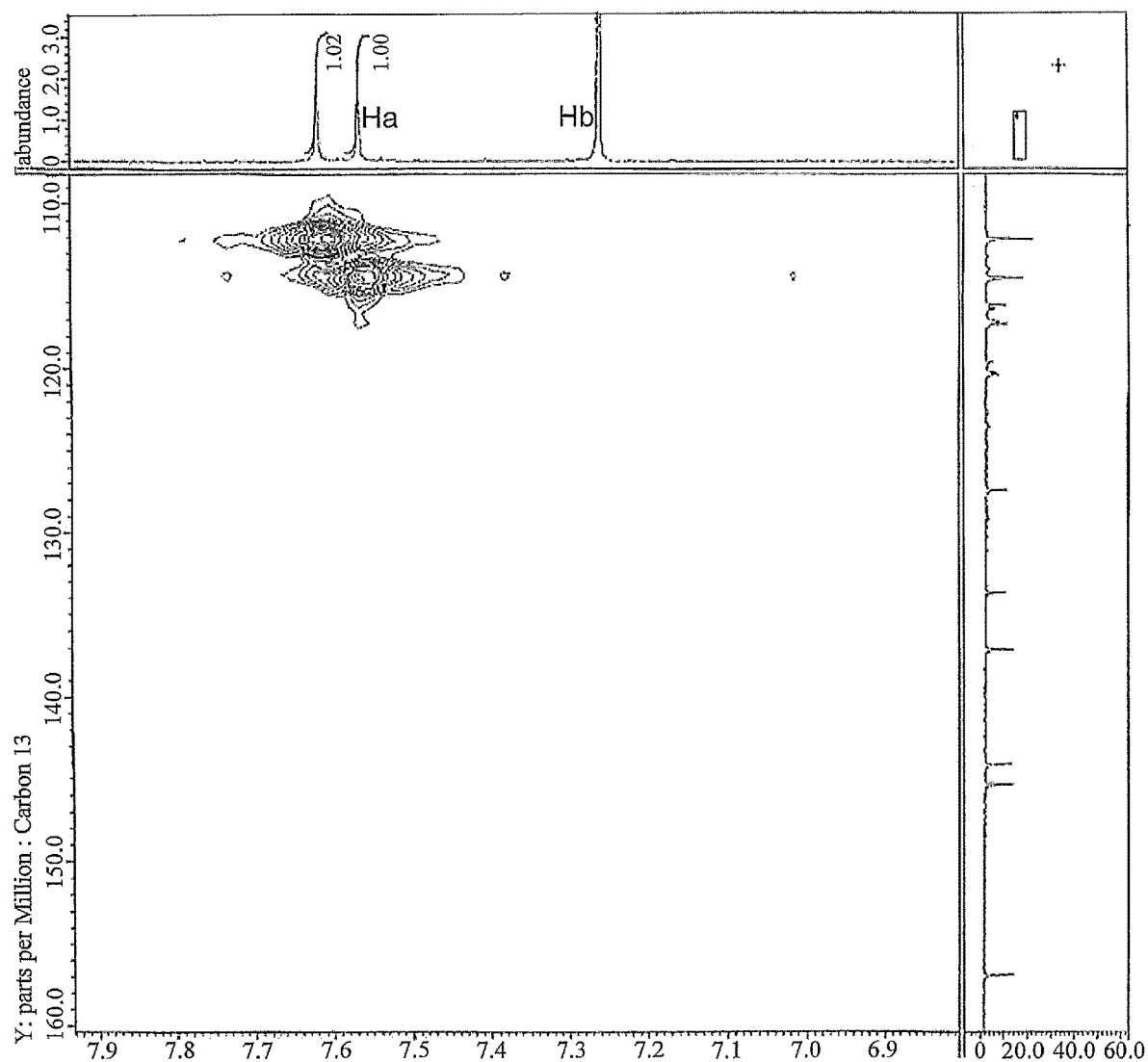
FIG. 15 shows a result of HMQC evaluation of (S)-4,4',5,5',6,6',8,8'-octakis(trifluoromethanesulfonyloxy)-2,2'-dimethoxy-1,1'-binaphthyl produced in Example 2.
Figure 16:
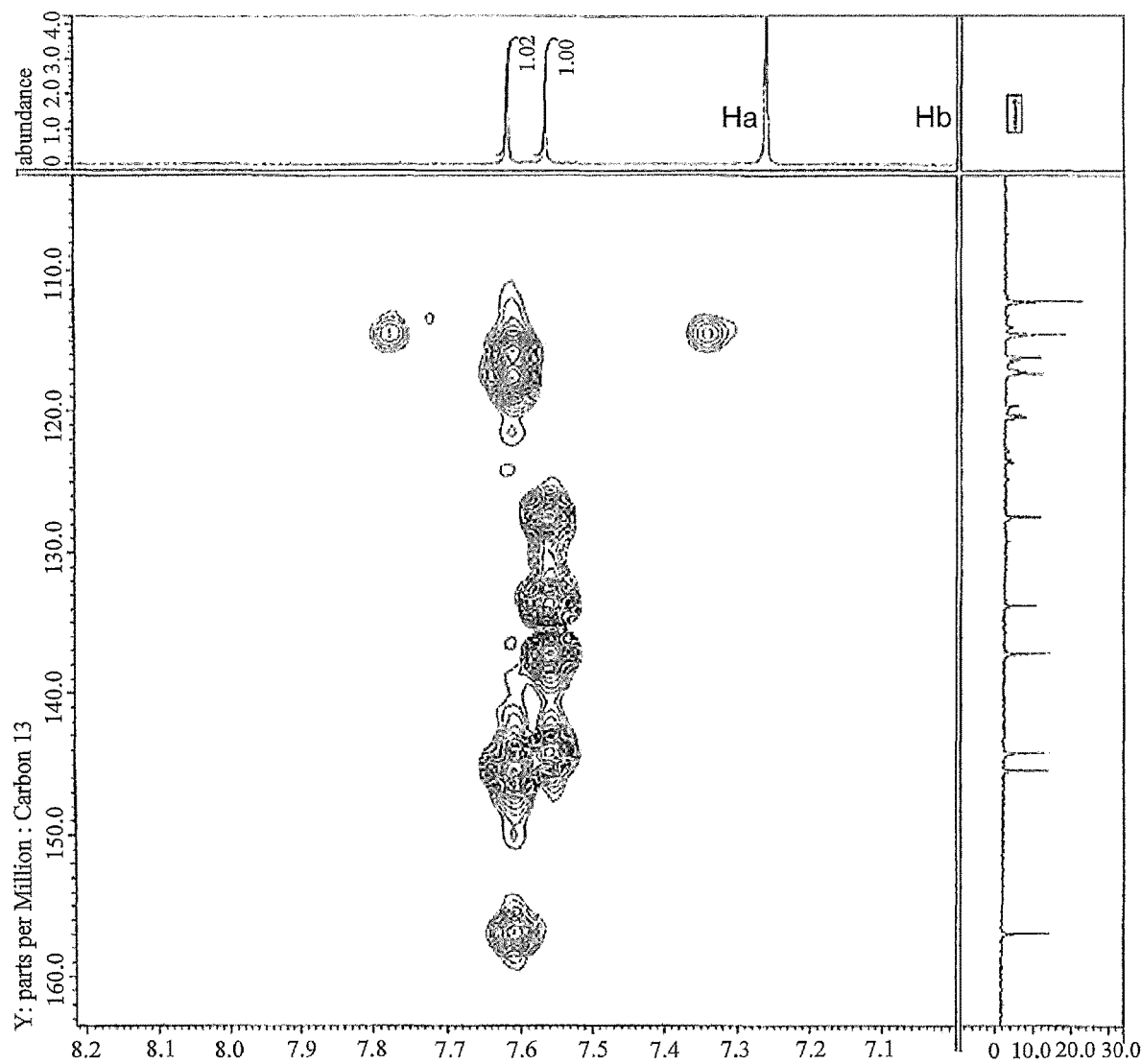
FIG. 16 shows a result of HMBC evaluation of (S)-4,4',5,5',6,6',8,8'-octakis(trifluoromethanesulfonyloxy)-2,2'-dimethoxy-1,1'-binaphthyl produced in Example 2.

For identification of 4,4',5,5',6,6',8,8'-octakis(trifluoromethanesulfonyloxy)-2,2'-dimethoxy-1,1'-binaphthyl, evaluation using $^1$H-NMR spectroscopy and $^{13}$C-NMR spectroscopy and based on HMQC (Hetero-nuclear Multiple Quantum Coherence) and HMBC (Hetero-nuclear Multiple-Bond Connectivity) was also conducted. The result for HMQC is shown in FIG. 15, and the result for HMBC is shown in FIG. 16. First of all, the fact that 20% nOe was observed between the protons of the methoxy groups and Ha at δ=7.62 ppm confirmed that Ha at δ=7.62 ppm were hydrogen atoms present at the 3-position and 3'-position of the binaphthyl skeleton (see the chemical formula shown below). Additionally, the result for HMQC revealed that Ha at δ=7.62 ppm had a correlation with a $^{13}$C peak at 112.123 ppm and Ha at δ=7.57 ppm had a correlation with a $^{13}$C peak at 114.47 ppm. Meanwhile, the result for HMBC revealed that Ha at δ=7.62 ppm had a correlation with $^{13}$C peaks at 116.13, 117.30, 145.35, and 156.87 ppm and Hb at δ=7.57 ppm had a correlation with $^{13}$C peaks at 127.42, 133.66, 137.13, and 144.13 ppm and that no carbon atoms existed which showed a cross peak correlated to both Ha and Hb. This confirmed that Hb were hydrogen atoms present at the 7-position and 7'-position of the binaphthyl skeleton. That is, any substituent was not present at the 3-, 3'-, 7-, or 7'-position of the binaphthyl skeleton in the produced derivative, and successful synthesis of 4,4',5,5',6,6',8,8'-octakis(trifluoromethanesulfonyloxy)-2,2'-dimethoxy-1,1'-binaphthyl was more certainly confirmed.

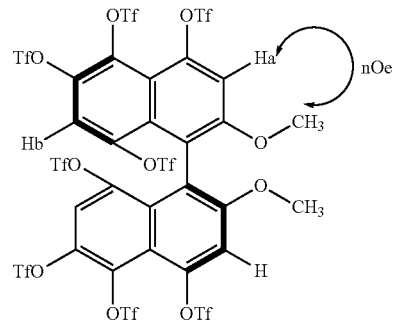

Example 3

In Example 3, as shown in the following reaction formula, 4,4',5,5',6,6',8,8'-octakis(trifluoromethanesulfonyloxy)-2,2'-dimethoxy-1,1'-binaphthyl having trifluoromethanesulfonic acid groups introduced at the 8-position and 8'-position was selectively synthesized from (S)-4,4',6,6'-tetraiodo-2,2'-dimethoxy-1,1'-binaphthyl.

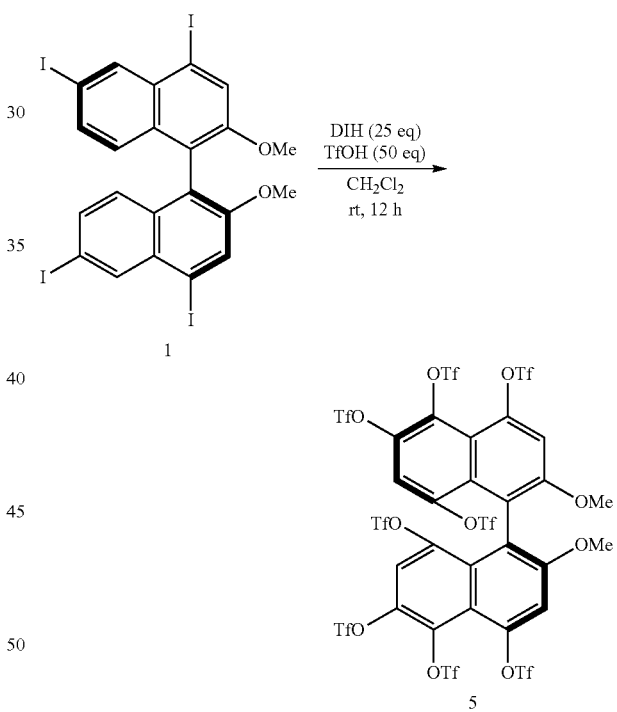

First, under air atmosphere, (S)-4,4',6,6'-tetraiodo-2,2'-dimethoxy-1,1'-binaphthyl (81.8 mg, 0.1 mmol) and DIH (945 mg, 2.5 mmol) were dissolved in methylene chloride (5 mL), then trifluoromethanesulfonic acid (0.44 mL, 5.0 mmol) was added dropwise to the resulting solution, and the whole system was stirred at room temperature for 12 hours. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by silica gel column chromatography (CHCl₃) to obtain 4,4',5,5',6,6',8,8'-octakis(trifluoromethanesulfonyloxy)-2,2'-dimethoxy-1,1'-binaphthyl (62.8 mg, yield=42%). The compound obtained was a racemate and was successfully separated by a known chiral resolution technique into the (S)-isomer shown in the above reaction formula and the (R)-isomer.

Example 4

In Example 4, as shown in the following reaction formula, 4,4',5,5',6,6',8,8'-octakis(trifluoromethanesulfonyloxy)-2,2'-dimethoxy-1,1'-binaphthyl having trifluoromethanesulfonic acid groups at the 8-position and 8'-position was synthesized from (S)-2,2'-dimethoxy-1,1'-binaphthyl.

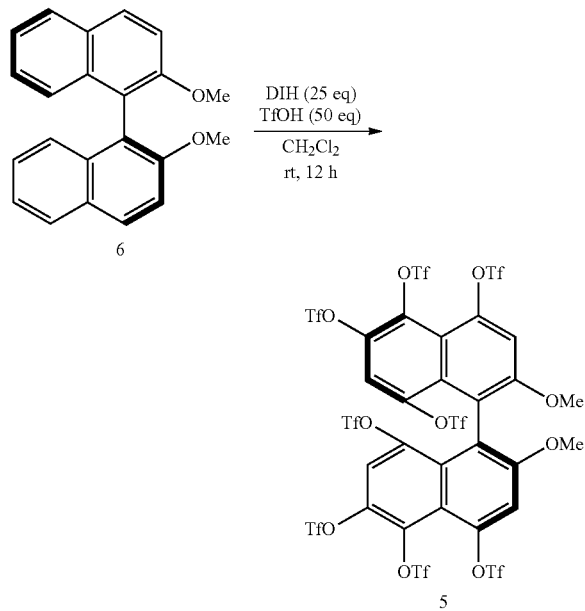

First, under air atmosphere, (S)-2,2'-dimethoxy-1,1'-binaphthyl (31.3 mg, 0.1 mmol) and DIH (945 mg, 2.5 mmol) were dissolved in methylene chloride (5 mL), then trifluoromethanesulfonic acid (0.44 mL, 5.0 mmol) was added dropwise to the resulting solution, and the whole system was stirred at room temperature for 12 hours. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by silica gel column chromatography (CHCl₃) to obtain 4,4',5,5',6,6',8,8'-octakis(trifluoromethanesulfonyloxy)-2,2'-dimethoxy-1,1'-binaphthyl (49.4 mg, yield=32%). The compound obtained was a racemate and was successfully separated by a known chiral resolution technique into the (S)-isomer shown in the above reaction formula and the (R)-isomer.

The amount of DIH used was changed to 3.0 mmol, and the amount of trifluoromethanesulfonic acid used was changed to 6.0 mmol. In this case, a reaction at room temperature for 20 minutes gave 4,4',5,5',6,6',8,8'-octakis(trifluoromethanesulfonyloxy)-2,2'-dimethoxy-1,1'-binaphthyl in a yield of 27%.

Example 5

In Example 5, as shown in the following reaction formula, rac-4,4',5,5',6,6',8,8'-octakis(trifluoromethanesulfonyloxy)-2,2'-dimethoxy-1,1'-binaphthyl having trifluoromethanesulfonic acid groups introduced at the 8-position and 8'-position was synthesized from 2-methoxynaphthalene.

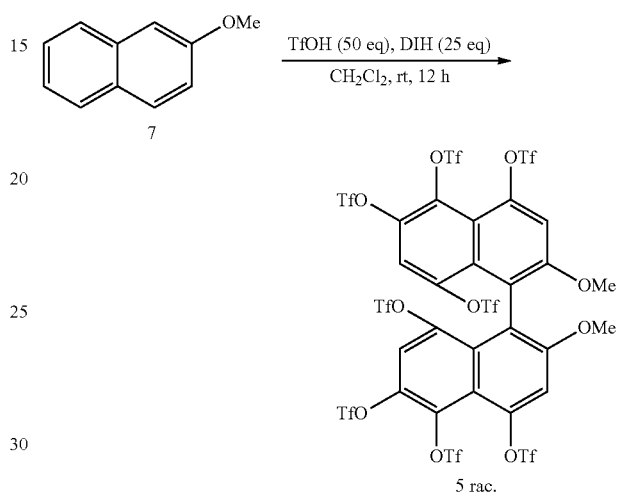

First, under air atmosphere, 2-methoxynaphthalene (15.8 mg, 0.1 mmol) and DIH (945 mg, 2.5 mmol) were dissolved in methylene chloride (5 mL), then trifluoromethanesulfonic acid (0.44 mL, 5.0 mmol) was added dropwise to the resulting solution, and the whole system was stirred at room temperature for 12 hours. After the stirring, a saturated aqueous solution of sodium hydrogen carbonate was slowly added dropwise to the reaction mixture to neutralize the mixture. Next, sodium sulfite was added to the neutralized mixture, and an organic phase was extracted with methylene chloride. The extracted organic phase was washed with water and then dried over magnesium sulfate. Next, the solvent was removed using an evaporator to obtain a crude product. After that, the obtained crude product was filtered by silica gel column chromatography (CHCl₃) to obtain rac-4,4',5,5',6,6',8,8'-octakis(trifluoromethanesulfonyloxy)-2,2'-dimethoxy-1,1'-binaphthyl (27.1 mg, yield=36%).

Example 6

In Example 6, as shown in the following reaction formula, 8-trifluoromethanesulfonyloxy-4,4',6,6'-tetraiodo-2,2'-dimethoxy-1,1'-binaphthyl which is a monotrifluoromethanesulfonyloxy compound (14 mg, yield=15%) and 8,8'-bis(trifluoromethanesulfonyloxy)-4,4',6,6'-tetraiodo-2,2'-dimethoxy-1,1'-binaphthyl which is a bis(trifluoromethanesulfonyloxy) compound (23 mg, yield=21%) were obtained from (S)-4,4',6,6'-tetraiodo-2,2'-dimethoxy-1,1'-binaphthyl (81.8 mg, 0.1 mmol) in the same manner as in Example 1, except that the amount of DIH used was 76 mg (0.2 mmol) and the amount of trifluoromethanesulfonic acid used was 0.035 mL (0.4 mmol). Each of the compounds obtained was a racemate and was successfully separated by a known chiral resolution technique into the (S)-isomer shown in the following reaction formula and the (R)-isomer.

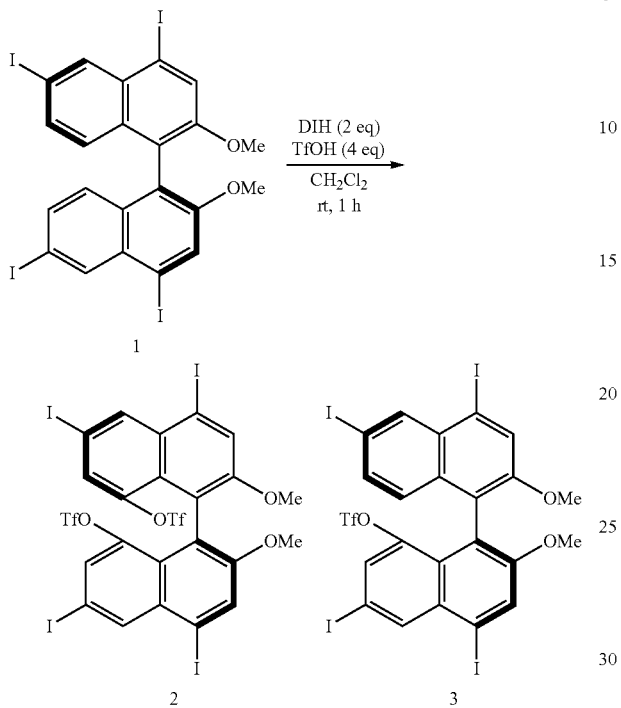

The obtained compounds were identified by $^1$H-NMR spectroscopy, $^{19}$F-NMR spectroscopy, and ASAP-MS. The chemical shifts and mass-to-charge ratios (m/z) determined are as shown below.

Figure 17:
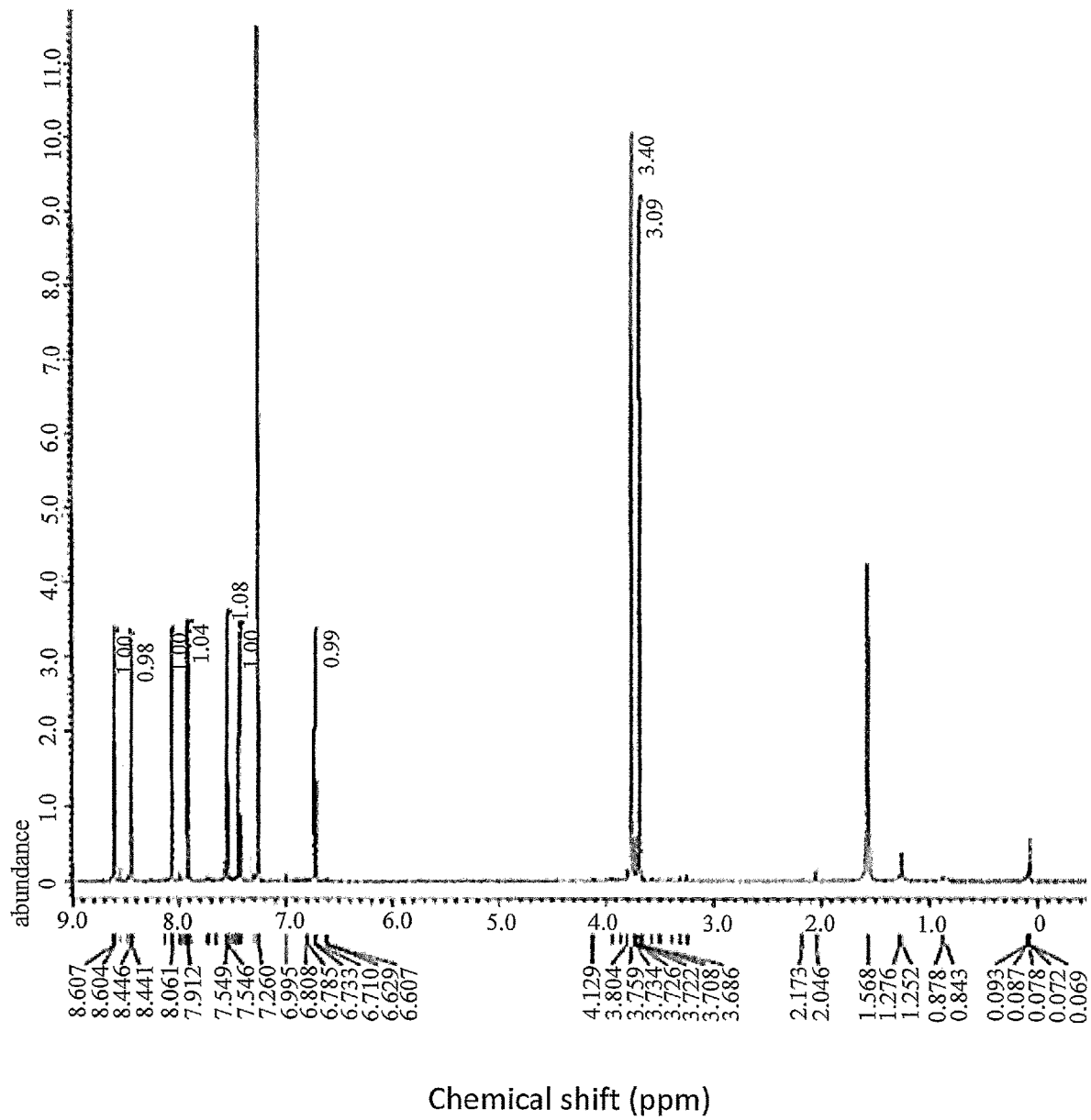
FIG. 17 shows a $^1$H-NMR profile of a 1,1'-binaphthyl derivative produced in Example 6.
Figure 18:
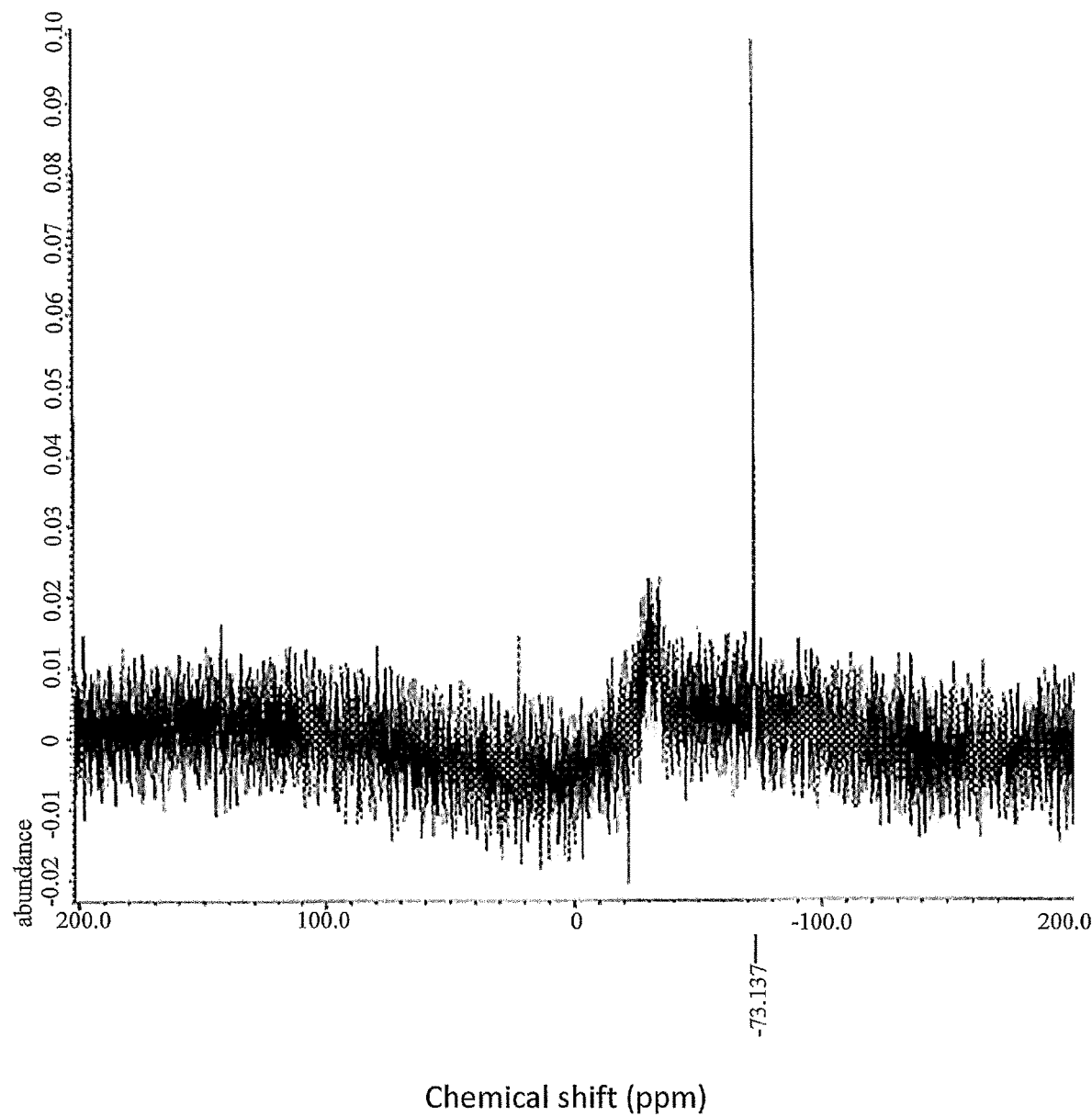
FIG. 18 shows a $^{19}$F-NMR profile of a 1,1'-binaphthyl derivative produced in Example 6.

8-trifluoromethanesulfonyloxy-4,4',6,6'-tetraiodo-2,2'-dimethoxy-1,1'-binaphthyl $^1$H-NMR: δ (ppm)=8.61 (s, 1H), 8.44 (s, 1H), 8.01 (s, 1H), 7.91 (s, 1H), 7.55 (s, 1H), 7.44 (d, J=8.8 Hz, 1H), 6.72 (d, J=9.2 Hz, 3H), 3.76 (s, 3H), 3.69 (s, 3H).
$^{19}$F-NMR: δ (ppm)=−73.14.
MS (ASAP): Calcd for $C_{23}H_{13}F_3I_4O_5S$: m/z=965.66, Found m/z=965.6702.
The $^1$H-NMR spectrum is shown in FIG. 17, and the $^{19}$F-NMR spectrum is shown in FIG. 18.

8,8'-bis(trifluoromethanesulfonyloxy)-4,4',6,6'-tetraiodo-2,2'-dimethoxy-1,1'-binaphthyl $^1$H-NMR: δ (ppm)=8.47 (s, 2H), 7.99 (s, 2H), 7.57 (d, J=8.4 Hz, 2H), 7.44 (d, J=8.8 Hz, 2H), 6.72 (d, J=8.4 Hz, 2H), 3.75 (s, 6H).
$^{19}$F-NMR: δ (ppm)=−73.28.
MS (ASAP): Calcd for $C_{24}H_{12}F_6I_4O_8S_2$: m/z=1113.6056, Found m/z=1113.6072.

Example 7

In Example 7, as shown in the following reaction formula, 6,8,8'-tris(trifluoromethanesulfonyloxy)-4,4',6'-triiodo-2,2'-dimethoxy-1,1'-binaphthyl (53 mg, yield=47%) was obtained from (S)-4,4',6,6'-tetraiodo-2,2'-dimethoxy-1,1'-binaphthyl (81.8 mg, 0.1 mmol) in the same manner as in Example 1, except that the amount of DIH used was 114 mg (0.3 mmol) and the amount of trifluoromethanesulfonic acid used was 0.088 mL (1.0 mmol). The compound obtained was a racemate and was successfully separated by a known chiral resolution technique into the (S)-isomer shown in the following reaction formula and the (R)-isomer.

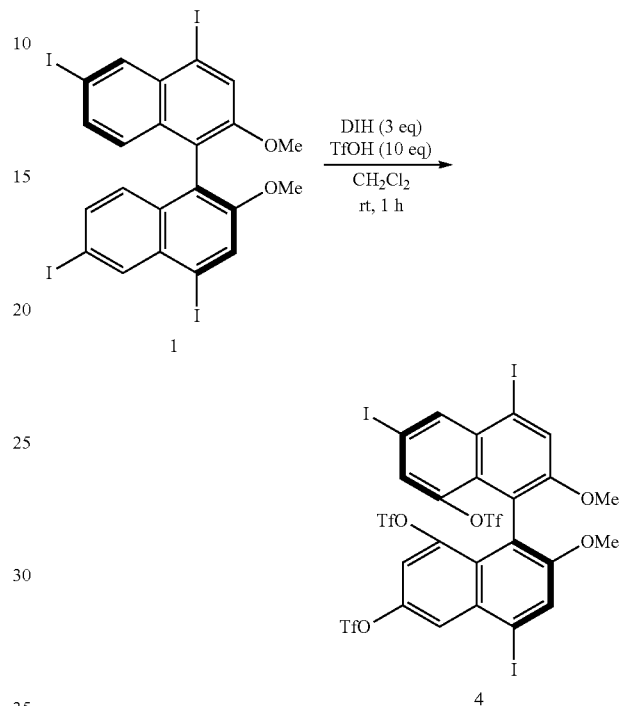

The compound obtained was identified by $^1$H-NMR spectroscopy, $^{19}$F-NMR spectroscopy, and ASAP-MS. The chemical shifts and mass-to-charge ratios (m/z) determined are as shown below.

Figure 19:
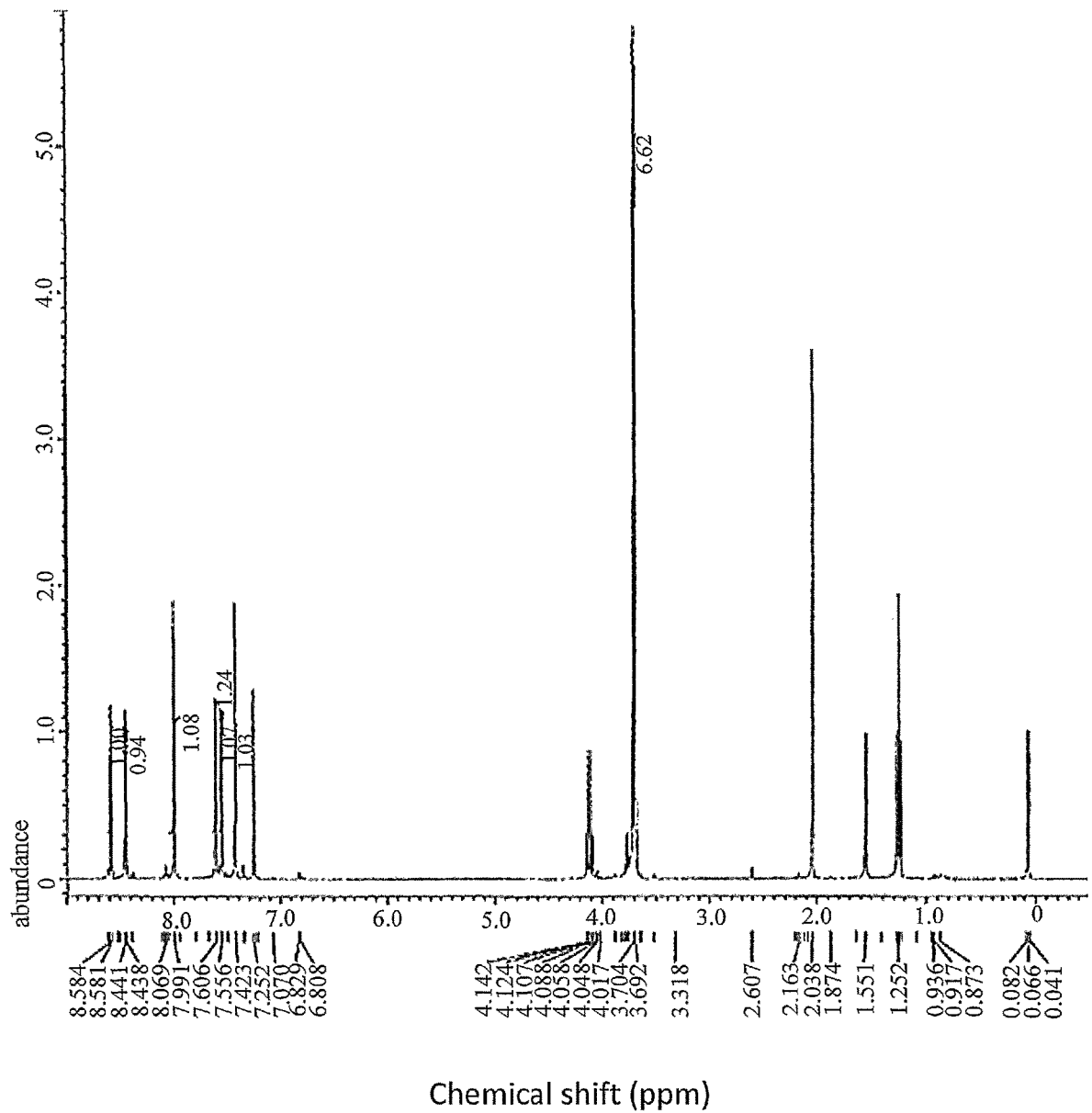
FIG. 19 shows a $^1$H-NMR profile of a 1,1'-binaphthyl derivative produced in Example 7.
Figure 20:
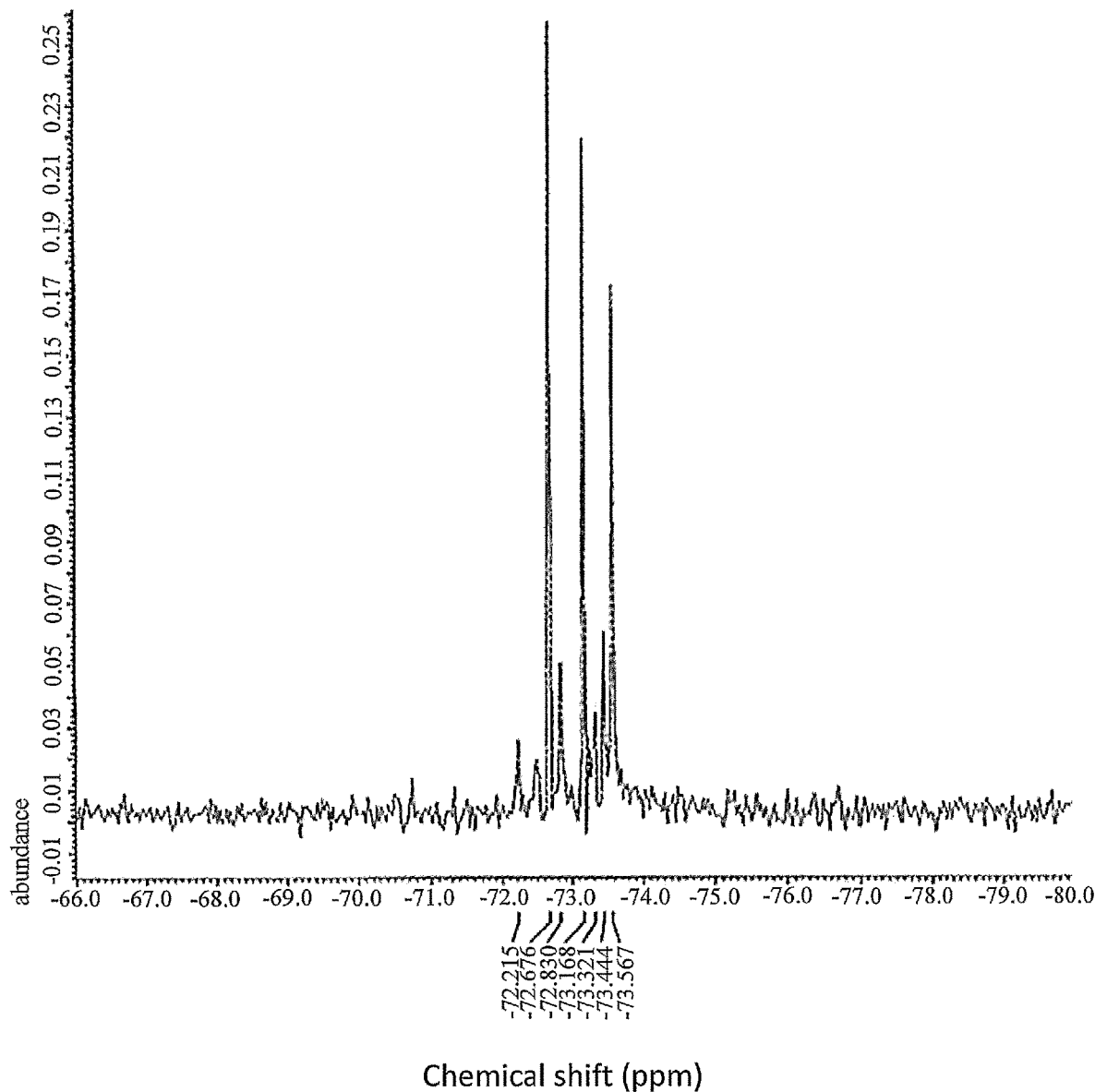
FIG. 20 shows a $^{19}$F-NMR profile of a 1,1'-binaphthyl derivative produced in Example 7.

$^1$H-NMR: δ (ppm)=8.59 (s, 1H), 8.45 (s, 1H), 8.00 (s, 1H), 7.61 (s, 1H), 7.56 (s, 1H), 7.43 (s, 1H), 3.71 (s, 3H), 3.70 (s, 3H).
$^{19}$F-NMR: δ (ppm)=−72.68, −73.17, −73.58.
MS (ASAP): Calcd for $C_{25}H_{12}F_9I_3O_{11}S_3$: m/z=1135.65, Found m/z=1136.5051.
The $^1$H-NMR spectrum is shown in FIG. 19, and the $^{19}$F-NMR spectrum is shown in FIG. 20.

Example 8

In Example 8, as shown in the following reaction formula, 6,6',8,8'-tetra(trifluoromethanesulfonyloxy)-4,4'-diiodo-2,2'-dimethoxy-1,1'-binaphthyl and 4,6,6',8,8'-penta(trifluoromethanesulfonyloxy)-4'-iodo-2,2'-dimethoxy-1,1'-binaphthyl were obtained from (S)-4,4',6,6'-tetraiodo-2,2'-dimethoxy-1,1'-binaphthyl (81.8 mg, 0.1 mmol) in the same manner as in Example 1, except that the amount of DIH used was 189 mg (0.5 mmol) and the amount of trifluoromethanesulfonic acid used was 0.170 mL (2.0 mmol). Each of the compounds obtained was a racemate and was successfully separated by a known chiral resolution technique into the (S)-isomer shown in the following reaction formula and the (R)-isomer.

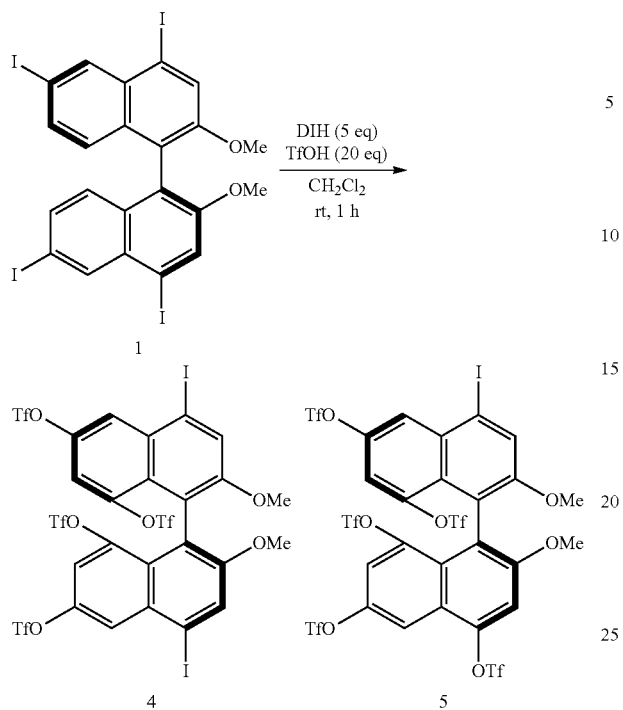

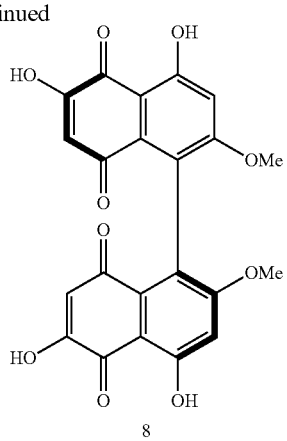

The compounds obtained were identified by molecular weight measurement and ASAP-MS. The mass-to-charge ratios (m/z) determined are as shown below.

6,6',8,8'-tetra(trifluoromethanesulfonyloxy)-4,4'-diiodo-2,2'-dimethoxy-1,1'-binaphthyl MS (ASAP): Calcd for $C_{26}H_{12}F_{12}I_2O_{14}S_4$: m/z=1157.701, Found m/z=1157.5494.

4,6,6',8,8'-penta(trifluoromethanesulfonyloxy)-4'-iodo-2,2'-dimethoxy-1,1'-binaphthyl MS (ASAP): Calcd for $C_{27}H_{12}F_{13}IO_{17}S_5$: m/z=1179.6013, Found m/z=1179.6013.

Application Example 1

In Application Example 1, as shown in the following reaction formula, (S)-4,4',6,6'-tetrahydroxy-2,2'-dimethoxy-1,1'-binaphtho-para-quinone which is a quinone compound was synthesized through hydrolysis of (S)-4,4',5,5',6,6',8,8'-octakis(trifluoromethanesulfonyloxy)-2,2'-dimethoxy-1,1'-binaphthyl as produced in Example 2 or 3.

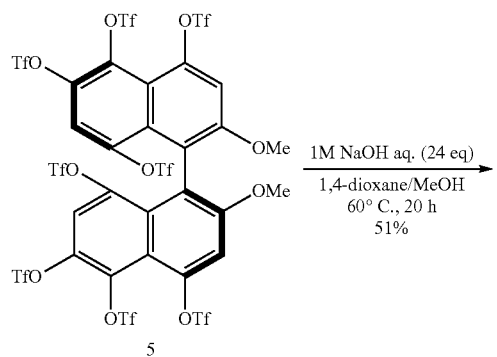

First, under air atmosphere, (S)-4,4',5,5',6,6',8,8'-octakis(trifluoromethanesulfonyloxy)-2,2'-dimethoxy-1,1'-binaphthyl (149 mg, 0.1 mmol) was dissolved in a liquid mixture of 1,4-dioxane (10 mL) and methanol (5 mL), then a 1 M aqueous sodium hydroxide solution (2.4 mL, 2.4 mmol) was added to the resulting solution, and the whole system was stirred at 60° C. for 20 hours. After the stirring, 10 wt % hydrochloric acid was added to the reaction mixture to neutralize the mixture, and an organic phase was extracted with diethyl ether. The extracted organic phase was then dried over magnesium sulfate. Next, the solvent was removed using an evaporator to obtain a crude product. After that, the obtained crude product was recrystallized from chloroform to obtain (S)-4,4',6,6'-tetrahydroxy-2,2'-dimethoxy-1,1'-binaphtho-para-quinone as an orange solid (21.5 mg, yield=51%).

When 2.0 mmol of sodium hydride was used instead of sodium hydroxide, a reaction at room temperature for 20 hours gave (S)-4,4',6,6'-tetrahydroxy-2,2'-dimethoxy-1,1'-binaphtho-para-quinone in a yield of more than 98% (quant).

The compound obtained was identified by $^1$H-NMR spectroscopy and ASAP-MS. The chemical shifts and mass-to-charge ratios (m/z) determined are as shown below. The deuterated solvent used in the $^1$H-NMR spectroscopy was $(CD_3)_2CO$.

$^1$H-NMR: δ (ppm)=12.48 (br), 9.79 (br), 6.79 (s, 2H), 5.91 (s, 2H), 3.76 (s, 6H).

MS (ASAP): Calcd for $C_{22}H_{14}O_{10}$: m/z=438.06, Found m/z=439.1201.

Figure 21:
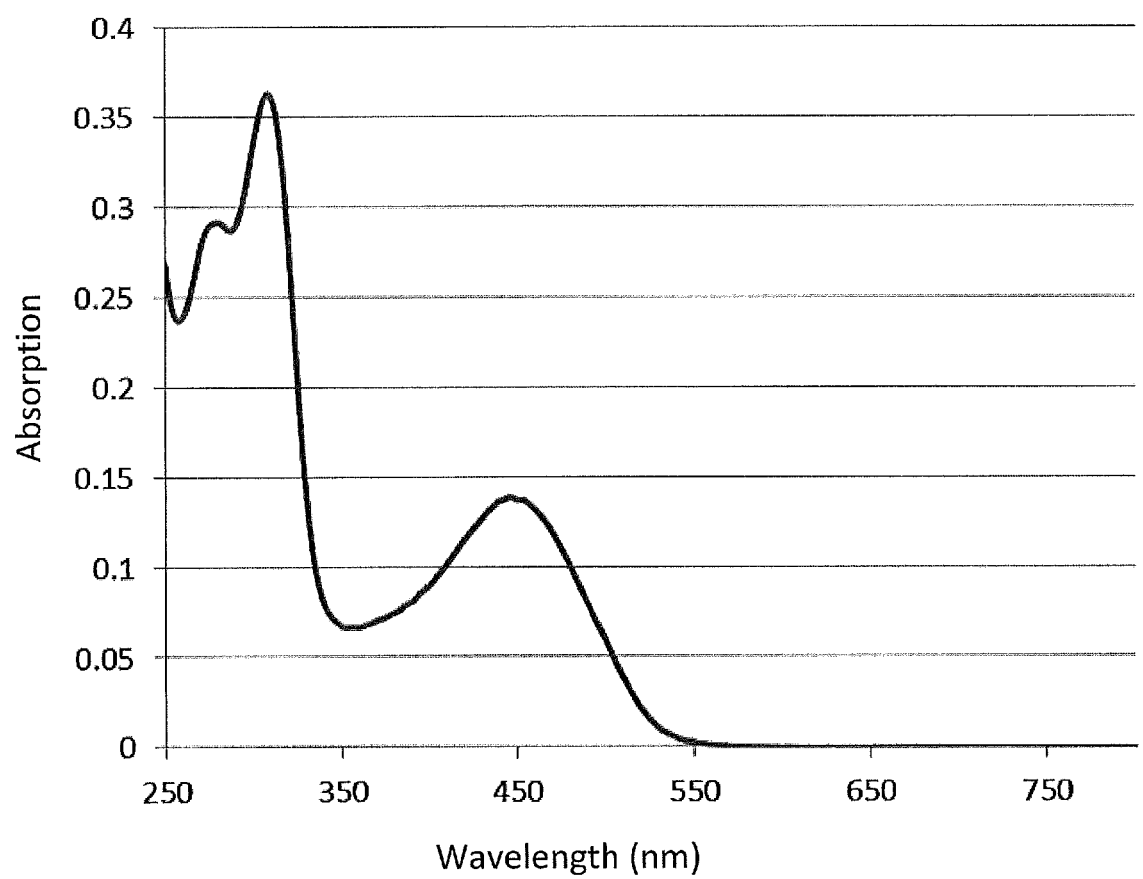
FIG. 21 shows a UV-Vis absorption spectrum of (S)-4,4',6,6'-tetrahydroxy-2,2'-dimethoxy-1,1'-binaphtho-para-quinone produced in Application Example 1.

FIG. 21 shows an UV-Vis (ultraviolet-visible) absorption spectrum of (S)-4,4',6,6'-tetrahydroxy-2,2'-dimethoxy-1,1'-binaphtho-para-quinone. The sample concentration was $1×10^{-5}$M, the cell length was 1 cm, and $λ_{max}$ was 308 nm.

Figure 22:
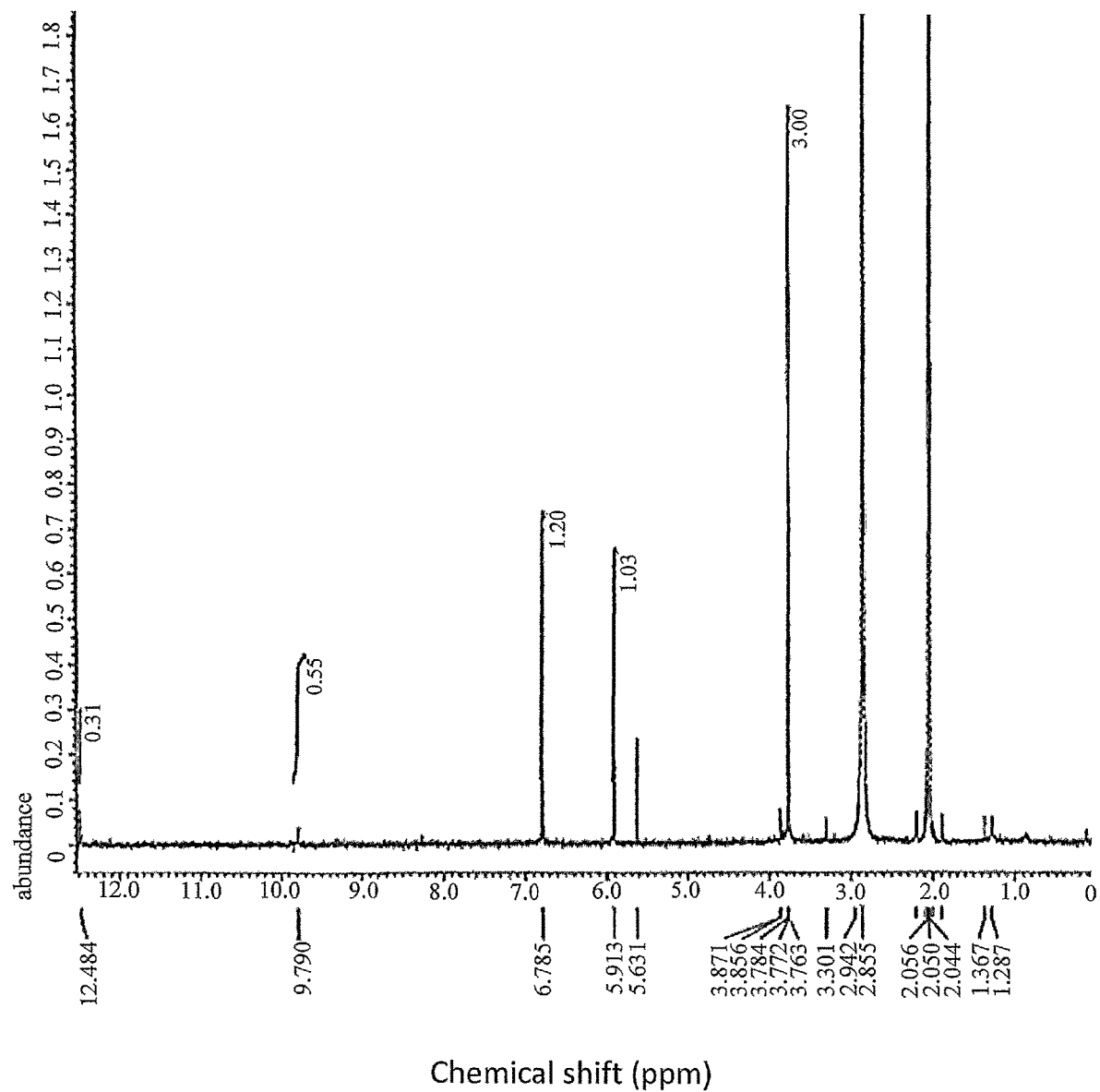
FIG. 22 shows a $^1$H-NMR profile of (S)-4,4',6,6'-tetrahydroxy-2,2'-dimethoxy-1,1'-binaphtho-para-quinone produced in Application Example 1.

The $^1$H-NMR spectrum is shown in FIG. 22.

Example 9

In Example 9, as shown in the following reaction formula, 8,8'-bis(methanesulfonyloxy)-4,4',6,6'-tetraiodo-2,2'-dimethoxy-1,1'-binaphthyl (18.1 mg, yield=18%) was obtained from (S)-4,4',6,6'-tetraiodo-2,2'-dimethoxy-1,1'-binaphthyl (81.8 mg, 0.1 mmol) in the same manner as in Example 1, except that the amount of DIH used was 76 mg (0.2 mmol) and that methanesulfonic acid (0.026 mL, 0.4 mmol) was used instead of trifluoromethanesulfonic acid. The compound obtained was a racemate and was successfully separated by a known chiral resolution technique into the (S)-isomer shown in the following reaction formula and the (R)-isomer.

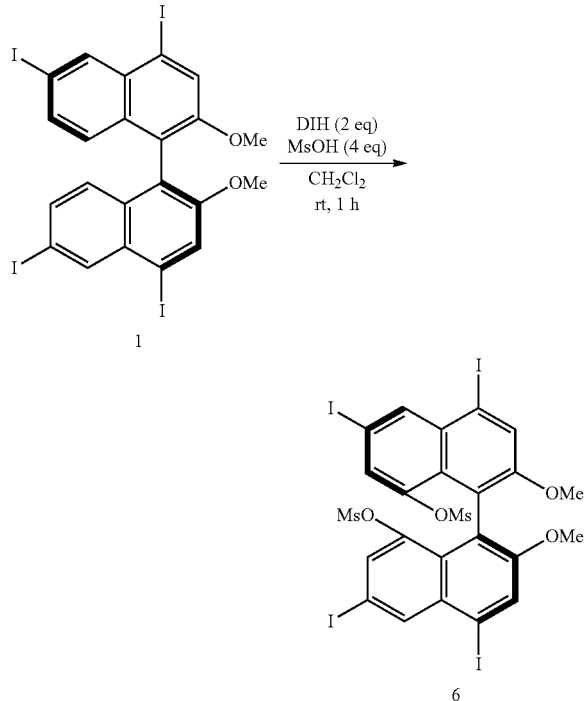

1

6

The compound obtained was identified by $^1$H-NMR spectroscopy and ASAP-MS. The chemical shifts and mass-to-charge ratios (m/z) determined are as shown below.

$^1$H-NMR: δ (ppm)=8.46 (s, 2H), 7.98 (s, 2H), 7.86 (s, 2H), 3.68 (s, 6H), 2.02 (s, 6H).

MS (ASAP): Calcd for $C_{24}H_{18}I_4O_8S_2$: m/z=1005.662, Found m/z=1005.6544.

Figure 23:
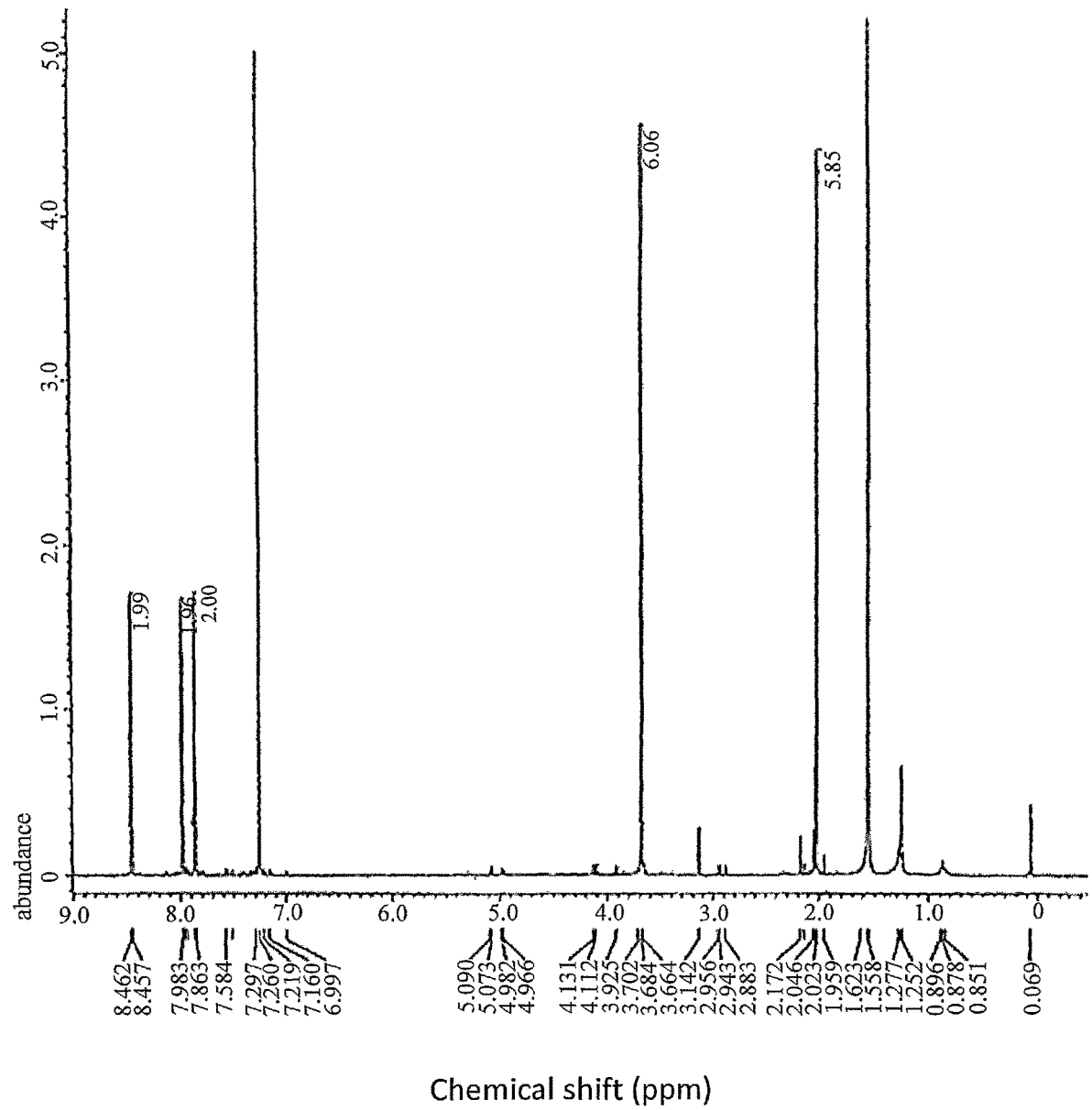
FIG. 23 shows a $^1$H-NMR profile of a 1,1'-binaphthyl derivative produced in Example 9.
Figure 24:
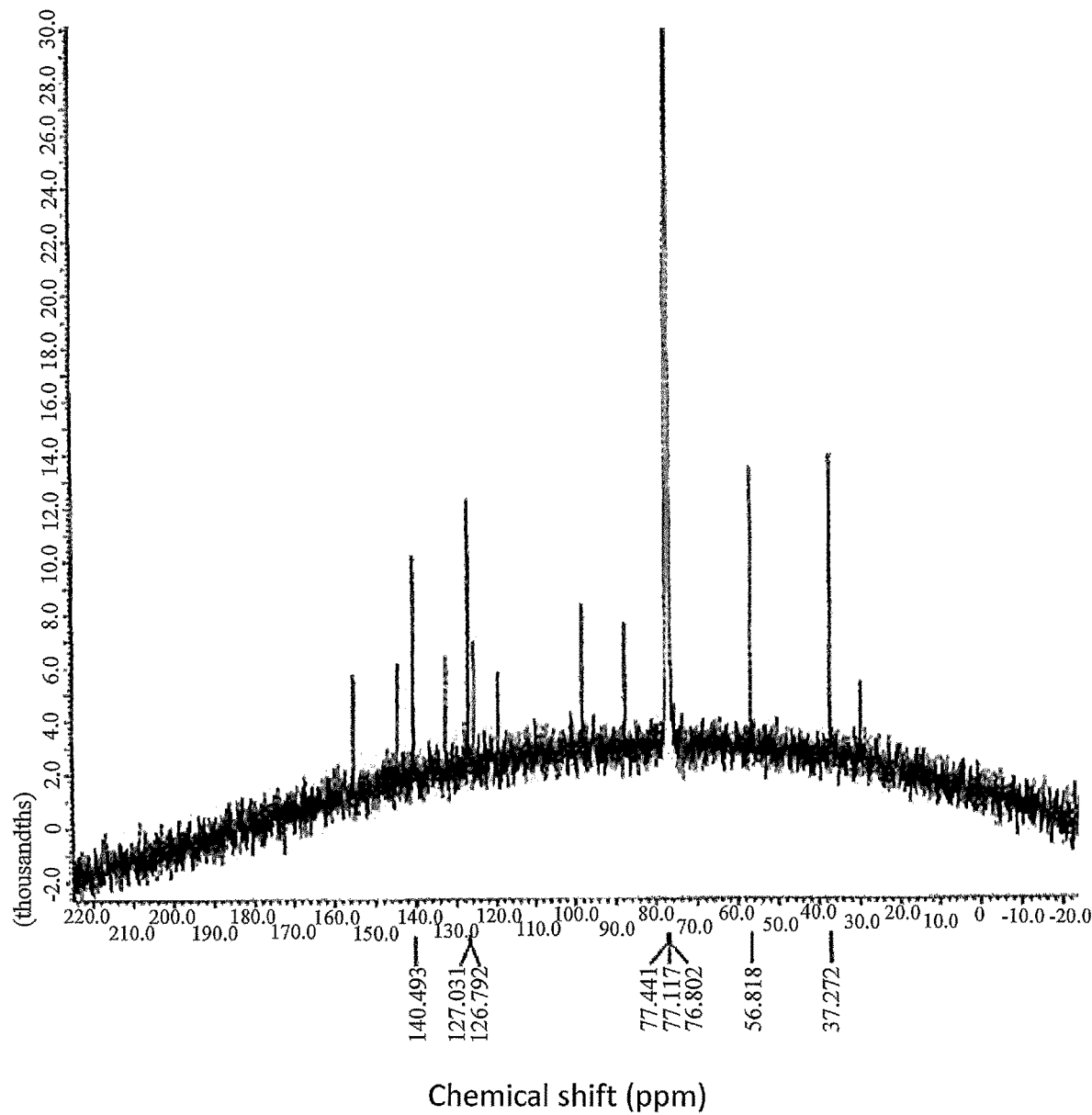
FIG. 24 shows a $^{13}$C-NMR profile of a 1,1'-binaphthyl derivative produced in Example 9.

The $^1$H-NMR spectrum is shown in FIG. 23 and a $^{13}$C-NMR spectrum is shown in FIG. 24.

Example 10

In Example 10, as shown in the following reaction formula, 5,5',6,6',8-pentaiodo-2,2'-bis(trifluoromethanesulfonyloxy)-1,1'-binaphthyl having an iodo group introduced at the 8-position and further having iodo groups introduced at the 6-position and 6'-position was synthesized from 5,5'-diiodo-2,2'-bis(trifluoromethanesulfonyloxy)-1,1'-binaphthyl. In this instance, 5,5',6,6'-tetraiodo-2,2'-bis(trifluoromethanesulfonyloxy)-1,1'-binaphthyl was also obtained.

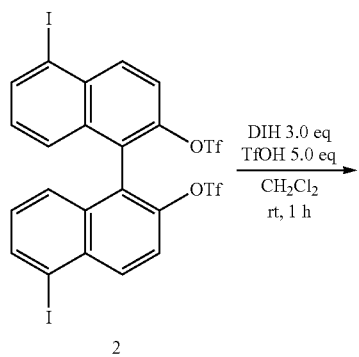

2

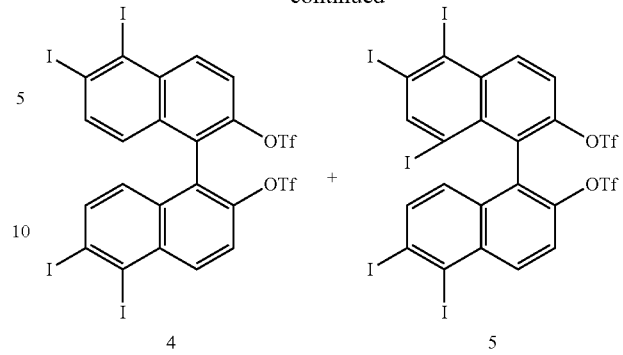

4       5

First, under air atmosphere, 5,5'-diiodo-2,2'-bis(trifluoromethanesulfonyloxy)-1,1'-binaphthyl (40.1 mg, 0.05 mmol) and DIH (57.0 mg, 0.15 mmol) were dissolved in methylene chloride (5 mL), then trifluoromethanesulfonic acid (0.022 mL, 0.25 mmol) was added dropwise to the resulting solution, and the whole system was stirred at room temperature for 1 hour. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by gel filtration chromatography to obtain 5,5',6,6',8-pentaiodo-2,2'-bis(trifluoromethanesulfonyloxy)-1,1'-binaphthyl. 5,5',6,6',8-pentaiodo-2,2'-bis(trifluoromethanesulfonyloxy)-1,1'-binaphthyl thus obtained was a racemate and was successfully separated by a known chiral resolution technique into the (R)-isomer and the (S)-isomer.

5,5',6,6',8-pentaiodo-2,2'-bis(trifluoromethanesulfonyloxy)-1,1'-binaphthyl obtained was identified by $^1$H-NMR spectroscopy, $^{13}$C-NMR spectroscopy, $^{19}$F-NMR spectroscopy, and ASAP-MS. The chemical shifts and mass-to-charge ratios (m/z) determined are as shown below.

$^1$H-NMR: δ (ppm)=8.691 (d, J=9.6 Hz, 1H), 8.581 (d, J=8.8 Hz, 1H), 7.824 (d, J=8.8 Hz, 1H), 7.788 (s, 1H), 7.616 (d, J=9.6 Hz, 1H), 7.577 (d, J=9.6 Hz, 1H), 6.846 (d, J=9.2 Hz, 1H).

$^{13}$C-NMR: δ (ppm)=107.823, 112.066, 114.412, 114.650, 116.395, 119.865, 122.173, 122.297, 122.678, 122.802, 126.473, 127.779, 131.698, 133.214, 134.673, 135.836, 137.304, 138.401, 140.946, 142.176, 146.124, 146.200.

$^{19}$F-NMR: δ (ppm)=−73.936, −74.028 MS (ASAP): Calcd for $C_{22}H_7F_6I_5O_6S_2$: m/z=1179.48, Found m/z=1179.2793.

Figure 25:
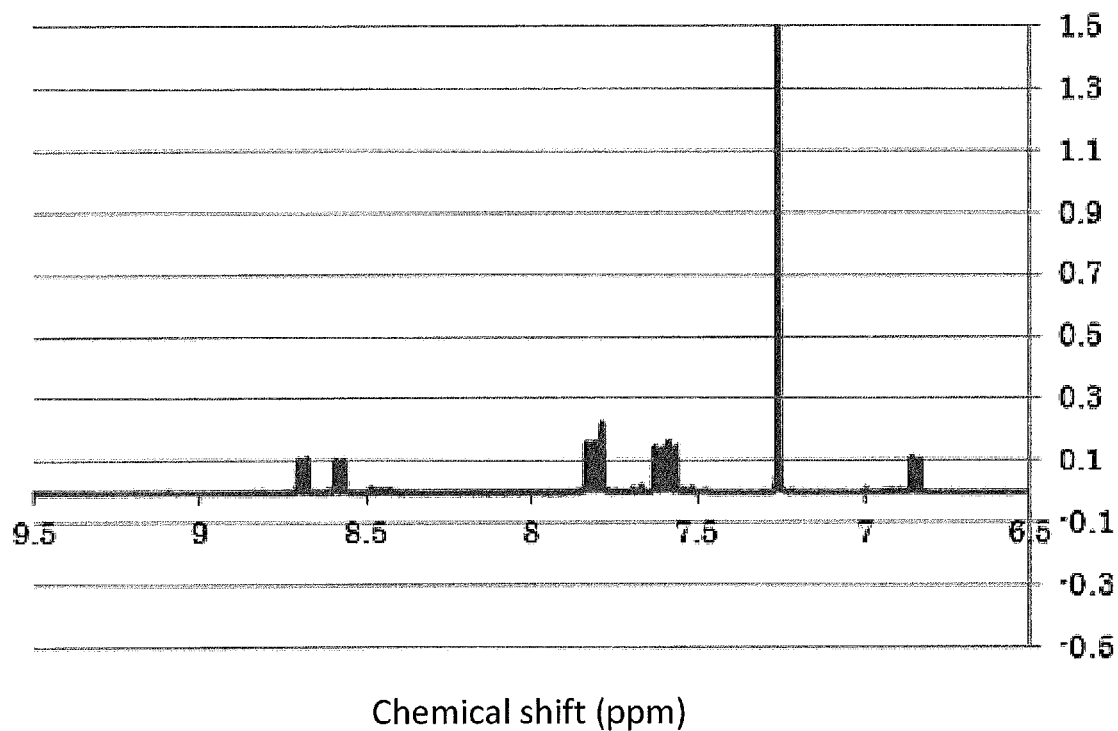
FIG. 25 shows a $^1$H-NMR profile of a 1,1'-binaphthyl derivative produced in Example 10.
Figure 26:
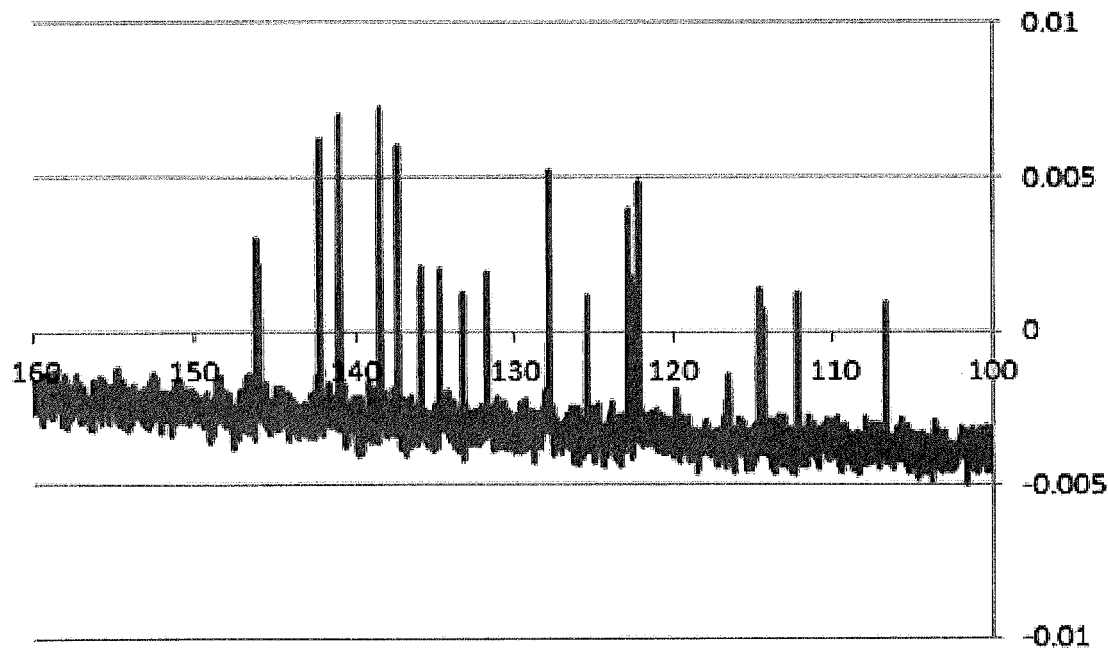
FIG. 26 shows a $^{13}$C-NMR profile of a 1,1'-binaphthyl derivative produced in Example 10.
Figure 27:
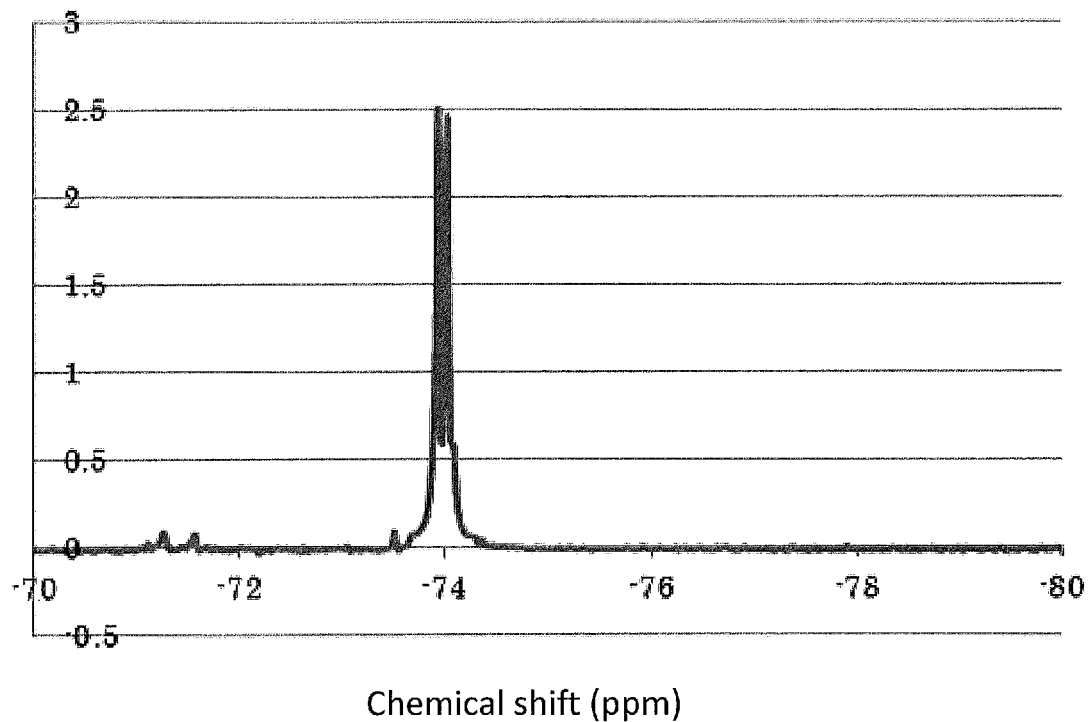
FIG. 27 shows a $^{19}$F-NMR profile of a 1,1'-binaphthyl derivative produced in Example 10.

The $^1$H-NMR spectrum is shown in FIG. 25, the $^{13}$C-NMR spectrum is shown in FIG. 26, and the $^{19}$F-NMR spectrum is shown in FIG. 27.

Example 11

In Example 11, as shown in the following reaction formula, 1,3,4,6,7,9,10,12-octa(trifluoromethanesulfonyloxy)perylene and 1,3,4,6,7,9,12-hepta(trifluoromethanesulfonyloxy)perylene or 1,3,4,6,7,9,10-hepta(trifluoromethanesulfonyloxy)perylene, which are perylene derivatives, were synthesized from (S)-2,2'-bis(trifluoromethanesulfonyloxy)-1,1'-binaphthyl. In this instance, 5,5',6,6'-tetraiodo-2,2',8,8'-tetra(trifluoromethanesulfonyloxy)-1,1'-binaphthyl was also obtained.

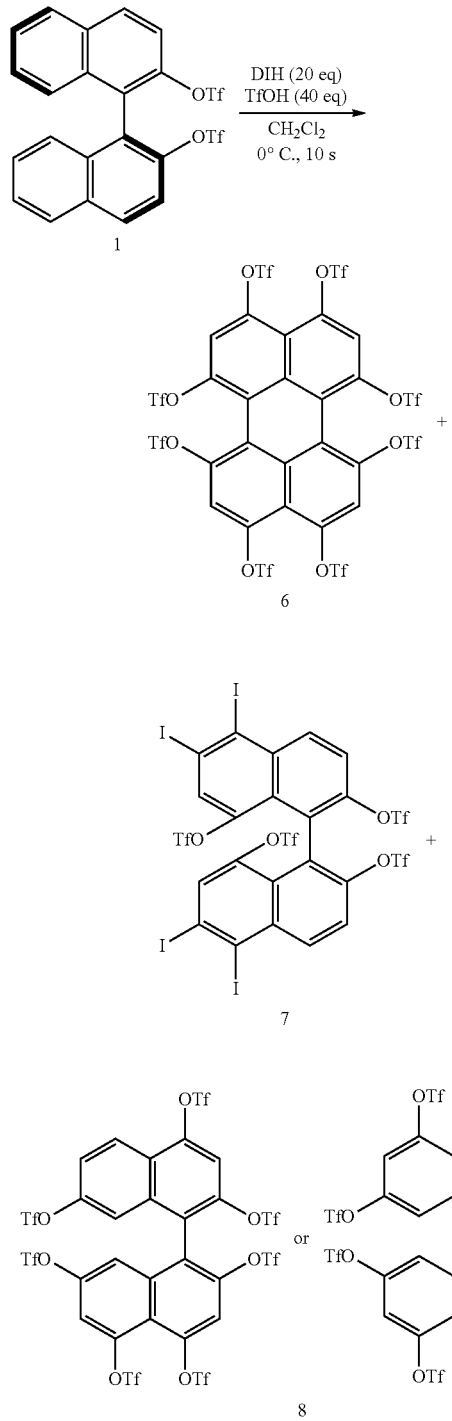

First, under air atmosphere, (S)-2,2'-bis(trifluoromethanesulfonyloxy)-1,1'-binaphthyl (55.0 mg, 0.1 mmol) and DIH (759.8 mg, 2.0 mmol) were dissolved in methylene chloride (10 mL), then trifluoromethanesulfonic acid (0.354 mL, 4.0 mmol) was added dropwise to the resulting solution, and the whole system was stirred at 0° C. for 10 seconds. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by gel filtration chromatography, followed by silica gel column chromatography (AcOEt:Hexane=1:5) for isolation to obtain 1,3,4,6,7,9,10,12-octa(trifluoromethanesulfonyloxy)perylene and 1,3,4,6,7,9,12-hepta(trifluoromethanesulfonyloxy)perylene or 1,3,4,6,7,9,10-hepta(trifluoromethanesulfonyloxy)perylene as perylene derivatives. The NMR ratio between 1,3,4,6,7,9,10,12-octa(trifluoromethanesulfonyloxy)perylene, and 1,3,4,6,7,9,12-hepta(trifluoromethanesulfonyloxy)perylene or 1,3,4,6,7,9,10-hepta(trifluoromethanesulfonyloxy)perylene was 0.51:1.

1,3,4,6,7,9,12-hepta(trifluoromethanesulfonyloxy)perylene or 1,3,4,6,7,9,10-hepta(trifluoromethanesulfonyloxy)perylene thus obtained was identified by $^1$H-NMR spectroscopy, $^{13}$C-NMR spectroscopy, $^{19}$F-NMR spectroscopy, and ASAP-MS. The chemical shifts and mass-to-charge ratios (m/z) determined are as shown below.

$^1$H-NMR: δ (ppm)=8.804 (d, J=8.4 Hz, 1H), 7.914 (d, J=8.4 Hz, 1H), 7.840 (s, 1H), 7.767 (s, 1H), 7.764 (s, 1H).

$^{13}$C-NMR: δ (ppm)=113.849, 114.192, 117.196, 118.016, 118.435, 118.569, 119.217, 119.408, 119.694, 120.399, 122.535, 123.336, 124.985, 131.212, 132.079, 132.737, 142.977, 143.931, 144.169, 144.398, 144.808, 145.485.

$^{19}$F-NMR: δ (ppm)=−71.631, −71.724, −71.785, −71.939, −72.707, −72.768, −72.861.

MS (ASAP): Calcd for $C_{27}H_5F_{21}O_{21}S_7$: m/z=1287.7, Found m/z=1287.6708.

Figure 28:
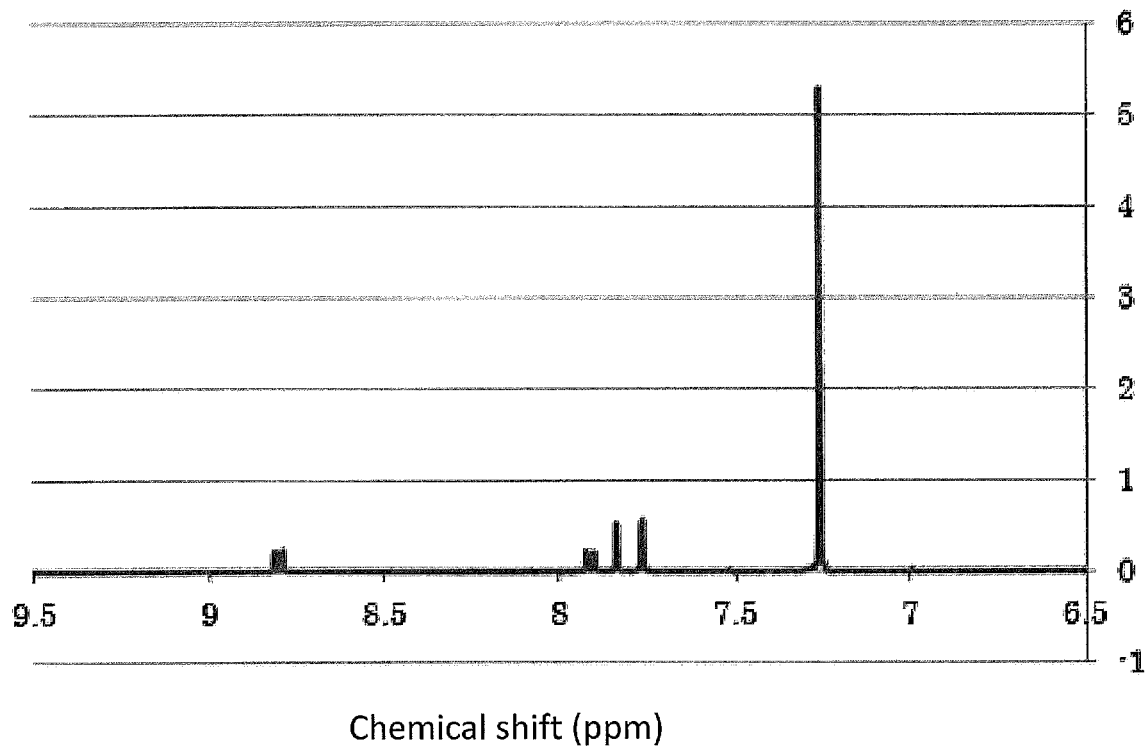
FIG. 28 shows a $^1$H-NMR profile of a perylene derivative produced in Example 11.
Figure 29:
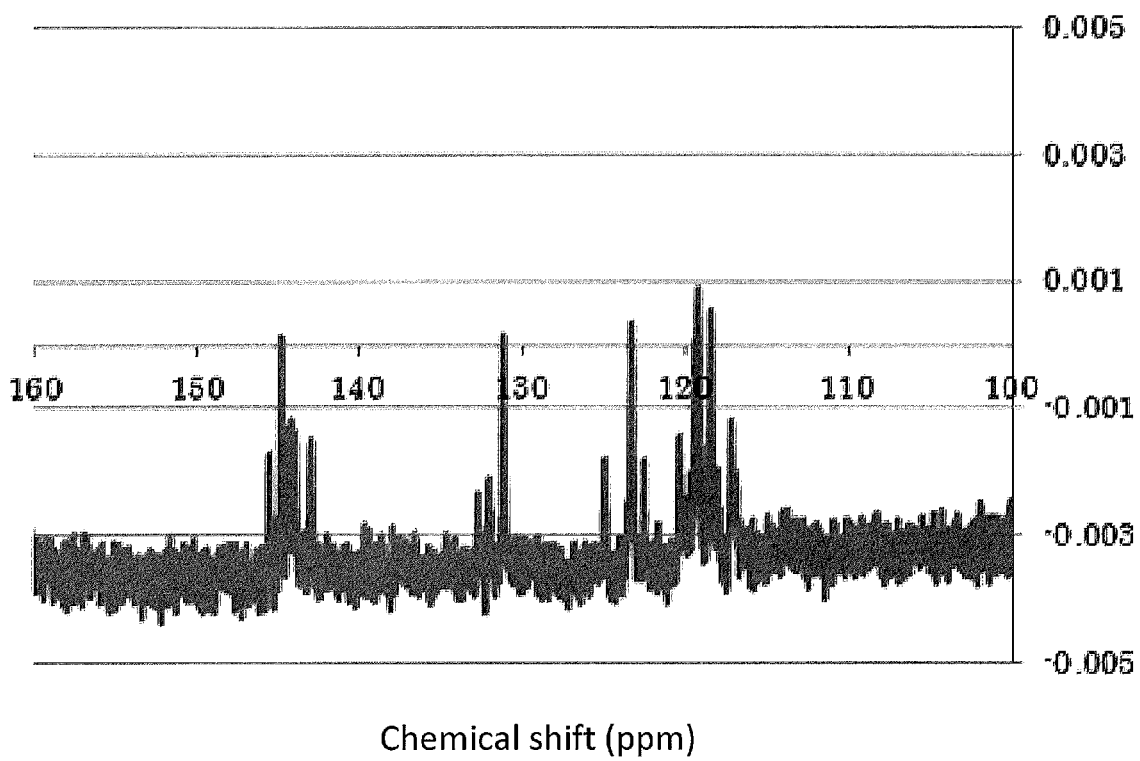
FIG. 29 shows a $^{13}$C-NMR profile of a perylene derivative produced in Example 11.
Figure 30:
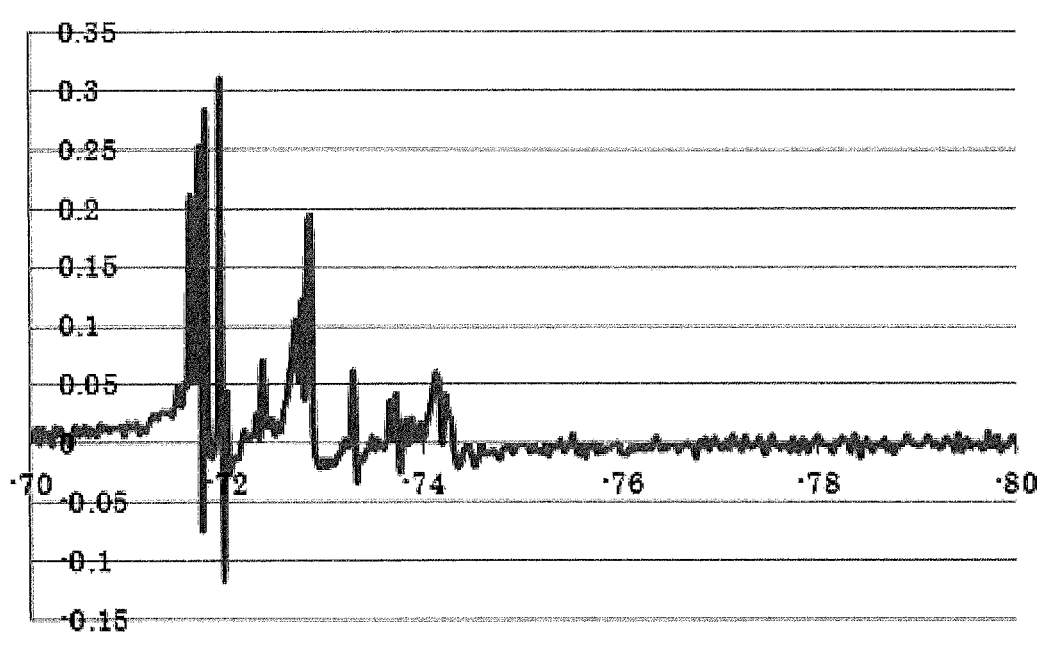
FIG. 30 shows a $^{19}$F-NMR profile of a perylene derivative produced in Example 11.

The $^1$H-NMR spectrum is shown in FIG. 28, the $^{13}$C-NMR spectrum is shown in FIG. 29, and the $^{19}$F-NMR spectrum is shown in FIG. 30.

Example 12

In Example 12, as shown in the following reaction formula, 1,12-diiodo-3,4,5,6,7,9,10-hepta(trifluoromethanesulfonyloxy)perylene which is a perylene derivative was synthesized from (S)-5,5',6,6'-tetraiodo-2,2'-bis(trifluoromethanesulfonyloxy)-1,1'-binaphthyl. In this instance, 5,5',6,6'-tetraiodo-2,2',8,8'-tetra(trifluoromethanesulfonyloxy)-1,1'-binaphthyl was also obtained.

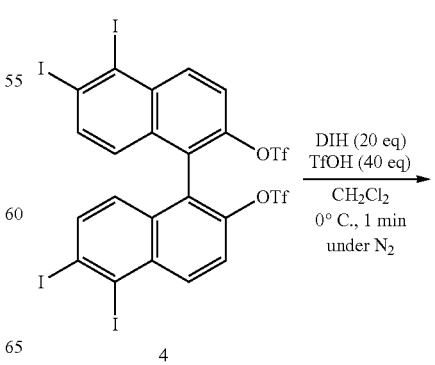

-continued

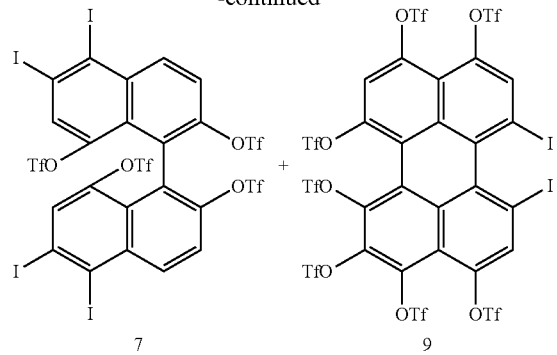

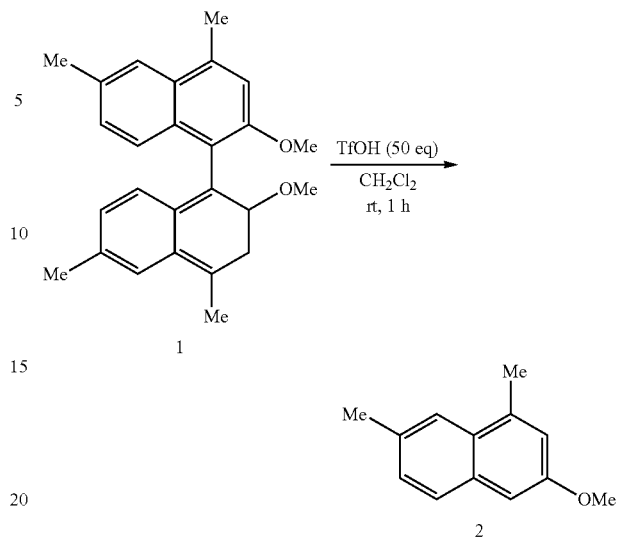

First, under nitrogen atmosphere, 5,5',6,6'-tetraiodo-2,2'-bis(trifluoromethanesulfonyloxy)-1,1'-binaphthyl (105.3 mg, 0.1 mmol) and DIH (759.8 mg, 2.0 mmol) were dissolved in methylene chloride (10 mL), then trifluoromethanesulfonic acid (0.354 mL, 4.0 mmol) was added dropwise to the resulting solution, and the whole system was stirred at 0° C. for 1 minute. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by gel filtration chromatography to obtain 1,12-diiodo-3,4,5,6,7,9,10-hepta(trifluoromethanesulfonyloxy) perylene (10.1 mg, yield=6.6%) as a perylene derivative.

1,12-diiodo-3,4,5,6,7,9,10-hepta(trifluoromethanesulfonyloxy)perylene thus obtained was identified by $^1$H-NMR spectroscopy, $^{13}$C-NMR spectroscopy, $^{19}$F-NMR spectroscopy, and ASAP-MS. The chemical shifts and mass-to-charge ratios (m/z) determined are as shown below.

$^1$H-NMR: δ (ppm)=8.976 (s, 1H), 7.717 (s, 1H), 7.707 (s, 1H).

$^{13}$C-NMR: δ (ppm)=118.836, 119.637.

$^{19}$F-NMR: δ (ppm)=−71.216, −71.508, −71.662 (s, 2F), −72.277, −72.707, −72.768.

MS (ASAP): Calcd for $C_{27}H_3F_{21}I_2O_{21}S_7$: m/z=1539.5, Found m/z=1539.3623.

Figure 31:
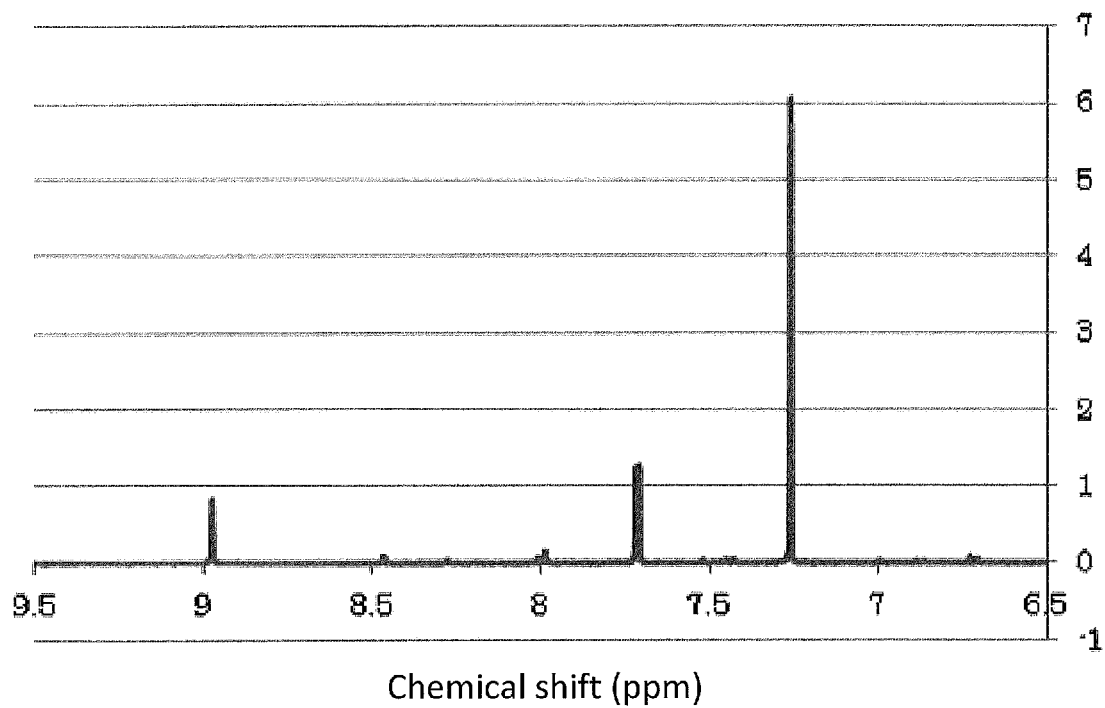
FIG. 31 shows a $^1$H-NMR profile of a perylene derivative produced in Example 12.
Figure 32:
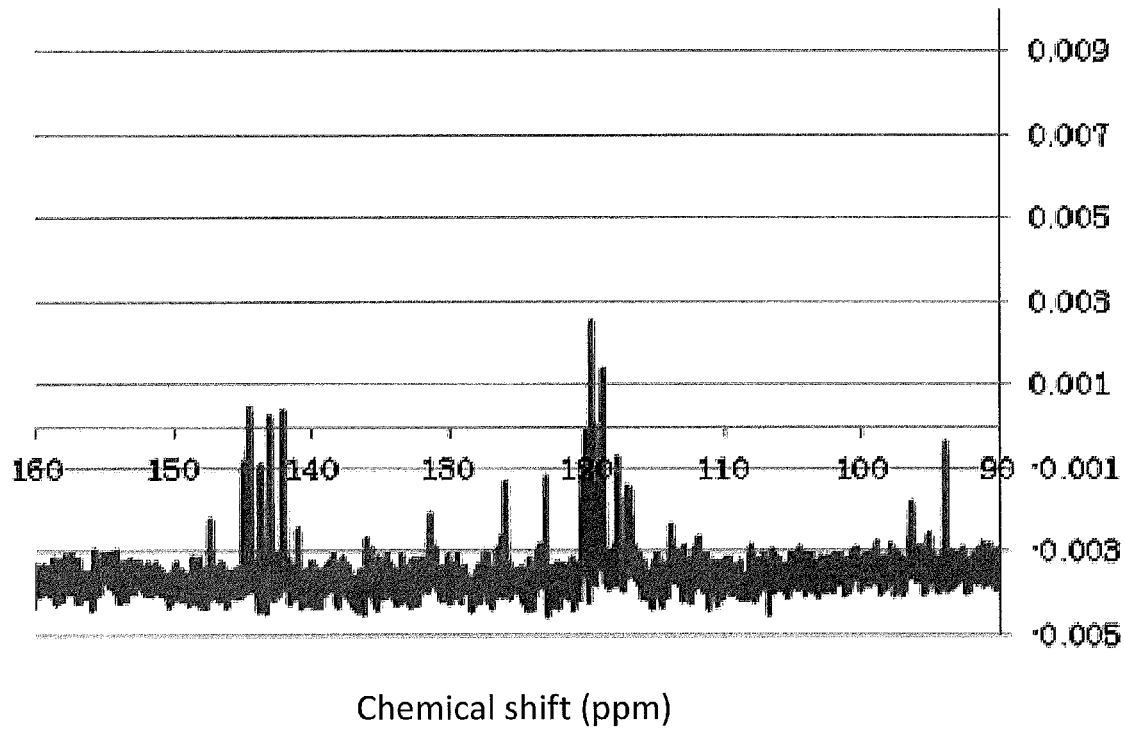
FIG. 32 shows a $^{13}$C-NMR profile of a perylene derivative produced in Example 12.
Figure 33:
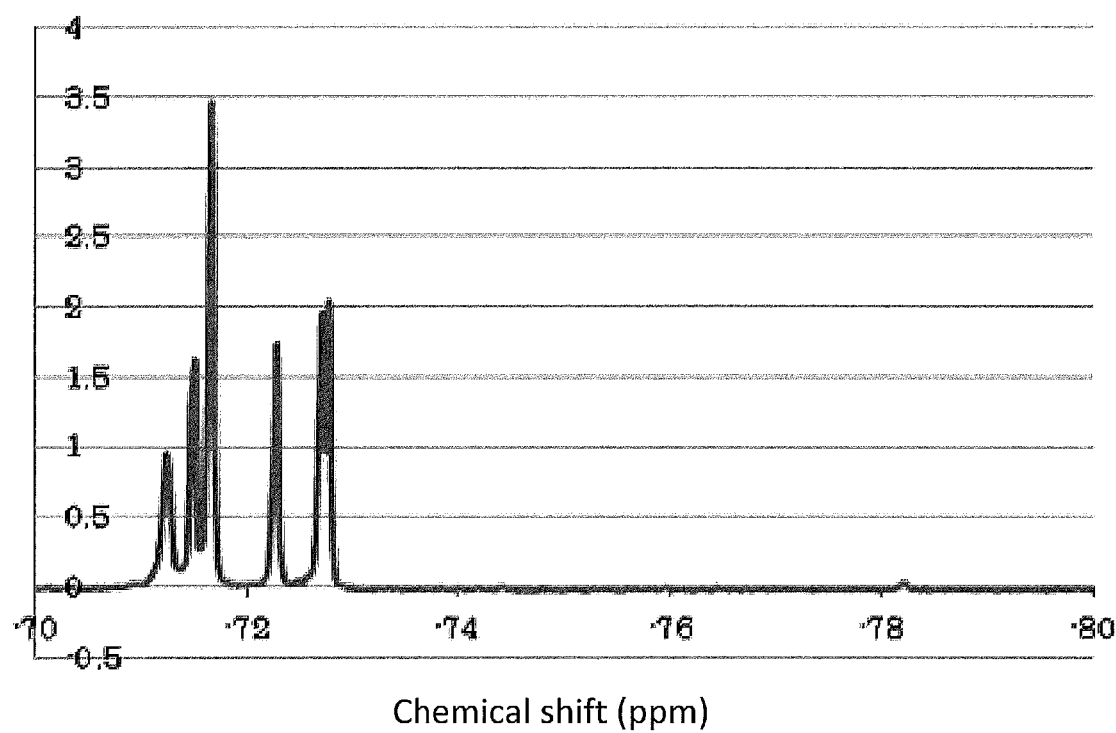
FIG. 33 shows a $^{19}$F-NMR profile of a perylene derivative produced in Example 12.

The $^1$H-NMR spectrum is shown in FIG. 31, the $^{13}$C-NMR spectrum is shown in FIG. 32, and the $^{19}$F-NMR spectrum is shown in FIG. 33.

Experimental Example 1

In Experimental Example 1, as shown in the following reaction formula, 4,4',6,6'-tetramethyl-2,2'-dimethoxy-1,1'-binaphthyl was decoupled (cleaved) to obtain 2-methoxy-4,6-dimethylnaphthalene.

First, under air atmosphere, 4,4',6,6'-tetramethyl-2,2'-dimethoxy-1,1'-binaphthyl (74 mg, 0.2 mmol) was dissolved in methylene chloride (10 mL), then trifluoromethanesulfonic acid (0.885 mL, 10 mmol) was added dropwise to the resulting solution, which was stirred at room temperature for 1 hour. After the stirring, excessive amounts of saturated aqueous solution of sodium hydrogen carbonate and saturated aqueous solution of sodium sulfite were added to the reaction mixture. Next, an organic phase was extracted with methylene chloride, and the extracted organic phase was dried over magnesium sulfate. The dried organic phase was filtered and concentrated to obtain a crude product. Next, the obtained crude product was subjected to filtration with hexane, followed by concentration and then by silica gel column chromatography (AcOEt:Hexane=1:5) for isolation. As a result, 2-methoxy-4,6-dimethylnaphthalene was obtained (35 mg, yield=47%).

2-methoxy-4,6-dimethylnaphthalene thus obtained was identified by $^1$H-NMR spectroscopy, $^{13}$C-NMR spectroscopy, and ASAP-MS. The chemical shifts and mass-to-charge ratios (m/z) determined are as shown below.

$^1$H-NMR: δ (ppm)=7.712 (s, H), 7.682 (d, 1H), 7.329 (d, 1H), 7.021 (s, 1H), 7.007 (s, 1H), 3.922 (s, 3H), 2.667 (s, 3H), 2.555 (s, 3H).

$^{13}$C-NMR: δ (ppm)=156.578, 135.526, 132.904, 128.527, 128.318, 127.298, 123.303, 119.374, 103.842, 55.159, 21.864, 19.376.

MS (ASAP): Calcd for $C_{13}H_{14}O$: m/z=186.1045, Found m/z=186.1567.

Figure 34:
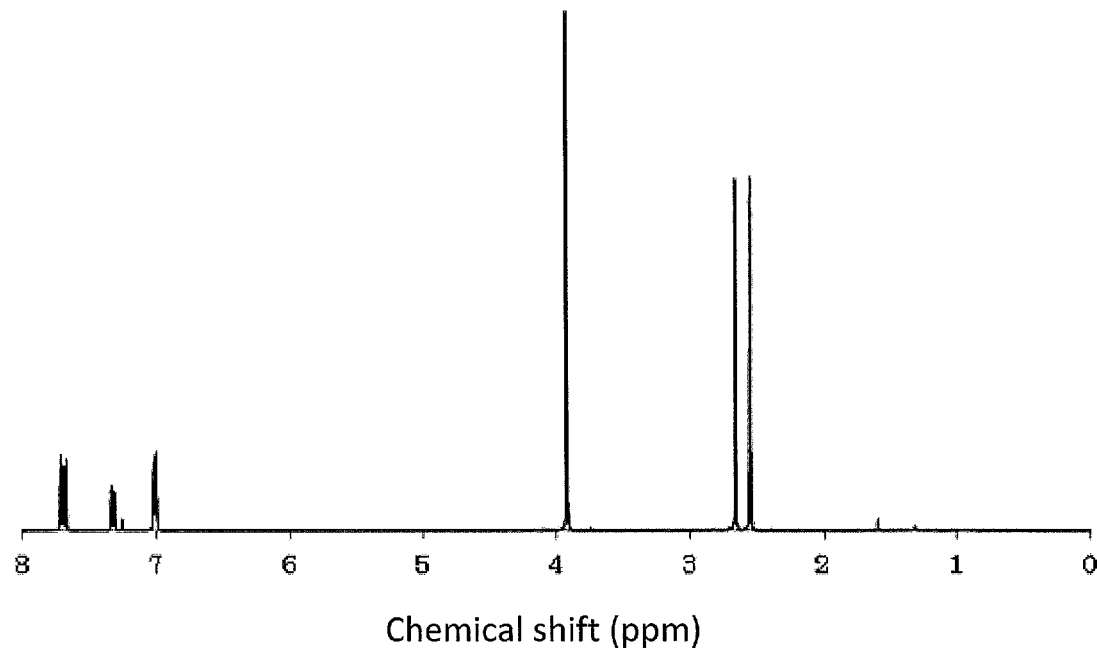
FIG. 34 shows a $^1$H-NMR profile of a naphthalene derivative produced in Experimental Example 1.
Figure 35:
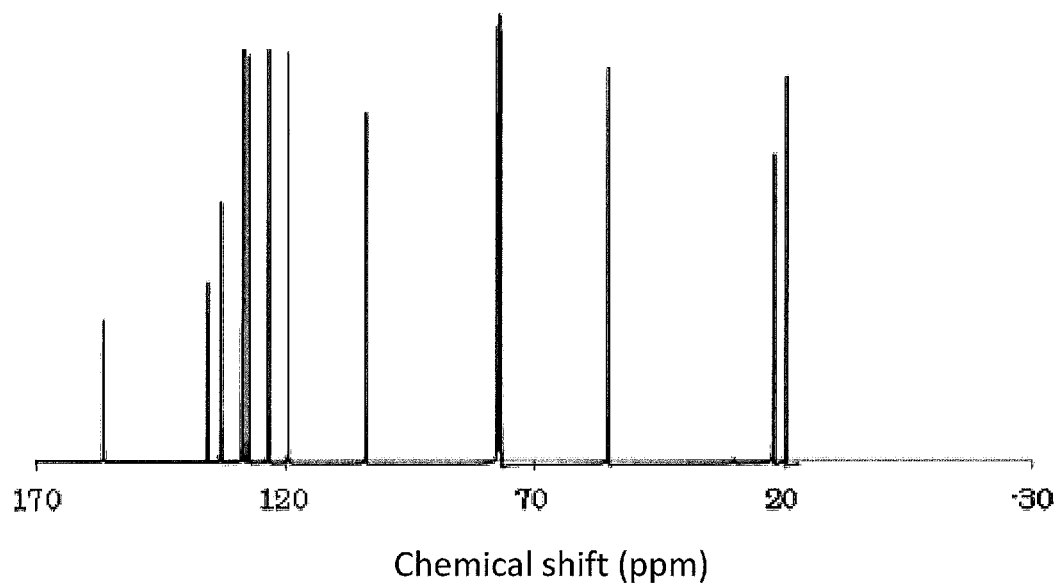
FIG. 35 shows a $^{13}$C-NMR profile of a naphthalene derivative produced in Experimental Example 1.

The $^1$H-NMR spectrum is shown in FIG. 34, and the $^{13}$C-NMR spectrum is shown in FIG. 35.

Example 13

In Example 13, as shown in the following reaction formula, 1-(2-methoxy-4,5,6,8-tetrakis(trifluoromethanesulfonyloxy)-2-methoxy-6-iodo-5,8-di-oxo-4,7-bis(trifluoromethanesulfonyloxy)-naphthoquinone which is a binaphthyl derivative having a quinone structure was synthesized from (S)-2,2'-dimethoxy-1,1'-binaphthyl.

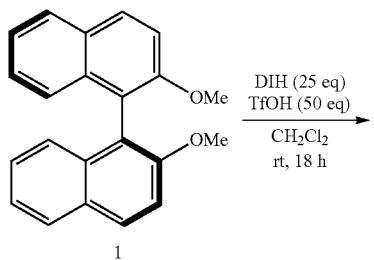

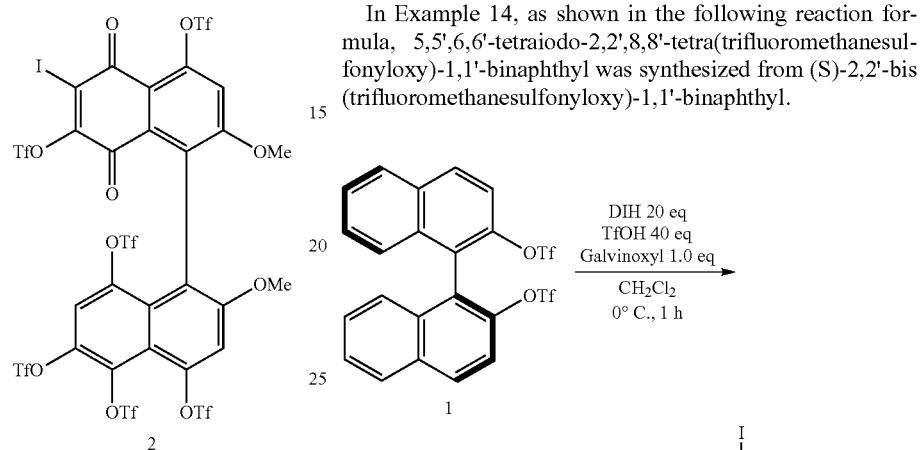

First, under air atmosphere, (S)-2,2'-dimethoxy-1,1'-binaphthyl (62.8 mg, 0.2 mmol) and DIH (1900 mg, 5 mmol) were dissolved in methylene chloride (30 mL), then trifluoromethanesulfonic acid (0.885 mL, 10 mmol) was added dropwise to the resulting solution, and the whole system was stirred at room temperature for 18 hours. After the stirring, excessive amounts of saturated aqueous solution of sodium hydrogen carbonate and saturated aqueous solution of sodium sulfite were added to the reaction mixture. Next, an organic phase was extracted with methylene chloride, and the extracted organic phase was dried over magnesium sulfate. The dried organic phase was filtered and concentrated to obtain a crude product. After that, the obtained crude product was purified by silica gel column chromatography (AcOEt:Hexane=1:5) to obtain 1-(2-methoxy-4,5,6,8-tetrakis(trifluoromethanesulfonyloxy)-2-methoxy-6-iodo-5,8-di-oxo-4,7-bis(trifluoromethanesulfonyloxy)-naphthoquinone (52 mg, yield=20%). The compound obtained was a racemate and was successfully separated by a known chiral resolution technique into the (R)-isomer and the (S)-isomer.

1-(2-methoxy-4,5,6,8-tetrakis(trifluoromethanesulfonyloxy)-2-methoxy-6-iodo-5,8-dioxo-4,7-bis(trifluoromethanesulfonyloxy)-naphthoquinone thus obtained was identified by $^1$H-NMR spectroscopy, $^{13}$C-NMR spectroscopy, $^{19}$F-NMR spectroscopy and ASAP-MS. The chemical shifts and mass-to-charge ratios (m/z) determined are as shown below.

$^1$H-NMR: δ (ppm)=7.601 (s, 2H), 7.535 (s, 2H), 7.136 (s, 2H), 3.866 (s, 3H), 3.818 (s, 3H).

$^{13}$C-NMR: δ (ppm)=175.113 (s, 1C), 173.931 (s, 1C), 162.919 (s, 1C), 156.206 (s, 1C), 155.930 (s, 1C), 150.171 (s, 1C), 144.984 (s, 1C), 143.754 (s, 1C), 137.023 (s, 1C), 133.600 (s, 1C), 130.978 (s, 1C), 126.954 (s, 1C), 126.611 (s, 1C), 118.845 (q, 1C), 118.764 (q, 1C), 118.672 (q, 1C), 118.602 (q, 1C), 118.235 (q, 1C), 117.908 (q, 1C), 117.248 (s, 1C), 116.009 (s, 1C), 115.961 (s, 1C), 115.789 (s, 1C), 114.34 (s, 1C), 111.871 (s, 1C), 110.917 (s, 1C), 57.276 (s, 1C), 57.228 (s, 1C).

$^{19}$F-NMR: δ (ppm)=−71.785, −72.031, −72.277, −72.400, −72.768, −72.598.

MS (ASAP): Calcd for $C_{28}H_9F_{18}IO_{22}S_6$: m/z=1357.6667, Found m/z=1358.7473.

Figure 36:
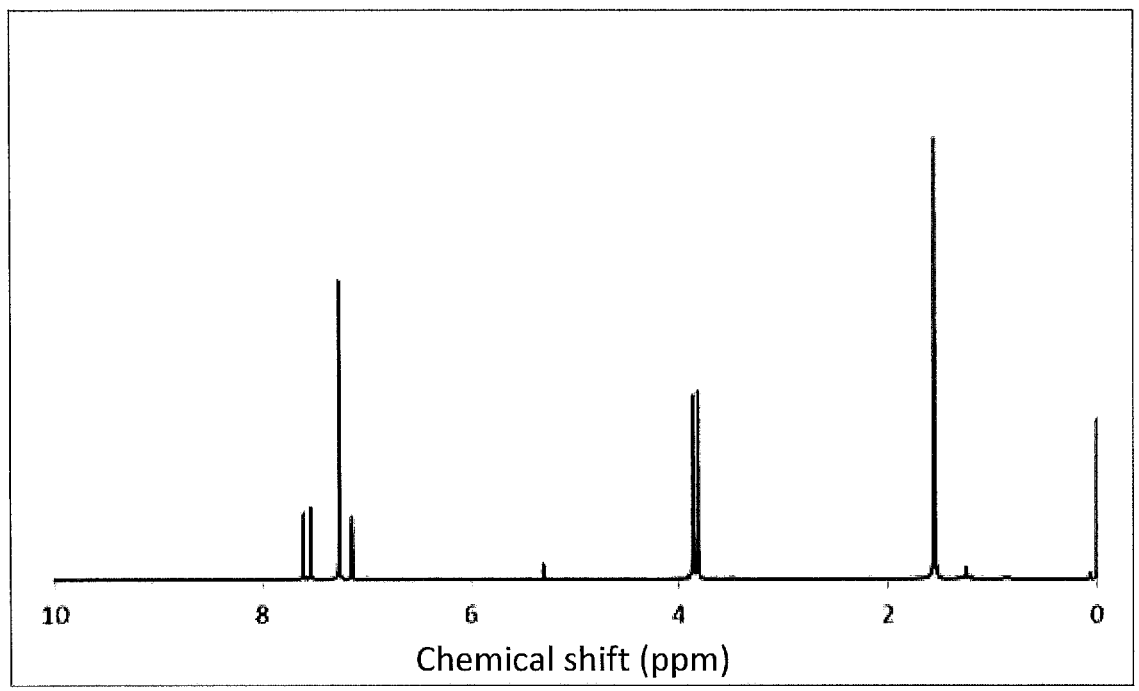
FIG. 36 shows a $^1$H-NMR profile of a 1,1'-binaphthyl derivative produced in Example 13.
Figure 37:
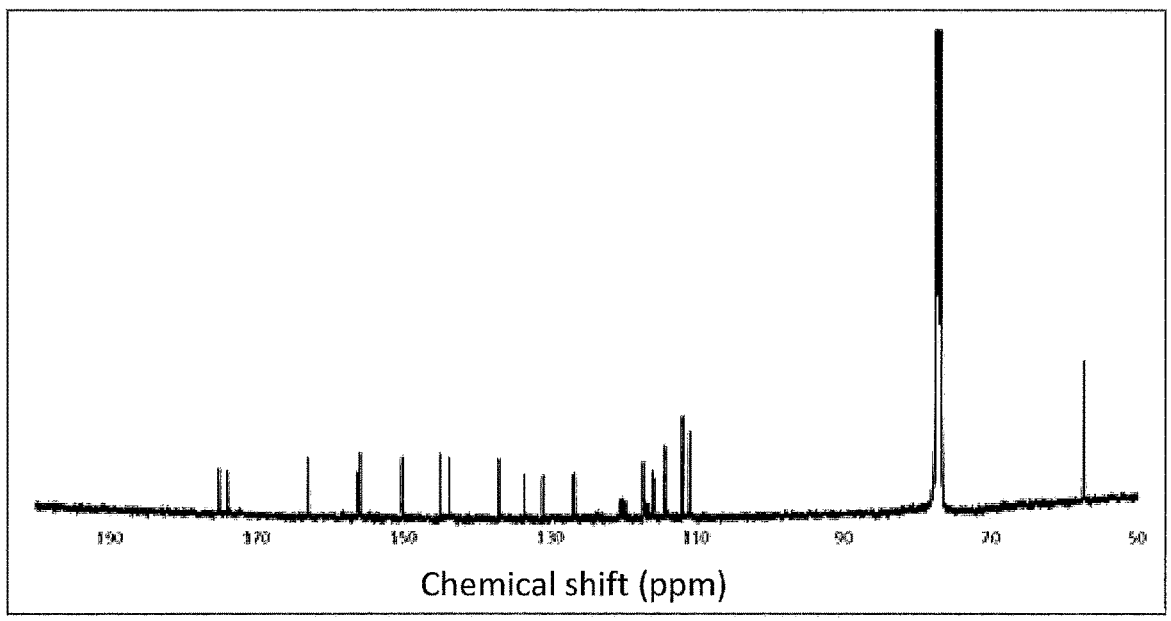
FIG. 37 shows a $^{13}$C-NMR profile of a 1,1'-binaphthyl derivative produced in Example 13.
Figure 38:
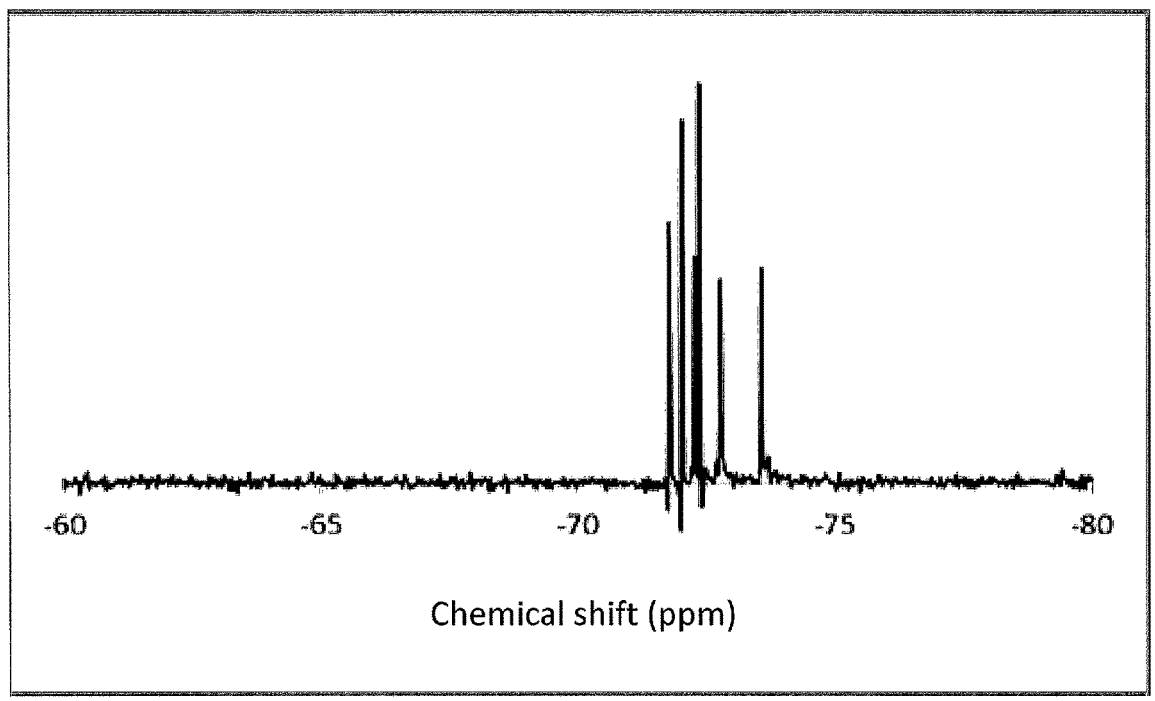
FIG. 38 shows a $^{19}$F-NMR profile of a 1,1'-binaphthyl derivative produced in Example 13.

The $^1$H-NMR spectrum is shown in FIG. 36, the $^{13}$C-NMR spectrum is shown in FIG. 37, and the $^{19}$F-NMR spectrum is shown in FIG. 38.

Example 14

In Example 14, as shown in the following reaction formula, 5,5',6,6'-tetraiodo-2,2',8,8'-tetra(trifluoromethanesulfonyloxy)-1,1'-binaphthyl was synthesized from (S)-2,2'-bis(trifluoromethanesulfonyloxy)-1,1'-binaphthyl.

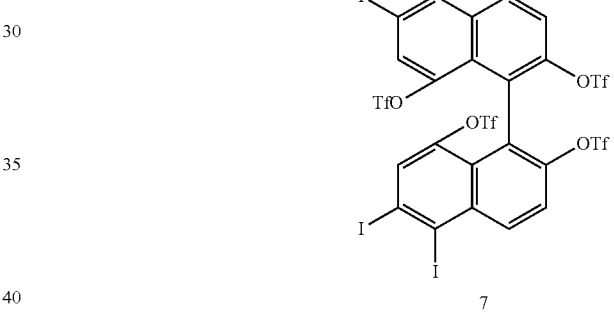

First, under nitrogen atmosphere, (S)-2,2'-bis(trifluoromethanesulfonyloxy)-1,1'-binaphthyl (55.0 mg, 0.1 mmol), DIH (759.8 mg, 2.0 mmol), and galvinoxyl as a radical scavenger (42.2 mg, 0.1 mmol) were dissolved in methylene chloride (10 mL), then trifluoromethanesulfonic acid (0.354 mL, 4.0 mmol) was added dropwise to the resulting solution, and the whole system was stirred at 0° C. for 1 hour. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and dried over magnesium sulfate. Next, the solvent was removed using an evaporator to obtain a crude product. After that, the obtained crude product was purified by silica gel column chromatography (AcOEt:Hexane=1:10) to obtain 5,5',6,6'-tetraiodo-2,2',8,8'-tetra(trifluoromethanesulfonyloxy)-1,1'-binaphthyl (71.5 mg, yield=53%). The compound obtained was a racemate and was successfully separated by a known chiral resolution technique into the (R)-isomer and the (S)-isomer.

5,5',6,6'-tetraiodo-2,2',8,8'-tetra(trifluoromethanesulfonyloxy)-1,1'-binaphthyl thus obtained was identified by $^1$H-NMR spectroscopy, $^{13}$C-NMR spectroscopy, $^{19}$F-NMR spectroscopy, and ASAP-MS, The chemical shifts and mass-to-charge ratios (m/z) determined are as shown below.

$^1$H-NMR: δ (ppm)=8.736 (d, J=9.6 Hz, 2H), 7.889 (s, 2H), 7.619 (d, J=9.6 Hz, 2H).

$^{13}$C-NMR: δ (ppm)=108.529, 113.992, 116.280, 119.465, 121.658, 122.850, 124.204, 128.027, 136.579, 141.490, 145.685, 146.505.

$^{19}$F-NMR: δ (ppm)=−74.059, −74.274.

MS (ASAP): Calcd for $C_{24}H_6F_{12}I_4O_{12}S_4$: m/z=1349.47, Found m/z=1349.6476.

Figure 39:
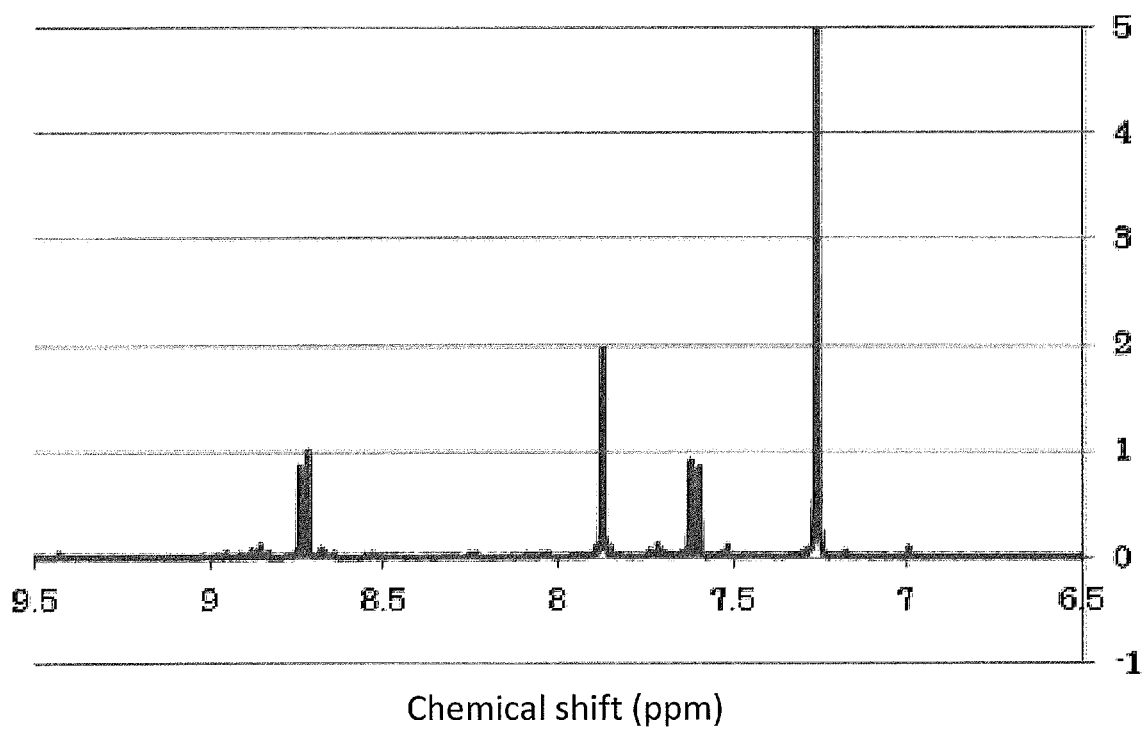
FIG. 39 shows a $^1$H-NMR profile of a 1,1'-binaphthyl derivative produced in Example 14.
Figure 40:
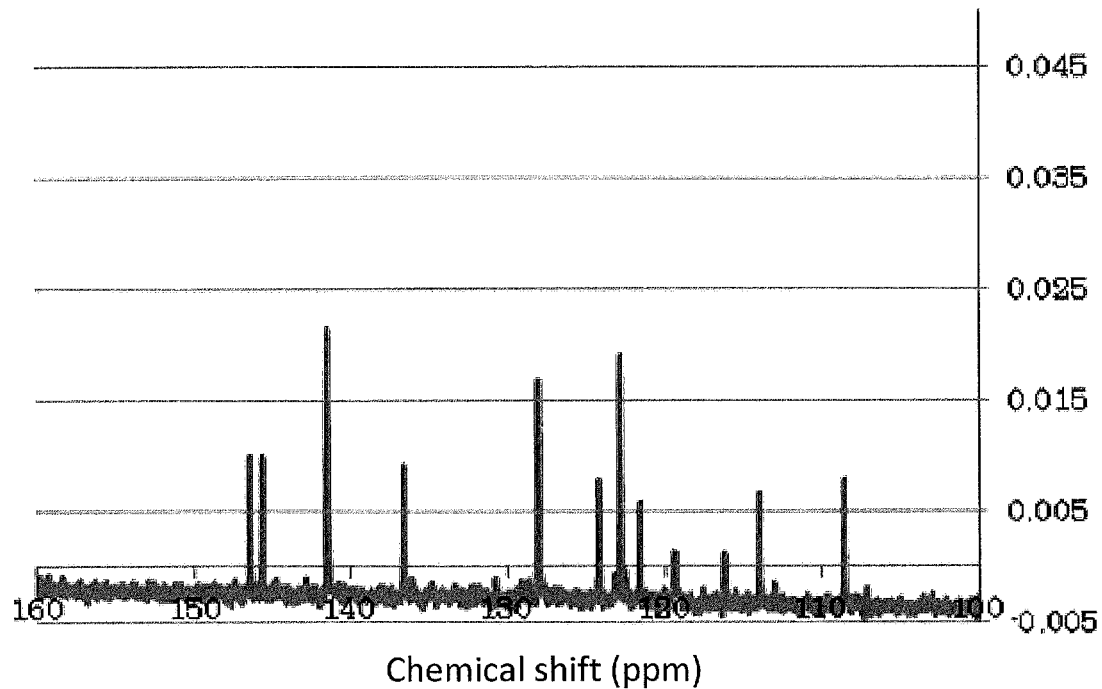
FIG. 40 shows a $^{13}$C-NMR profile of a 1,1'-binaphthyl derivative produced in Example 14.
Figure 41:
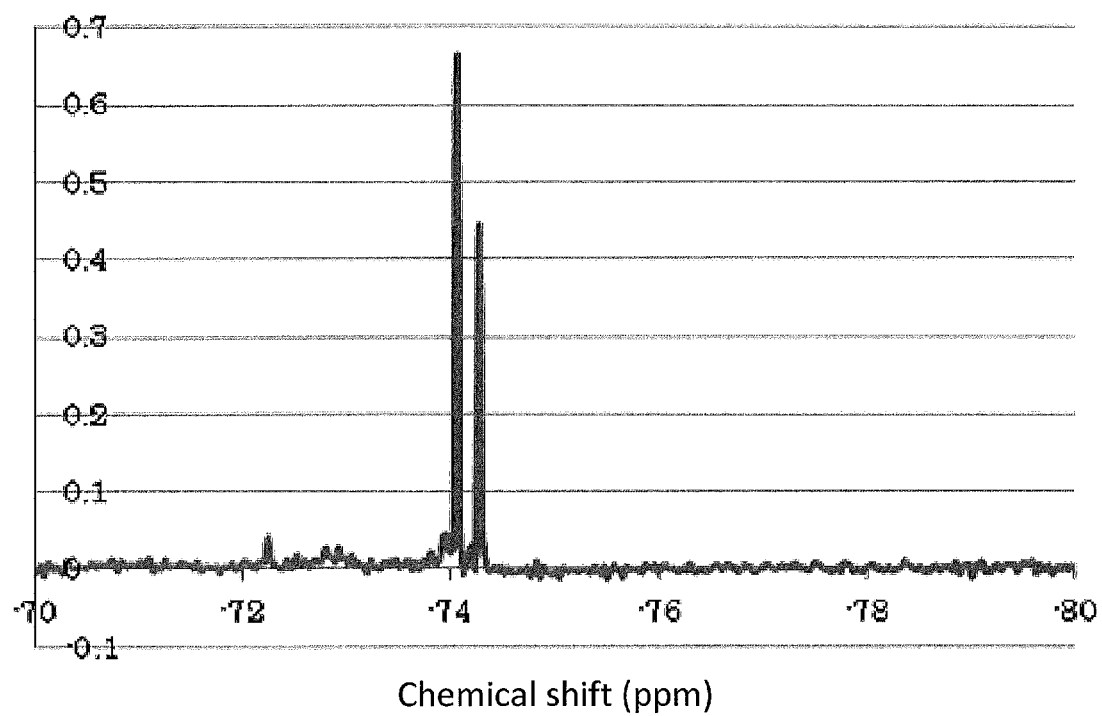
FIG. 41 shows a $^{19}$F-NMR profile of a 1,1'-binaphthyl derivative produced in Example 14.

The $^1$H-NMR spectrum is shown in FIG. 39, the $^{13}$C-NMR spectrum is shown in FIG. 40, and the $^{19}$F-NMR spectrum is shown in FIG. 41.

Example 15

In Example 15, as shown in the following reaction formula, 1,3,4,6,7,9,10,12-octa(trifluoromethanesulfonyloxy)perylene which is a perylene derivative was synthesized from (S)-2,2'-bis(trifluoromethanesulfonyloxy)-1,1'-binaphthyl. In this instance, 5,5',6,6'-tetraiodo-2,2',8,8'-tetra(trifluoromethanesulfonyloxy)-1,1'-binaphthyl was also obtained.

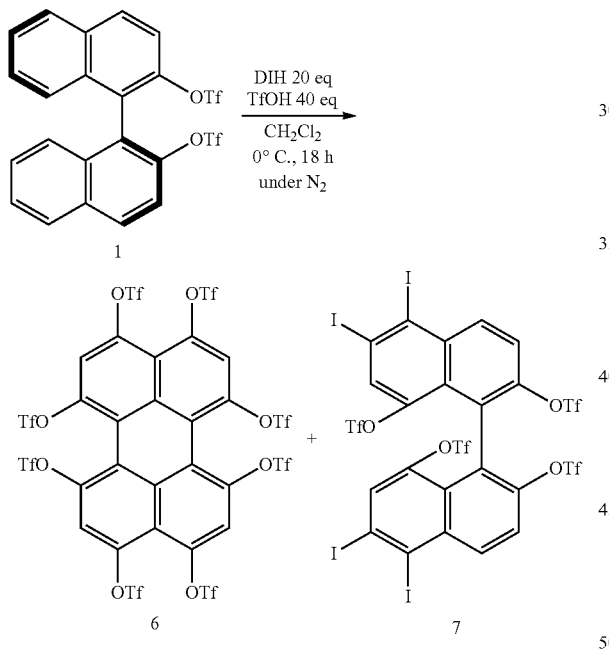

First, under nitrogen atmosphere, (S)-2,2'-bis(trifluoromethanesulfonyloxy)-1,1'-binaphthyl (55.0 mg, 0.1 mmol) and DIH (759.8 mg, 2.0 mmol) were dissolved in methylene chloride (10 mL), then trifluoromethanesulfonic acid (0.354 mL, 4.0 mmol) was added dropwise to the resulting solution, and the whole system was stirred at 0° C. for 18 hours. After the stirring, a saturated aqueous solution of sodium hydrogen carbonate was slowly added dropwise to the reaction mixture to neutralize the mixture. Next, sodium sulfite was added to the neutralized mixture, and then an organic phase was extracted with methylene chloride. The extracted organic phase was washed with water and then dried over magnesium sulfate. Next, the solvent was removed using an evaporator to obtain a crude product. After that, the obtained crude product was filtered by gel filtration chromatography to obtain 1,3,4,6,7,9,10,12-octa(trifluoromethanesulfonyloxy)perylene as a perylene derivative (68.9 mg, yield=48%). In this example, the reaction time was increased as compared to that in Example 11. The amount of 5,5',6,6'-tetraiodo-2,2',8,8'-tetra(trifluoromethanesulfonyloxy)-1,1'-binaphthyl produced was trace.

1,3,4,6,7,9,10,12-octa(trifluoromethanesulfonyloxy)perylene thus obtained was identified by $^1$H-NMR spectroscopy, $^{13}$C-NMR spectroscopy, $^{19}$F-NMR spectroscopy, and ASAP-MS. The chemical shifts and mass-to-charge ratios (m/z) determined are as shown below.

$^1$H-NMR: δ (ppm)=7.83 (s, 4H).

$^{13}$C-NMR: δ (ppm)=116.90, 116.99, 117.98, 131.44, 143.70, 144.70.

$^{19}$F-NMR: δ (ppm)=−73.23, −72.23.

MS (ASAP): Calcd for $C_{29}H_4F_{24}O_{24}S_8$: m/z=1435.65, Found m/z=1435.6671.

Figure 42:
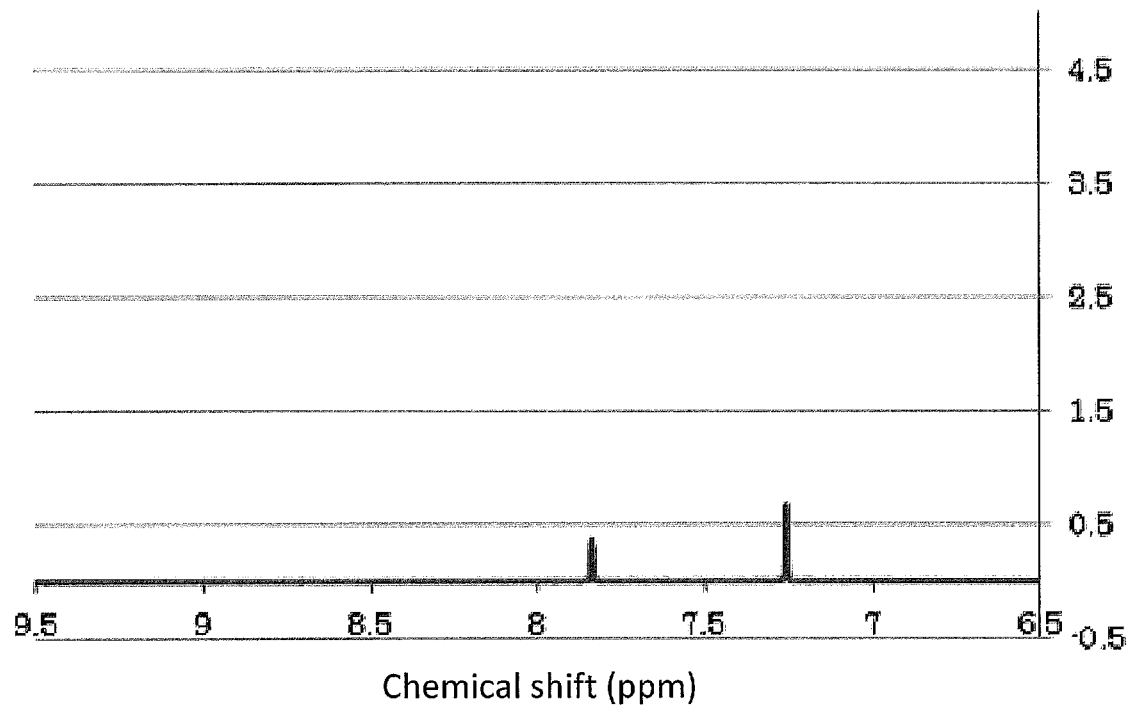
FIG. 42 shows a $^1$H-NMR profile of a perylene derivative produced in Example 15.
Figure 43:
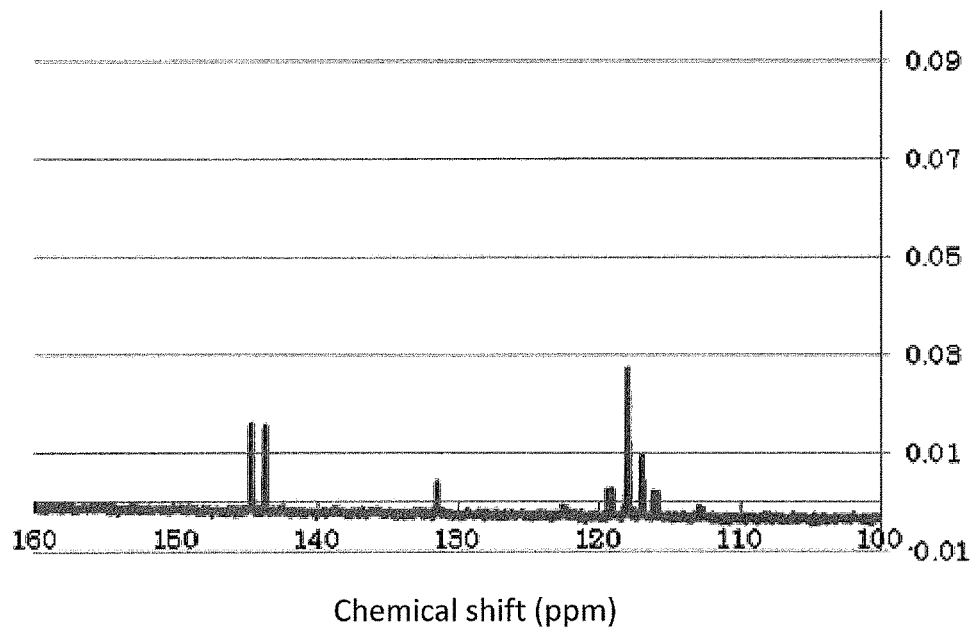
FIG. 43 shows a $^{13}$C-NMR profile of a perylene derivative produced in Example 15.
Figure 44:
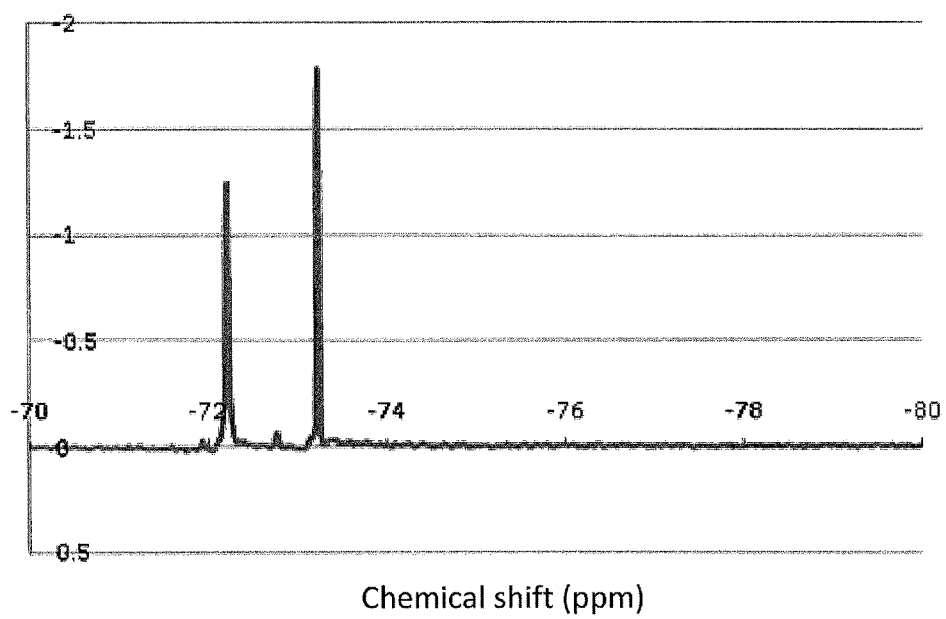
FIG. 44 shows a $^{19}$F-NMR profile of a perylene derivative produced in Example 15.

The $^1$H-NMR spectrum is shown in FIG. 42, the $^{13}$C-NMR spectrum is shown in FIG. 43, and the $^{19}$F-NMR spectrum is shown in FIG. 44.

Application Example 2

In Application Example 2, as shown in the following reaction formula, 8,8'-dihydroxy-2,2'-dimethoxy-4,4',6,6'-tetraiodo-1,1'-binaphthyl (racemate) was synthesized by hydrolysis from (S)-8,8'-bis(trifluoromethanesulfonyloxy)-2,2'-dimethoxy-4,4',6,6'-tetraiodo-1,1'-binaphthyl as produced in Example 1.

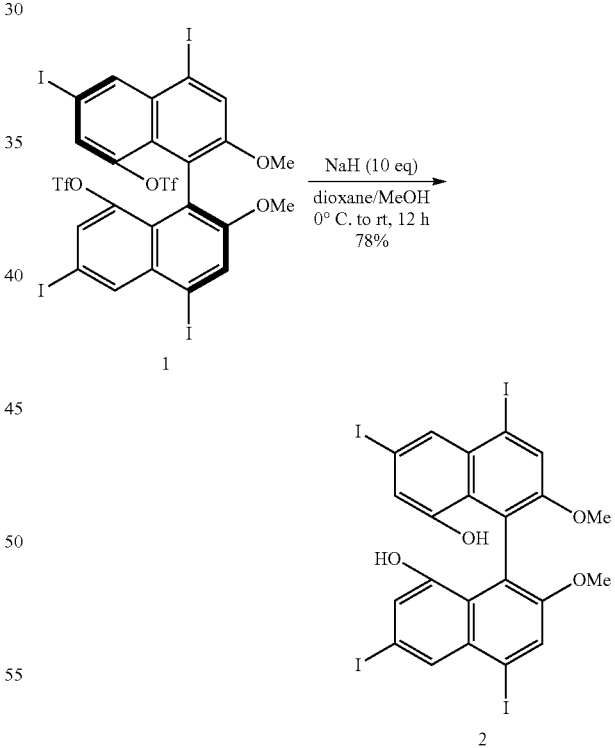

A dried Schlenk tube having an internal volume of 50 mL was charged with sodium hydride in an amount of 10 equivalents (24.0 mg, 1.0 mmol) relative to (S)-8,8'-bis(trifluoromethanesulfonyloxy)-2,2'-dimethoxy-4,4',6,6'-tetraiodo-1,1'-binaphthyl. Next, under nitrogen atmosphere, 2 mL of 1,4-dioxane was added as a solvent, and the contents of the tube were cooled to 0° C. To the solution in the tube was then added dropwise a solution of (S)-8,8'-bis(trifluoromethanesulfonyloxy)-2,2'-dimethoxy-4,4',6,6'-tetraiodo-1,1'-binaphthyl (111.4 mg, 0.10 mmol) in a liquid mixture of 2 mL of 1,4-dioxane and 2 mL of methanol, and the contents of the tube were stirred. After 12 hours from the start of the stirring, an aqueous solution of ammonium chloride was added to the reaction mixture in the tube to neutralize the mixture, and then an organic phase was extracted with ethyl acetate. The extracted organic phase was dried over magnesium sulfate. Next, the solvent was removed using an evaporator to obtain a crude product. After that, the obtained crude product was purified by silica gel column chromatography (hexane:ethyl acetate=10:1) to obtain 8,8'-dihydroxy-2,2'-dimethoxy-4,4',6,6'-tetraiodo-1,1'-binaphthyl (66.3 mg, 0.078 mmol) (Rf=0.25) in an isolation yield of 78%.

The compound obtained was identified by $^1$H-NMR spectroscopy, $^{13}$C-NMR spectroscopy, and ASAP-MS. The chemical shifts and mass-to-charge ratios (m/z) determined are as shown below.

$^1$H-NMR: δ (ppm)=8.12 (s, 2H), 7.93 (s, 2H), 7.09 (s, 2H), 5.57 (s, 2H), 3.70 (s, 6H).

$^{13}$C-NMR: δ (ppm)=155.348 (s), 154.013 (s), 132.932 (s), 132.341 (s), 126.706 (s), 124.628 (s), 124.189 (s), 117.915 (s), 95.852 (s), 88.854 (s), 56.580 (s).

MS (ASAP): Calcd for $C_{22}H_{14}I_4O_4$: m/z=849.71, Found m/z=849.7335.

Application Example 3

In Application Example 3, as shown in the following reaction formula, 8,8'-bis(t-butyldimethylsilyloxy)-2,2'-dimethoxy-4,4',6,6'-tetraiodo-1,1'-binaphthyl was synthesized from 8,8'-dihydroxy-2,2'-dimethoxy-4,4',6,6'-tetraiodo-1,1'-binaphthyl as produced in Application Example 2.

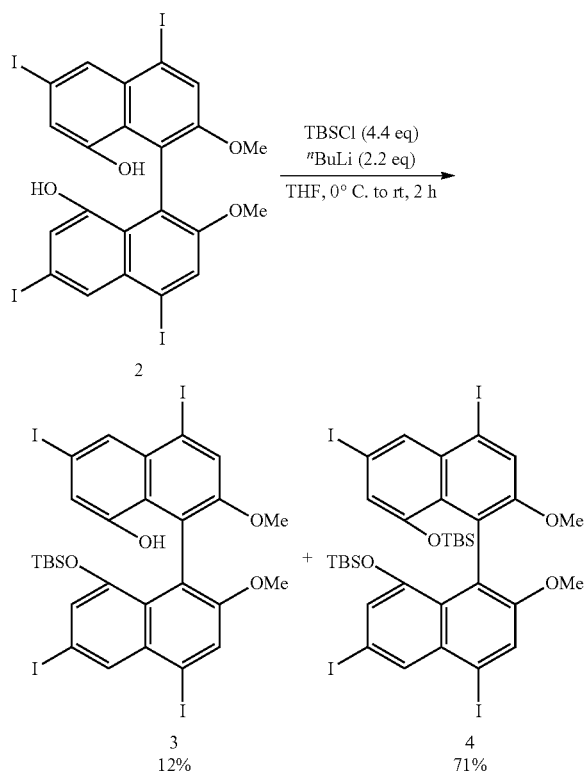

A dried Schlenk tube having an internal volume of 50 mL was charged with 8,8'-dihydroxy-2,2'-dimethoxy-4,4',6,6'-tetraiodo-1,1'-binaphthyl (170.0 mg, 0.2 mmol) and t-butyldimethylchlorosilane in an amount of 4.4 equivalents (132.6 mg, 0.88 mmol) relative to the binaphthyl derivative. Next, under nitrogen atmosphere, 10 mL of tetrahydrofuran was added as a solvent, and the contents of the tube were cooled to 0° C. To the solution in the tube was then added dropwise 2.2 equivalents of a n-butyl lithium/n-hexane solution (1.64 M, 0.27 mL, 0.44 mmol), and the contents of the tube were stirred. After 2 hours from the start of the stirring, an aqueous solution of ammonium chloride was added to the reaction mixture in the tube to neutralize the mixture, and then an organic phase was extracted with diethyl ether. The extracted organic phase was dried over magnesium sulfate. Next, the solvent was removed using an evaporator to obtain a crude product. After that, the obtained crude product was purified by silica gel column chromatography (hexane:ethyl acetate=10:1) to obtain 8-(t-butyldimethylsilyloxy)-8'-hydroxy-2,2'-dimethoxy-4,4',6,6'-tetraiodo-1,1'-binaphthyl (23.1 mg, 0.024 mmol) (Rf=0.4) in an isolation yield of 12% and 8,8'-bis(t-butyldimethylsilyloxy)-2,2'-dimethoxy-4,4',6,6'-tetraiodo-1,1'-binaphthyl (153.1 mg, 0.14 mmol) (Rf=0.5) in an isolation yield of 71%.

The compounds obtained were identified by $^1$H-NMR spectroscopy, $^{13}$C-NMR spectroscopy, and ASAP-MS. The chemical shifts and mass-to-charge ratios (m/z) determined are as shown below.

8,8'-(t-butyldimethylsilyloxy)-8'-hydroxy-2,2'-dimethoxy-4,4',6,6'-tetraiodo-1,1'-binaphthyl $^1$H-NMR: δ (ppm)=8.13 (s, 1H), 8.06 (s, 1H), 7.91 (s, 1H), 7.82 (s, 1H), 7.08 (s, 1H), 7.05 (s, 1H), 5.85 (s, 1H), 3.64 (s, 3H), 3.60 (s, 3H), 0.66 (s, 9H), −0.35 (s, 3H), −0.55 (s, 1H).

8,8'-bis(t-butyldimethylsilyloxy)-2,2'-dimethoxy-4,4',6,6'-tetraiodo-1,1'-binaphthyl $^1$H-NMR: δ (ppm)=8.07 (s, 2H), 7.79 (s, 2H), 6.96 (s, 2H), 3.54 (s, 6H), 0.68 (s, 18H), −0.25 (s, 6H), −0.71 (s, 6H).

$^{13}$C-NMR: δ (ppm)=153.337 (s), 153.222 (s), 134.124 (s), 133.295 (s), 126.735 (s), 126.506 (s), 123.827 (s), 122.101 (s), 96.577 (s), 88.683 (s), 56.808 (s), 19.395 (s), −4.289 (s), −4.728 (s).

MS (ASAP): Calcd for $C_{34}H_{42}I_4O_4Si_2$: m/z=1077.88, Found m/z=1078.9579.

Application Example 4

In Application Example 4, as shown in the following reaction formula, 8,8'-bis(t-butyldimethylsilyloxy)-2,2'-dimethoxy-4,4',6,6'-tetramethyl-1,1'-binaphthyl was synthesized from 8,8'-bis(t-butyldimethylsilyloxy)-2,2'-dimethoxy-4,4',6,6'-tetraiodo-1,1'-binaphthyl as produced in Application Example 3.

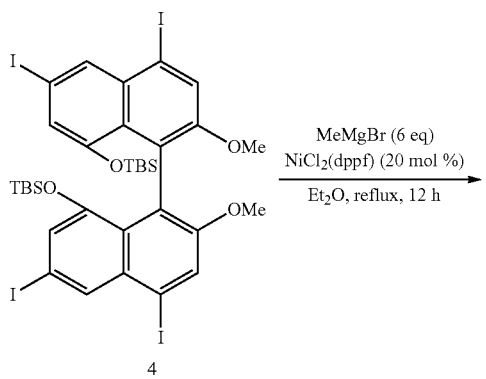

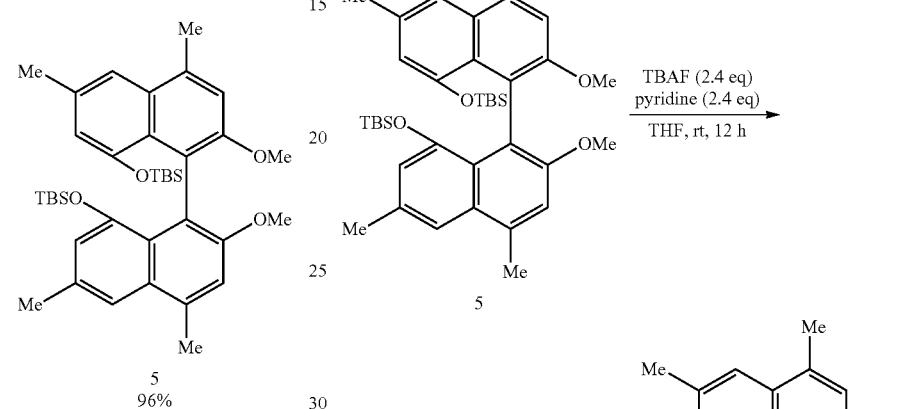

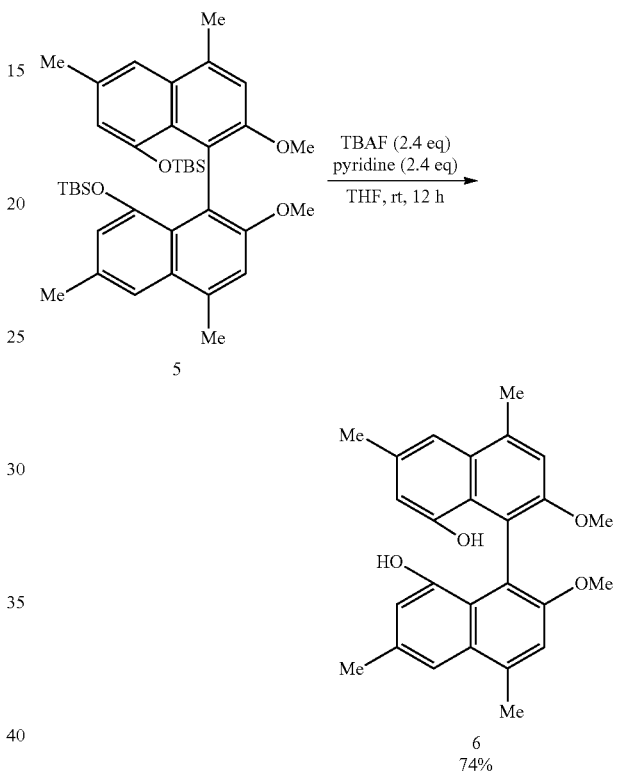

A dried two-necked recovery flask having an internal volume of 50 mL was charged with 8,8'-bis(t-butyldimethylsilyloxy)-2,2'-dimethoxy-4,4',6,6'-tetraiodo-1,1'-binaphthyl (111.4 mg, 0.10 mmol) and 20 mol % [1,1'-bis(diphenylphosphino)ferrocene]nickel(II) dichloride (13.68 mg, 0.02 mmol). Next, under nitrogen atmosphere, 10 mL of diethyl ether was added as a solvent, and the contents of the flask were heated to 50° C., after which a 3.00 M methylmagnesium bromide/tetrahydrofuran solution was added dropwise in an amount of 6 equivalents (0.20 mL, 0.60 mmol) relative to the binaphthyl derivative, and the contents of the flaks were further stirred. After 12 hours from the start of the stirring, an aqueous solution of ammonium chloride was added to the reaction mixture in the flask to neutralize the mixture, and then an organic phase was extracted with diethyl ether. The extracted organic phase was dried over magnesium sulfate. Next, the solvent was removed using an evaporator to obtain a crude product. After that, the obtained crude product was purified by silica gel column chromatography (hexane:ethyl acetate=10:1) to obtain 8,8'-bis(t-butyldimethylsilyloxy)-2,2'-dimethoxy-4,4',6,6'-tetramethyl-1,1'-binaphthyl (60.5 mg, 0.096 mmol) (Rf=0.4) in an isolation yield of 96%.

The compound obtained was identified by $^1$H-NMR spectroscopy, $^{13}$C-NMR spectroscopy, and ASAP-MS. The chemical shifts and mass-to-charge ratios (m/z) determined are as shown below.

$^1$H-NMR: δ (ppm)=7.28 (s, 2H), 7.06 (s, 2H), 6.51 (s, 2H), 3.45 (s, 6H), 2.68 (s, 6H), 2.39 (s, 6H), 0.65 (s, 18H), −0.34 (s, 6H), −0.71 (s, 6H).

$^{13}$C-NMR: δ (ppm)=153.365 (s), 152.259 (s), 132.608 (s), 131.798 (s), 131.197 (s), 126.897 (s), 122.311 (s), 116.743 (s), 116.028 (s), 115.065 (s), 57.266 (s), 21.931 (s), 20.815 (s), 19.318 (s), −4.118 (s), −4.642 (s).

MS (ASAP): Calcd for $C_{38}H_{54}O_4Si_2$: m/z=630.36, Found m/z=631.4206.

Application Example 5

In Application Example 5, as shown in the following reaction formula, 8,8'-dihydroxy-2,2'-dimethoxy-4,4',6,6'-tetramethyl-1,1'-binaphthyl was synthesized from 8,8'-bis(t-butyldimethylsilyloxy)-2,2'-dimethoxy-4,4',6,6'-tetramethyl-1,1'-binaphthyl as produced in Application Example 4.

A dried Schlenk tube having an internal volume of 20 mL was charged with 8,8'-bis(t-butyldimethylsilyloxy)-2,2'-dimethoxy-4,4',6,6'-tetramethyl-1,1'-binaphthyl (111.4 mg, 0.1 mmol) and tetra-n-butylammonium fluoride in an amount of 2.4 equivalents (13.68 mg, 0.02 mmol) relative to the binaphthyl derivative. Next, under nitrogen atmosphere, 10 mL of tetrahydrofuran was added as a solvent, and 2.4 equivalents of pyridine (0.20 mL, 0.60 mmol) was further added dropwise, after which the contents of the tube were stirred at room temperature. After 12 hours from the start of the stirring, an aqueous solution of ammonium chloride was added to the reaction mixture in the tube, and then an organic phase was extracted with diethyl ether. The extracted organic phase was dried over magnesium sulfate. Next, the solvent was removed using an evaporator to obtain a crude product. After that, the obtained crude product was purified by silica gel column chromatography (hexane:ethyl acetate=5:1) to obtain 8,8'-dihydroxy-2,2'-dimethoxy-4,4',6,6'-tetramethyl-1,1'-binaphthyl (29.8 mg, 0.074 mmol) (Rf=0.2) in an isolation yield of 74%.

The compound obtained was identified by $^1$H-NMR spectroscopy, $^{13}$C-NMR spectroscopy, and ASAP-MS. The chemical shifts and mass-to-charge ratios (m/z) determined are as shown below.

¹H-NMR: δ (ppm)=7.35 (s, 2H), 7.20 (s, 2H), 6.69 (s, 2H), 6.10 (s, 2H), 3.72 (s, 6H), 2.75 (s, 6H), 2.43 (s, 6H).

¹³C-NMR: δ (ppm)=154.042 (s), 153.479 (s), 138.290 (s), 134.916 (s), 130.682 (s), 121.405 (s), 116.457 (s), 115.179 (s), 114.483 (s), 112.261 (s), 57.066 (s), 21.797 (s), 21.178 (s) MS (ASAP): Calcd for $C_{26}H_{26}O_4$: 111/Z=402.18, Found m/z=403.1710.

Application Example 6

In Application Example 6, as shown in the following reaction formula, 8,8'-bis{(1S,4R)-[3-oxo-4,7,7-trimethyl-2-oxabicyclo[2.2.1]heptane]-1-carbonyl}oxy-(aR)-2,2'-dimethoxy-4,4',6,6'-tetramethyl-1,1'-binaphthyl and 8,8'-bis{(1S,4R)-[3-oxo-4,7,7-trimethyl-2-oxabicyclo[2.2.1]heptane]-1-carbonyl}oxy-(aS)-2,2'-dimethoxy-4,4',6,6'-tetramethyl-1,1'-binaphthyl were synthesized from 8,8'-dihydroxy-2,2'-dimethoxy-4,4',6,6'-tetramethyl-1,1'-binaphthyl as produced in Application Example 5.

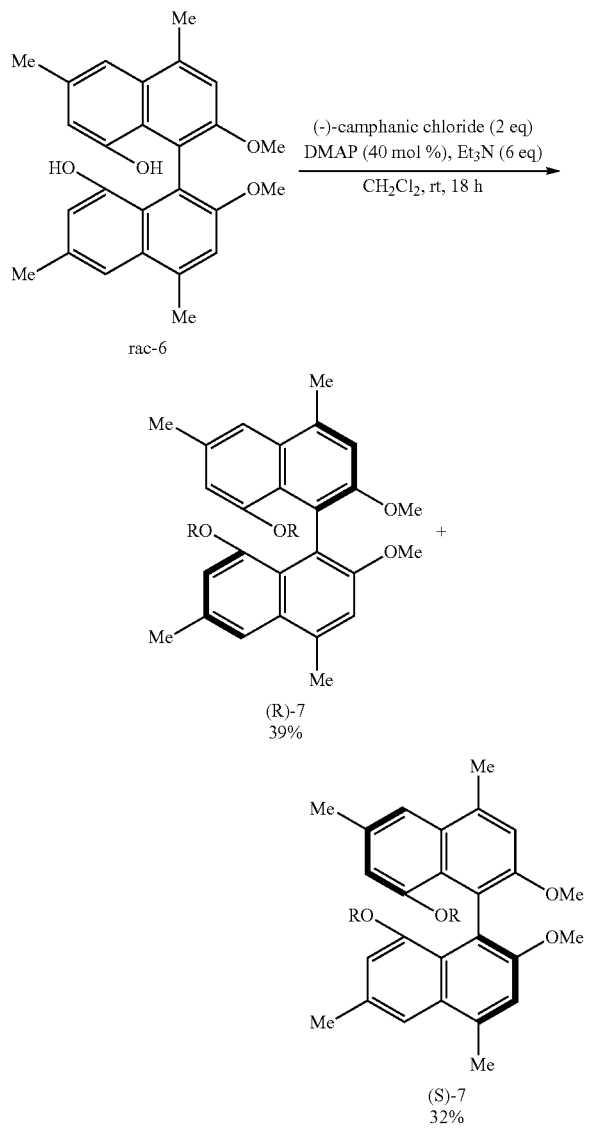

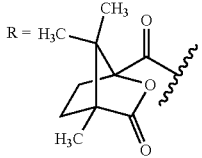

A dried Schlenk tube having an internal volume of 20 mL was charged with 8,8'-dihydroxy-2,2'-dimethoxy-4,4',6,6'-tetramethyl-1,1'-binaphthyl (40.2 mg, 0.10 mmol), (−)-camphanic chloride in an amount of 2 equivalents (43.33 mg, 0.20 mmol) relative to the binaphthyl derivative, and 40 mol % N,N-dimethyl-4-aminopyridine (9.77 mg, 0.080 mmol). Next, under nitrogen atmosphere, 5 mL of methylene chloride and 6 equivalents of triethylamine (0.084 mL, 0.60 mmol) were added as solvents, and the contents of the tube were stirred at room temperature. After 18 hours from the start of the stirring, an aqueous solution of ammonium chloride was added to the reaction mixture in the tube to neutralize the mixture, and then an organic phase was extracted with diethyl ether. The extracted organic phase was dried over sodium sulfate. Next, the solvents were removed using an evaporator to obtain a crude product. After that, the obtained crude product was purified by silica gel column chromatography (hexane:methylene chloride:toluene:diethyl ether=3:2:2:1) to obtain 8,8'-bis{(1S,4R)-[3-oxo-4,7,7-trimethyl-2-oxabicyclo[2.2.1]heptane]-1-carbonyl}oxy-(aR)-2,2'-dimethoxy-4,4',6,6'-tetramethyl-1,1'-binaphthyl (29.7 mg, 0.039 mmol) (Rf=0.3) in an isolation yield of 39% and 8,8'-bis{(1S,4R)-[3-oxo-4,7,7-trimethyl-2-oxabicyclo[2.2.1]heptane]-1-carbonyl}oxy-(aS)-2,2'-dimethoxy-4,4',6,6'-tetramethyl-1,1'-binaphthyl (25.9 mg, 0.032 mmol) (Rf=0.2) in an isolation yield of 32%.

The compounds obtained were identified by ¹H-NMR spectroscopy and ¹³C-NMR spectroscopy. The chemical shifts and mass-to-charge ratios (m/z) determined are as shown below.

8,8'-bis{(1S,4R)-[3-oxo-4,7,7-trimethyl-2-oxabicyclo[2.2.1]heptane]-1-carbonyl}oxy-(aR)-2,2'-dimethoxy-4,4',6,6'-tetramethyl-1,1'-binaphthyl ¹H-NMR: δ (ppm)=7.64 (s, 2H), 7.15 (s, 2H), 6.76 (s, 2H), 3.54 (s, 6H), 2.72 (s, 6H), 2.50 (s, 6H), 1.59 (t, 2H), 1.45 (t, 2H), 1.33 (t, 2H), 1.01 (t, 2H), 0.94 (s, 6H), 0.84 (s, 6H), 0.70 (s, 6H).

¹³C-NMR: δ (ppm)=177.859 (s), 166.628 (s), 153.775 (s), 147.196 (s), 134.792 (s), 132.599 (s), 130.997 (s), 126.087 (s), 122.330 (s), 122.158 (s), 117.019 (s), 116.047 (s), 90.113 (s), 56.961 (s), 54.520 (s), 54.244 (s), 29.463 (s), 28.691 (s), 21.597 (5), 20.815 (s), 16.630 (s), 16.515 (s), 9.688 (s).

8,8'-bis{(1S,4R)-[3-oxo-4,7,7-trimethyl-2-oxabicyclo[2.2.1]heptane]-1-carbonyl}oxy-(aS)-2,2'-dimethoxy-4,4',6,6'-tetramethyl-1,1'-binaphthyl ¹H-NMR: δ (ppm)=7.66 (s, 2H), 7.25 (s, 2H), 6.71 (s, 2H), 3.62 (s, 6H), 2.72 (s, 6H), 2.48 (s, 6H), 1.49 (t, 2H), 1.27 (t, 2H), 1.18 (t, 2H), 1.14 (t, 2H), 0.97 (s, 6H), 0.95 (s, 6H), 0.81 (s, 6H).

¹³C-NMR: δ (ppm)=178.260 (s), 166.246 (s, 6H), 154.481 (s), 146.729 (s), 135.068 (s), 131.674 (s), 130.720 (s), 125.391 (s), 122.387 (s), 121.405 (s), 116.714 (s), 115.999 (s), 90.418 (s), 56.599 (s), 54.787 (s), 54.654 (s), 28.910 (s), 28.062 (s), 21.588 (s), 20.777 (s), 17.078 (s), 16.591 (s), 9.727 (s).

The present disclosure includes the features specified in the following items.

1. A method for producing polycyclic aromatic compounds, including the step of mixing a 1,1'-binaphthyl precursor derivative having a 1,1'-binaphthyl skeleton, an organic acid, and an iodinating or brominating agent to introduce a bond with an atom other than a hydrogen atom at the 8-position and/or 8'-position of the skeleton, the 1,1'-binaphthyl precursor derivative having an electron-donating group at the 2-position of the skeleton and at the 2'-position of the skeleton, the electron-donating group containing an oxygen atom directly bonded to the skeleton, wherein a polycyclic aromatic compound having a polycyclic aromatic structure derived from the 1,1'-binaphthyl precursor derivative is produced.

2. The production method according to Item 1, wherein the atom other than a hydrogen atom at the 8-position of the skeleton and the atom other than a hydrogen atom at the 8'-position of the skeleton are each independently a carbon atom or an oxygen atom.

3. The production method according to Item 1 or 2, wherein a substituent (substituent $Z^1$) is introduced as the bond at the 8-position and/or 8'-position of the skeleton.

4. The production method according to any one of Items 1 to 3, wherein a substituent (substituent $Z^1$) is introduced as the bond at the 8-position and/or 8'-position of the skeleton, and a 1,1'-binaphthyl derivative having the substituent introduced at the 8-position and/or 8'-position of the skeleton is obtained as the polycyclic aromatic compound.

5. The production method according to Item 3 or 4, wherein the substituent (substituent $Z^1$) is at least one selected from an organic acid group, a hydroxy group, an iodo group, and a bromo group.

6. The production method according to Item 1 or 2, wherein, as the bond, a bond connecting the 8-position and 8'-position of the skeleton is introduced.

7. The production method according to Item 1, 2, or 6, wherein, as the bond, a bond connecting the 8-position and 8'-position of the skeleton is introduced, and perylene or a perylene derivative is obtained as the polycyclic aromatic compound.

8. The production method according to any one of Items 1 to 7, wherein the polycyclic aromatic compound is a 1,1'-binaphthyl derivative, perylene, or a perylene derivative.

9. The production method according to any one of Items 1 to 8, wherein the precursor derivative, the organic acid, and the iodinating agent are mixed.

10. The production method according to any one of Items 1 to 9, wherein the electron-donating group is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

11. The production method according to Item 10, wherein the R is a hydrogen atom, a methyl group, or a trifluoromethanesulfonyl group.

12. The production method according to any one of Items 1 to 11, wherein the iodinating agent is at least one selected from 1,3-diiodo-5,5-dimethylhydantoin and N-iodosuccinimide.

13. The production method according to any one of Items 1 to 12, wherein the organic acid is at least one selected from trifluoromethanesulfonic acid, methanesulfonic acid, trifluoroacetic acid, and p-toluenesulfonic acid.

14. The production method according to any one of Items 1 to 5 and 8 to 13, wherein the 1,1'-binaphthyl derivative further having the substituent (substituent $Z^4$) introduced at at least one position selected from the 4-position, 4'-position, 5-position, 5'-position, 6-position, and 6'-position of the skeleton is obtained as the polycyclic aromatic compound.

15. The production method according to any one of Items 1, 2, and 6 to 13, wherein a perylene derivative is obtained as the polycyclic aromatic compound, the perylene derivative having the substituent (substituent $Z^4$) introduced at at least one position selected from the 3-position, 4-position, 5-position, 8-position, 9-position, and 10-position of a skeleton (perylene skeleton) of the derivative.

16. A method for producing 1,1'-binaphthyl derivatives, including mixing a 1,1'-binaphthyl precursor derivative, an organic acid, and an iodinating or brominating agent to obtain a 1,1'-binaphthyl derivative, the 1,1'-binaphthyl precursor derivative having a 1,1'-binaphthyl skeleton and having an electron-donating group at the 2-position of the skeleton and at the 2'-position of the skeleton, the electron-donating group containing an oxygen atom directly bonded to the skeleton, the 1,1'-binaphthyl derivative having a substituent (substituent $Z^1$) introduced at the 8-position and/or 8'-position of the skeleton.

17. The production method according to Item 16, wherein the precursor derivative, the organic acid, and the iodinating agent are mixed.

18. The production method according to Item 16 or 17, wherein the electron-donating group is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

19. The production method according to Item 18, wherein the R is a hydrogen atom, a methyl group, or a trifluoromethanesulfonyl group.

20. The production method according to any one of Items 16 to 19, wherein the iodinating agent is at least one selected from 1,3-diiodo-5,5-dimethylhydantoin and N-iodosuccinimide.

21. The production method according to any one of Items 16 to 20, wherein the organic acid is at least one selected from trifluoromethanesulfonic acid, methanesulfonic acid, trifluoroacetic acid, and p-toluenesulfonic acid.

22. The production method according to any one of Items 16 to 21, wherein the substituent (substituent $Z^1$) is at least one selected from an organic acid group, a hydroxy group, and an iodo or bromo group.

23. The production method according to any one of Items 16 to 22, wherein the binaphthyl derivative obtained further has the substituent (substituent $Z^4$) introduced at at least one position selected from the 4-position, 4'-position, 5-position, 5'-position, 6-position, and 6'-position of the skeleton.

24. A method for producing perylene derivatives, including mixing a 1,1'-binaphthyl precursor derivative, an organic acid, and an iodinating or brominating agent to obtain a perylene derivative, the 1,1'-binaphthyl precursor derivative having a 1,1'-binaphthyl skeleton and having an electron-donating group at the 2-position of the skeleton and at the 2'-position of the skeleton, the electron-donating group containing an oxygen atom directly bonded to the skeleton.

25. The production method according to Item 24, wherein the precursor derivative, the organic acid, and the iodinating agent are mixed.

26. The production method according to Item 24 or 25, wherein the electron-donating group is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

27. The production method according to Item 26, wherein the R is a hydrogen atom, a methyl group, or a trifluoromethanesulfonyl group.

28. The production method according to any one of Items 24 to 27, wherein the iodinating agent is at least one selected from 1,3-diiodo-5,5-dimethylhydantoin and N-iodosuccinimide.

29. The production method according to any one of Items 24 to 28, wherein the organic acid is at least one selected from trifluoromethanesulfonic acid, methanesulfonic acid, trifluoroacetic acid, and p-toluenesulfonic acid.

30. The production method according to any one of Items 24 to 29, wherein the perylene derivative obtained further has a substituent (substituent $Z^4$) introduced at at least one selected from the 3-position, 4-position, 5-position, 8-position, 9-position, and 10-position of the perylene skeleton.

31. A method for producing polycyclic aromatic compounds, including the step of mixing a naphthalene derivative, an organic acid, and an iodinating or brominating agent to allow a coupling reaction of the derivative to take place so as to form a 1,1'-binaphthyl skeleton having a substituent (substituent $Z^2$, $Z^5$, or $Z^6$) at the 2-position and 2'-position thereof, the naphthalene derivative having a naphthalene skeleton and having a substituent (substituent $Z^5$) at the 2-position of the naphthalene skeleton, wherein a polycyclic aromatic compound having a polycyclic aromatic structure derived from the 1,1'-binaphthyl skeleton is produced.

32. The production method according to Item 31, wherein a 1,1'-binaphthyl derivative having the substituent (substituent $Z^2$, $Z^5$, or $Z^6$) at the 2-position of the binaphthyl skeleton and at the 2'-position of the binaphthyl skeleton is obtained as the polycyclic aromatic compound.

33. The production method according to Item 31 or 32, wherein the substituent (substituent $Z^2$, $Z^5$, or $Z^6$) is an electron-donating group containing an oxygen atom directly bonded to the binaphthyl skeleton, and the method further includes the step of introducing a bond with an atom other than a hydrogen atom at the 8-position and/or 8'-position of the 1,1'-binaphthyl skeleton.

34. The production method according to any one of Items 31 to 33, wherein, as the bond, a bond connecting the 8-position and 8'-position of the binaphthyl skeleton is introduced.

35. The production method according to any one of Items 31 to 34, wherein, as the bond, a bond connecting the 8-position and 8'-position of the binaphthyl skeleton is introduced, and perylene or a perylene derivative is obtained as the polycyclic aromatic compound.

36. The production method according to any one of Items 31 to 35, wherein the polycyclic aromatic compound is a 1,1'-binaphthyl derivative, perylene, or a perylene derivative.

37. The production method according to any one of Items 31 to 36, wherein the naphthalene derivative, the organic acid, and the iodinating agent are mixed.

38. The production method according to any one of Items 31 to 37, wherein the iodinating agent is at least one selected from 1,3-diiodo-5,5-dimethylhydantoin and N-iodosuccinimide.

39. The production method according to any one of Items 31 to 38, wherein the organic acid is at least one selected from trifluoromethanesulfonic acid, methanesulfonic acid, trifluoroacetic acid, and p-toluenesulfonic acid.

40. The production method according to any one of Items 31 to 39, wherein the substituent (substituent $Z^2$, $Z^5$, or $Z^6$) is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

41. The production method according to Item 40, wherein the R is a hydrogen atom, a methyl group, or a trifluoromethanesulfonyl group.

42. The production method according to any one of Items 31 to 41, wherein a perylene derivative having a perylene skeleton and having the substituent (substituent $Z^4$) introduced at at least one position selected from the 3-position, 4-position, 5-position, 8-position, 9-position, and 10-position of the perylene skeleton is obtained as the polycyclic aromatic compound.

43. A method for producing 1,1'-binaphthyl derivatives, including mixing a naphthalene derivative, an organic acid, and an iodinating or brominating agent to allow a coupling reaction of the naphthalene derivative to take place so as to obtain a 1,1'-binaphthyl derivative, the naphthalene derivative having a naphthalene skeleton and having a substituent at the 2-position of the naphthalene skeleton, the 1,1'-binaphthyl derivative having a 1,1'-binaphthyl skeleton and having a substituent (substituent $Z^2$, $Z^5$, or $Z^6$) at the 2-position of the 1,1'-binaphthyl skeleton and at the 2'-position of the 1,1'-binaphthyl skeleton.

44. The production method according to Item 43, wherein the substituent (substituent $Z^2$, $Z^5$, or $Z^6$) is an electron-donating group containing an oxygen atom directly bonded to the binaphthyl skeleton.

45. The production method according to Item 43 or 44, wherein the substituent (substituent $Z^2$, $Z^5$, or $Z^6$) is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

46. The production method according to Item 45, wherein the R is a hydrogen atom, a methyl group, or a trifluoromethanesulfonyl group.

47. The production method according to any one of Items 43 to 46, wherein the binaphthyl derivative obtained further has a substituent (substituent $Z^1$) introduced at the 8-position and/or 8'-position of the binaphthyl skeleton.

48. A method for producing 1,1'-binaphthyl derivatives, including allowing a 1,1'-binaphthyl derivative represented by formula (1) below to undergo a reaction involving at least one group selected from $Y^1$, $Y^2$, —$OR^1$, —$OR^2$, and at least one X so as to obtain a 1,1'-binaphthyl derivative that is a result of the reaction and different from the derivative represented by the formula (1).

In the formula (1), X is an iodo group or a bromo group, $R^1$ and $R^2$ are each independently a hydrogen atom, an alkyl group having 1 to 50 carbon atoms, an allyl group, a benzyl group, a trifluoromethanesulfonyl group, a silyl group, or a protecting group for a hydroxy group, and $Y^1$ and $Y^2$ are each independently a hydroxy group or an organic acid group containing an oxygen atom directly bonded to the binaphthyl skeleton of the derivative.

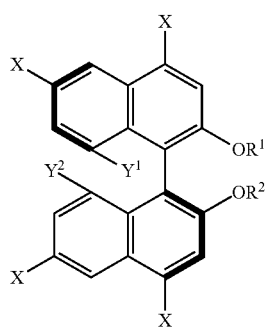

(1)

49. The production method according to Item 48, wherein the X is an iodo group, the $R^1$ and $R^2$ are hydrogen atoms, methyl groups, or trifluoromethanesulfonyl groups, and the $Y^1$ and $Y^2$ are each independently the organic acid group or a hydroxy group.

50. The production method according to Item 48 or 49, wherein the reaction is at least one reaction selected from a substituent reaction and a hydrolysis reaction.

51. A method for producing naphthalene derivatives, including mixing a 1,1'-binaphthyl derivative and an organic acid to allow a decoupling (cleavage) reaction of the 1,1'-binaphthyl derivative to take place so as to obtain a naphthalene derivative, the 1,1'-binaphthyl derivative having a 1,1'-binaphthyl skeleton and having a substituent (substituent $Z^2$, $Z^5$, or $Z^6$) at the 2-position and/or 2'-position of the 1,1'-binaphthyl skeleton, the naphthalene derivative having a naphthalene skeleton having a substituent (substituent $Z^2$, $Z^5$, or $Z^6$).

52. A 1,1'-binaphthyl derivative having a binaphthyl skeleton and having a substituent (substituent $Z^1$) at the 8-position and/or 8'-position of the binaphthyl skeleton.

53. The 1,1'-binaphthyl derivative according to Item 52, wherein the substituent (substituent $Z^1$) is a group containing an oxygen atom directly bonded to the skeleton, an aliphatic group having 1 to 50 carbon atoms, or an aryl group having 6 to 30 carbon atoms.

54. The 1,1'-binaphthyl derivative according to Item 52, wherein the substituent (substituent $Z^1$) is a group $P^1$ containing an oxygen atom directly bonded to the skeleton, groups $P^2$ each containing an oxygen atom directly bonded to the skeleton are present at three or more positions of the skeleton other than the position at which the group $P^1$ is present, and $P^1$ and $P^2$ may be the same or different.

The present invention may be embodied in other forms without departing from the spirit or essential characteristics thereof. The embodiments disclosed in this specification are to be considered in all respects as illustrative and not limiting. The scope of the present invention is indicated by the appended claims rather than by the foregoing description, and all changes which come within the meaning and range of equivalency of the claims are intended to be embraced therein.

INDUSTRIAL APPLICABILITY 1,1'-binaphthyl derivatives obtained by the production methods of the present disclosure and 1,1'-binaphthyl derivatives of the present disclosure can themselves be used in various applications, and compounds formed through further derivation from the derivatives can also be used in various applications.

Perylene derivatives and perylene obtained by the production methods of the present disclosure and perylene derivatives of the present disclosure can themselves be used in various applications, and compounds formed through further derivation from the derivatives can also be used in various applications.

Naphthalene derivatives obtained by the production methods of the present disclosure and naphthalene derivatives of the present disclosure can themselves be used in various applications, and compounds formed through further derivation from the derivatives can also be used in various applications.

The invention claimed is:

1. A method for producing 1,1'-binaphthyl derivatives, comprising mixing a 1,1'-binaphthyl precursor derivative, an organic acid, and an iodinating or brominating agent to obtain a 1,1'-binaphthyl derivative, the 1,1'-binaphthyl precursor derivative having a 1,1'-binaphthyl skeleton and having an electron-donating group at 2-position of the skeleton and at 2'-position of the skeleton, the electron-donating group containing an oxygen atom directly bonded to the skeleton, the 1,1'-binaphthyl derivative having a substituent introduced at 8-position and/or 8'-position of the skeleton.

2. The method for producing 1,1'-binaphthyl derivatives according to claim 1, wherein the precursor derivative, the organic acid, and the iodinating agent are mixed.

3. The method for producing 1,1'-binaphthyl derivatives according to claim 1, wherein the electron-donating group is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

4. The method for producing 1,1'-binaphthyl derivatives according to claim 3, wherein the R is a hydrogen atom, a methyl group, or a trifluoromethanesulfonyl group.

5. The method for producing 1,1'-binaphthyl derivatives according to claim 1, wherein the iodinating agent is at least one selected from 1,3-diiodo-5,5-dimethylhydantoin and N-iodosuccinimide.

6. The method for producing 1,1'-binaphthyl derivatives according to claim 1, wherein the organic acid is at least one selected from trifluoromethanesulfonic acid, methanesulfonic acid, trifluoroacetic acid, and p-toluenesulfonic acid.

7. The method for producing 1,1'-binaphthyl derivatives according to claim 1, wherein the substituent is at least one selected from an organic acid group, a hydroxy group, and an iodo or bromo group.

8. The method for producing 1,1'-binaphthyl derivatives according to claim 1, wherein the binaphthyl derivative further has the substituent introduced at at least one position selected from 4-position, 4'-position, 5-position, 5'-position, 6-position, and 6'-position of the skeleton.

9. A method for producing 1,1'-binaphthyl derivatives, comprising mixing a naphthalene derivative, an organic acid, and an iodinating or brominating agent to allow a coupling reaction of the naphthalene derivative to take place so as to obtain a 1,1'-binaphthyl derivative, the naphthalene derivative having a naphthalene skeleton and having a substituent at 2-position of the naphthalene skeleton, the 1,1'-binaphthyl derivative having a 1,1'-binaphthyl skeleton and having a substituent at 2-position of the 1,1'-binaphthyl skeleton and at 2'-position of the 1,1'-binaphthyl skeleton.

10. The method for producing 1,1'-binaphthyl derivatives according to claim 9, wherein the substituent is an electron-donating group containing an oxygen atom directly bonded to the skeleton.

11. The method for producing 1,1'-binaphthyl derivatives according to claim 9, wherein the substituent is —OR wherein R is a hydrogen atom, an alkyl group having 1 to 50 carbon atoms, an allyl group, a benzyl group, a trifluoromethanesulfonyl group, a silyl group, or a protecting group for a hydroxy group.

12. The method for producing 1,1'-binaphthyl derivatives according to claim 11, wherein the R is a hydrogen atom, a methyl group, or a trifluoromethanesulfonyl group.

13. The method for producing 1,1'-binaphthyl derivatives according to claim 9, wherein the binaphthyl derivative further has a substituent introduced at 8-position and/or 8'-position of the binaphthyl skeleton.

14. A method for producing 1,1'-binaphthyl derivatives, comprising allowing a 1,1'-binaphthyl derivative represented by the following formula (1) to undergo a reaction involving at least one group selected from $Y^1$, $Y^2$, —$OR^1$, —$OR^2$, and at least one X so as to obtain a 1,1'-binaphthyl derivative that is a result of the reaction and different from the derivative represented by the formula (1):

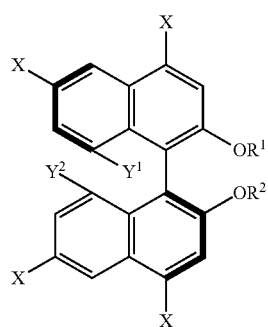

(1)

wherein X is an iodo group or a bromo group, $R^1$ and $R^2$ are each independently a hydrogen atom, an alkyl group having 1 to 50 carbon atoms, an allyl group, a benzyl group, a trifluoromethanesulfonyl group, a silyl group, or a protecting group for a hydroxy group, and $Y^1$ and $Y^2$ are each independently a hydroxy group or an organic acid group containing an oxygen atom directly bonded to the binaphthyl skeleton of the derivative.

15. The method for producing 1,1'-binaphthyl derivatives according to claim 14, wherein the X is an iodo group, the $R^1$ and $R^2$ are hydrogen atoms, methyl groups, or trifluoromethanesulfonyl groups, and the $Y^1$ and $Y^2$ are each independently the organic acid group or a hydroxy group.

16. The method for producing 1,1'-binaphthyl derivatives according to claim 14, wherein the reaction is at least one reaction selected from a substituent reaction and a hydrolysis reaction.

17. A 1,1'-binaphthyl derivative having a binaphthyl skeleton and having one or more first substituents at an 8-position and/or an 8'-position, and one or more second substituents at a 2-position and/or a 2'-position of the binaphthyl skeleton, wherein the one or more second substituents are each an electron-donating group containing an oxygen atom directly bonded to the skeleton, an organic acid group, or a ketone group.

18. The 1,1'-binaphthyl derivative according to claim 17, wherein the one or more first substituents are each independently a group containing an oxygen atom directly bonded to the skeleton, an aliphatic group having 1 to 50 carbon atoms, or an aryl group having 6 to 30 carbon atoms.

19. The 1,1'-binaphthyl derivative according to claim 17, wherein the one or more first substituents are each a group $P^1$ containing an oxygen atom directly bonded to the skeleton, groups $P^2$ each containing an oxygen atom directly bonded to the skeleton are present at three or more positions of the skeleton other than the position at which the group $P^1$ is present, and $P^1$ and $P^2$ are the same or different.

20. The 1,1'-binaphthyl derivative according to claim 17, wherein the electron-donating group is —OR wherein R is a hydrogen atom, an alkyl group having 1 to 50 carbon atoms, an allyl group, a benzyl group, a silyl group, or a protecting group for a hydroxy group.

21. The 1,1'-binaphthyl derivative according to claim 17, wherein the organic acid group is at least one selected from a trifluoromethanesulfonic acid group, a methanesulfonic acid group, a trifluoroacetic acid group, and a p-toluenesulfonic acid group.

22. The 1,1'-binaphthyl derivative according to claim 17, wherein the one or more second substituents are each the electron-donating group, and the one or more first substituents are each independently an organic acid group, a hydroxy group, a ketone group, a group having an ether structure, an aliphatic group having 1 to 50 carbon atoms, an aryl group having 6 to 30 carbon atoms, an alkoxy group, an aralkyl group, a thioalkoxy group, a silyl group, a group containing a phosphorus atom directly bonded to the skeleton, an amino group, an iodo group, a bromo group or a chloro group.

23. The 1,1'-binaphthyl derivative according to claim 17, wherein the one or more second substituents are each the organic acid group.

24. The 1,1'-binaphthyl derivative according to claim 17, wherein the derivative has an organic acid group and/or a hydroxy group as a substituent at all the positions other than the 1-position and 1'-position of the skeleton.

25. The 1,1'-binaphthyl derivative according to claim 17, wherein the derivative has an organic acid group and/or a hydroxy group as a substituent at all the positions other than the 1-position, 1'-position, 3-position and 3'-position of the skeleton.

26. A 1,1'-binaphthyl derivative having a binaphthyl skeleton having one or more substituents at an 8-position and/or an 8'-position and having no substituents at a 2-position or a 2'-position of the binaphthyl skeleton, wherein the one or more substituents are each independently an organic acid group, an aryl group having 6 to 30 carbon atoms, an alkyl group, an aralkyl group, a thioalkoxy group, a silyl group, a group containing a phosphorus atom directly bonded to the skeleton, an amino group, an iodo group, a bromo group or a chloro group.

* * * * *